US008252302B2

(12) United States Patent
Macdonald

(10) Patent No.: US 8,252,302 B2
(45) Date of Patent: Aug. 28, 2012

(54) METHODS AND COMPOSITIONS TO TREAT HEMORRHAGIC CONDITIONS OF THE BRAIN

(75) Inventor: R. Loch Macdonald, Toronto (CA)

(73) Assignee: Edge Therapeutics, Inc., New Providence, NJ (US)

( * ) Notice: Subject to any disclaimer, the term of this patent is extended or adjusted under 35 U.S.C. 154(b) by 8 days.

(21) Appl. No.: 13/032,514

(22) Filed: Feb. 22, 2011

(65) Prior Publication Data
US 2011/0142937 A1 Jun. 16, 2011

Related U.S. Application Data

(63) Continuation-in-part of application No. 12/137,320, filed on Jun. 11, 2008.

(60) Provisional application No. 60/943,124, filed on Jun. 11, 2007, provisional application No. 60/976,902, filed on Oct. 29, 2007, provisional application No. 61/306,758, filed on Feb. 22, 2010.

(51) Int. Cl.
| A61K 9/14 | (2006.01) |
| A61K 31/197 | (2006.01) |
| A61K 38/48 | (2006.01) |
| A61K 38/57 | (2006.01) |
| A61K 9/00 | (2006.01) |
| A61P 7/04 | (2006.01) |

(52) U.S. Cl. ............... 424/423; 424/484; 424/94.64; 424/400; 514/561; 514/13.7

(58) Field of Classification Search .................. None
See application file for complete search history.

(56) References Cited

U.S. PATENT DOCUMENTS

| 4,757,128 | A | 7/1988 | Domb et al. |
| 5,399,665 | A | 3/1995 | Barrera et al. |
| 5,747,058 | A | 5/1998 | Tipton et al. |
| 5,804,159 | A | 9/1998 | Eibl et al. |
| 5,968,542 | A | 10/1999 | Tipton |
| 6,123,956 | A | 9/2000 | Baker et al. |
| 7,608,750 | B2 | 10/2009 | Akira et al. |
| 2006/0094643 | A1 | 5/2006 | Svirkin et al. |
| 2006/0111282 | A1 | 5/2006 | Haaning et al. |
| 2008/0188400 | A1 | 8/2008 | Ropke et al. |
| 2008/0280811 | A1* | 11/2008 | Feener et al. ............... 514/2 |
| 2009/0156481 | A1* | 6/2009 | Brun et al. ................. 514/12 |

OTHER PUBLICATIONS

Beierlein, W. et al., "Forty Years of Clinical Aprotinin Use: A Review of 124 Hypersensitivity Reactions," Ann. Thorac. Surg., (Feb. 2005), vol. 79, pp. 741-748.
Aikawa, H. et al., "Experimental chronic subdural hematoma in mice. Gross morphology and light microscopic observations," J. Neurosurg., (Nov 1987), vol. 67, No. 5, pp. 710-716.

Diringer, M.N. et al., "Risk of Thromboembolic Events in Controlled Trials of rFVIIa in Spontaneous Intracerebral Hemorrhage," Stroke, (Mar. 2008), vol. 39, pp. 850-856.
Frati, a. et al., "Inflammation Markers and Risk Factors for Recurrence in 35 Patients with a Postraumatic Chronic Subdural Hematoma: a Prospective Study," J. Neurosurg., (Jan. 2004), vol. 100, No. 1, pp. 24-32.
Goodman & Gillman's The Pharmacological Basis of Therapeutics, Joel G. Hardman and Lee E. Limbird, Eds., McGraw Hill, 2001, pp. 1519-1520, pp. 1531-1532.
Elger, B. et al., "Ancrod reduces intracerebral hemorrhage quantified in vivo by magnetic resonance imaging in rats," J. Stroke Cerebrovasc. Dis., Jan.-Feb. 1998, vol. 7, No. 1, pp. 10-16.
Watanabe, S. et al. "Production of clinical form of chronic subdural hematoma in experimental animals," J. Neurosurg., (Nov. 1972), vol. 37, pp. 552-561.
Kou, J.H. et al. "Bioerosion and biocompatability of poly(d,l-lactic-co-glycolic acid) implants in brain," J. Controlled Release, (1997), vol. 43, pp. 123-130.
Langer, R. "New Methods of Drug Delivery," Science, (Sep. 28, 1990), vol. 249, pp. 1527-1533.
Mayer, S.A. et al., "Efficacy and Safety of Recombinant Activated Factor VII for Acute Intracerebral Hemorrhage," the New England Journal of Medicine, (May 15, 2008), vol. 358, No. 20, pp. 2127-2137.
Meltzer, M.E. et al., "The Impact of the Fibrinolytic System on the Risk of Venous and Arterial Thrombosis," Seminars Thrombosis Hemostasis, (2005), vol. 35, No. 5, pp. 468-477.
Monroe, D.M. et al., "Platelets and Thrombin Generation," Arterioscler. Thromb. Vasc. Biol., (Sep. 2002), vol. 22, pp. 1381-1389.
Nakaguchi, H. et al., "Factors in the Natural History of Chronic Subdural Hematomas that Influence their Postoperative Recurrence," J. Neurosurg., (Aug. 2001), vol. 95, No. 2, pp. 256-262.
Nomura, S. et al., "Characterization of Local Hyperfibrinolysis in Chronic Hematomas by SDS-PAGE and Immunoblot", J. Neurosurg., (Dec. 1994), vol. 81, No. 6, pp. 910-913.
Sawhney, A.S. et al., "Bioerodible Hydrogels Based on Photopolymerized Poly(ethylene glycol)-co-poly(alphahydroxy acid) Diacrylate Macromers", Macromolecules, (1993), vol. 26, p. 581-587.
Mayer, S.A., "Intracerebral hemorrhage: natural history and rationale of ultra-early hemostatic therapy," Intensive Care Med., (2002), vol. 28, pp. S235-S240.
Weiss, A. et al., "Signal Transduction by Lymphocyte Antigen Receptors," Cell, (Jan. 28, 1994), vol. 76, No. 2, pp. 263-274.
Veziers, J. et al. "Analysis of brain biocompatability of drug-releasing biodegradable microspheres by scanning and transmission electron microscopy," J. Neurosurg., (Sep. 2001), vol. 95, pp. 489-494.
Apfelbaum, R. et al. "Experimental production of subdural hematomas," J. Neurosurg., (Mar. 1974), vol. 40, pp. 336-346.
Han, H.J. et al. "One vs. Two Burr Hole Craniostomy in Surgical Treatment of Chronic Subdural Hematoma," J. Korean Neurosurg. Soc., (2009), vol. 46, pp. 87-92.

(Continued)

Primary Examiner — Robert A Wax
Assistant Examiner — Danah Al-Awadi
(74) Attorney, Agent, or Firm — Beverly W. Lubit; Greenberg Traurig, LLP

(57) ABSTRACT

The described invention provides a nonhuman animal model system for hemorrhagic brain conditions, methods for evaluating a substance for treating the hemorrhagic brain condition in a mammal, methods for treating hematoma expansion or recurrent rebleeding resulting from hemorrhagic brain conditions in a mammal, and pharmaceutical compositions for administration into or at a distance proximal to the hemorrhagic brain condition.

34 Claims, 9 Drawing Sheets

OTHER PUBLICATIONS

Tallon, J. et al. "The epidemiology of surgically treated acute subdural and epidural hematomas in patients with head injuries: a population-based study," Can. J. Surg., (Oct. 2008), vol. 51, No. 5, pp. 339-345.

Shim, Y.S. et al. "What are the Causative Factors for a Slow, Progressive Enlargement of a Chronic Subdural Hematoma?" Yonsei Med. J., (2007), vol. 48, No. 2, pp. 210-217.

Labadie, E. et al. "Physiopathogenesis of subdural hematomas; Part 1: Histological and biochemical comparisons of subcutaneous hematoma in rats with subdural hematomas in man." J. Neurosurg., (Oct. 1976), vol. 45, pp. 382-392.

Starke, R. et al. "Impact of a Protocol for Acute Antifibrinolytic Therapy on Aneurysm Rebleeding After Subarachnoid Hemorrhage," Stroke, (2008), vol. 39, pp. 2617-2621.

Sugiu, K. et al. "Rebleeding From a Vertebral Artery Dissecting Aneurysm After Endovascular Internal Trapping: Adverse Effect of Intrathecal Urokinase Injection or Incomplete Occlusion?" Neurol. Med. Chir. (Tokyo), (Dec. 2009), vol. 49, pp. 597-600.

Glover, D. et al. "Physiopathogenesis of subdural hematomas; Part 2: Inhibition of growth of experimental hematomas with dexamethasone." J. Neurosurg., (Oct. 1976), vol. 45, pp. 393-397.

Vandenabeele, F. et al. "Ultrastructure of the human spinal arachnoid mater and dura mater," J. Anat., (1996), vol. 189, pp. 417-430.

Datta, S. et al. "Neuroradiological aspects of subdural haemorrhages," Arch. Dis. Child, (2005), vol. 90, pp. 947-951.

Roos, Y. et al. "Antifibrinolytic therapy for aneurysmal subarachnoid haemorrhage." Cochrane Database of Systematic Reviews, 2003; Issue 2, Art. No. CD001245 (Abstract).

MacLellan, C. et al. "Intracerebral hemorrhage models in rat: comparing collagenase to blood infusion." J. Cereb. Blood Flow Metab., 2008; 28:516-525.

Weigel, R. et al. "Outcome of contemporary surgery for chronic subdural haematoma: evidence based review." J. Neurol. Neurosurg. Psychiatry, 2003; 74:937-943.

Tokmak, M. et al. "The role of exudation in chronic subdural hematomas." J. Neurosurg., Aug. 2007; 107:290-295.

Haines, D.E. "On the Question of a Subdural Space." The Anatomical Record, 1991; 230:3-21.

Rosenberg, Ga. et al. "Collagenase-induced intracerebral hemorrhage in rats." Stroke, 1990; 21:801-807.

Qureshi, A. et al. "Spontaneous Intracerebral Hemorrhage." N. Engl. J. Med., May 2001; 344(19):1450-1460.

Carmichael, S.T. et al. "Genomic profiles of damage and protection in human intracerebral hemorrhage." J. Cereb. Blood Flow Metab., Nov. 2008; 28(11):1860-1875.

Murakami, H. et al. "Why do chronic subdural hematomas continue to grow slowly and not coagulate? Role of thrombomodulin in the mechanism." J. Neurosurg., 2002; 96:877-884.

Broderick, J.P. et al. "volume of intracerebral hemorrhage. A powerful and easy-to-use predictor of 30-day mortality." Stroke, 1993; 24:987-993.

Broderick, J.P. et al. "Guidelines for the Management of Spontaneous Intracerebral Hemorrhage: A Statement for Healthcare Professionals From a Special Writing Group of the Stroke Council, American Heart Association." Stroke, 1999; 30:905-915.

Mayberg, M. R. et al., "The significance of morphological changes in cerebral arteries after subarachnoid hemorrhage," J. Neurosurg., (1990), vol. 72, pp. 626-633.

Mayberg, M. R. et al., "The role of hemoglobin in arterial narrowing after subarachnoid hemorrage," J. Neurosurg., (1990), vol. 72, pp. 634-640.

* cited by examiner

METHODS AND COMPOSITIONS TO TREAT HEMORRHAGIC CONDITIONS OF THE BRAIN

CROSS REFERENCE TO RELATED APPLICATIONS

This application is a continuation-in-part of U.S. application Ser. No. 12/137,320, entitled "A Drug Delivery System for the Prevention of Cerebral Vasospasm" (filed Jun. 11, 2008), which claims the benefit of priority from U.S. Provisional Applications No. 60/943,124 (filed Jun. 11, 2007) and 60/976,902 (filed Oct. 29, 2007). It further claims the benefit of priority of U.S. Provisional Application No. 61/306,758 (filed Feb. 22, 2010). Each of these applications is incorporated by reference herein in its entirety.

FIELD OF THE INVENTION

The described invention relates to methods and compositions to treat hemorrhagic conditions of the brain.

BACKGROUND

The central nervous system is a bilateral and essentially symmetrical structure with seven main parts: the spinal cord, medulla oblongata, pons, cerebellum, midbrain, diencephalon, and the cerebral hemispheres. FIG. 1 shows a lateral view of the human brain from Stedman's Medical Dictionary, $27^{th}$ Edition, plate 7 at A7 (2000).

The spinal cord, the most caudal part of the central nervous system, receives and processes sensory information from the skin, joints, and muscles of the limbs and trunk and controls movement of the limbs and the trunk. It is subdivided into cervical, thoracic, lumbar and sacral regions. The spinal cord continues rostrally as the brainstem, which consists of the medulla, pons, and midbrain. The brainstem receives sensory information from the skin and muscles of the head and provides the motor control for the muscles of the head. It also conveys information from the spinal cord to the brain and from the brain to the spinal cord, and regulates levels of arousal and awareness through the reticular formation. The brainstem contains several collections of cell bodies, the cranial nerve nuclei. Some of these receive information from the skin and muscles of the head; others control motor output to muscles of the face, neck and eyes. Still others are specialized for information from the special senses: hearing, balance and taste. (Kandel, E. et al., Principles of Neural Science, $4^{th}$ Ed., p. 8, 2000).

The medulla oblongata, which lies directly rostral to the spinal cord, includes several centers responsible for vital autonomic functions, such as digestion, breathing and the control of heart rate (Kandel, E. et al., Principles of Neural Science, $4^{th}$ Ed., p. 8, 2000).

The pons, which lies rostral to the medulla, conveys information about movement from the cerebral hemispheres to the cerebellum (Kandel, E. et al., Principles of Neural Science, $4^{th}$ Ed., p. 8, 2000).

The cerebellum lies behind the pons and is connected to the brain stem by several major fiber tracts called peduncles. The cerebellum modulates the force and range of movement, and is involved in the learning of motor skills. It also contributes to learning and cognition (Kandel, E. et al., Principles of Neural Science, $4^{th}$ Ed., p. 8, 2000).

The midbrain, which lies rostral to the pons, controls many sensory and motor functions, including eye movements and the coordination of visual and auditory reflexes (Kandel, E. et al., Principles of Neural Science, $4^{th}$ Ed., p. 8, 2000).

The diencephalon lies rostral to the midbrain and contains two structures. One, the thalamus, processes most of the information reaching the cerebral cortex from the rest of the central nervous system and is involved in other functions including motor control, autonomic function and cognition. The other, the hypothalamus, regulates autonomic, endocrine, and visceral function (Kandel, E. et al., Principles of Neural Science, $4^{th}$ Ed., p. 8, 2000).

The cerebral hemispheres consist of a heavily wrinkled outer layer, the cerebral cortex, and three deep-lying structures—the basal ganglia, which participate in regulating motor performance; the hippocampus, which is involved with aspects of learning and memory storage; and the amygdaloid nuclei, which coordinate the autonomic and endocrine responses of emotional states (Kandel, E. et al., Principles of Neural Science, $4^{th}$ Ed., p. 8, 2000).

The cerebral cortex is divided into four lobes: the frontal lobe, parietal lobe, temporal lobe and occipital lobe. The surfaces of the cerebral hemispheres contain many grooves or furrows, known as fissures and sulci. The portions of brain lying between these grooves are called convolutions or gyri. The lateral cerebral fissure (fissure of Sylvius) separates the temporal from the frontal lobe. The central sulcus (Rolandic sulcus) separates the frontal from the parietal lobe (Kandel, E. et al., Principles of Neural Science, $4^{th}$ Ed., p. 8, 2000).

1. Meninges of the Brain

The meninges, three distinct connective tissue membranes that enclose and protect the brain and spinal cord, are named (from outer to inner layer) the dura mater, the arachnoid, and the pia mater. FIG. 2 shows an illustrative sagittal view of the human brain (J. G. Chusid, Correlative Neuroanatomy & Functional Neurology, $18^{th}$ Ed., p. 46, 1982).

1.1. Dura Mater

The dura mater is a dense fibrous structure that covers the brain and spinal cord. It has an inner meningeal and an outer periosteal or endosteal layer. The dural layers over the brain generally are fused, except where they separate to provide space for the venous sinuses and where the inner layer forms septa between brain portions. The outer layer attaches firmly to the inner surface of the cranial bones and sends vascular and fibrous extensions into the bone itself. Around the margin of the foramen magnum (the large opening in the base of the skull forming the passage from the cranial cavity to the spinal cavity) it is closely adherent to the bone, and is continuous with the spinal dura mater.

The cranial dura mater consists of fibroblasts, abundant extracellular collagen and a few elastic fibers arranged in flattened laminae which are imperfectly separated by lacunar spaces and blood vessels into two layers: an inner (meningeal) layer and an outer (endosteal) layer, closely connected together, except in certain situations, where they separate to form sinuses for the passages of venous blood or form septae between portions of the brain. The outer surface of the dura mater is rough and fibrillated (composed of fibers), and adheres closely to the inner surfaces of the bones, the adhesions being most marked opposite the cranial sutures (the immovable joints between the bones of the skull or cranium). The endosteal layer is the internal periosteum for the cranial bones, and contains the blood vessels for their supply. The meningeal layer is lined on its inner surface by a layer of unique elongated, flattened fibroblasts that have been called dural border cells. There is no collagen in this layer and the cells are not connected by cell junctions. They are frequently separated by extracellular spaces filled with amorphous non-filamentous material. The meningeal layer further comprises two lamellas: the compact lamella and the loose lamella; the former generally contains tight fibrous tissue and few blood vessels, but the latter contains some blood vessels. FIG. 3 is a drawing of a cross section of the three meningeal layers that cover the brain (Haines, D. E., Anatomical Record 230: 3-21, 1991). The dura mater sends inward four processes that divide the cavity of the skull into a series of freely communicating compartments and further provides for the protection of the different parts of the brain.

The processes of the cranial dura mater, which project into the cavity of the skull, are formed by reduplications of the inner (or meningeal) layer of the membrane. These processes include: (1) the falx cerebri, (2) the tentorium cerebelli, (3) the falx cerebelli, and (4) the diaphragma sellae.

The falx cerebri is a strong, arched process with a sickle-like form which descends vertically in the longitudinal fissure between the cerebral hemispheres. It is narrow in front, where it is attached to the ethmoid bone (the bone at the base of the cranium and the root of the nose) at the crista galli (the triangular midline process of the ethmoid bone); and broad behind, where it is connected with the upper surface of the tentorium cerebelli (an arched fold of dura mater that covers the upper surface of the cerebellum). Its upper margin is convex, and attached to the inner surface of the skull in the middle line, as far back as the internal occipital protuberance; it contains the superior sagittal sinus. Its lower margin is free and concave, and contains the inferior sagittal sinus.

The tentorium cerebelli is an arched lamina, elevated in the middle, and inclining downward toward the circumference. It covers the superior surface of the cerebellum, and supports the occipital lobes of the brain. Its anterior border is free and concave, and bounds a large oval opening (the incisura tentorii) for the transmission of the cerebral peduncles (the massive bundle of corticofugal nerve fibers passing longitudinally over the ventral surface of the midbrain on each side of the midline) as well as ascending sensory and autonomic fibers and other fiber tracts. The tentorium cerebelli is attached, behind, by its convex border, to the transverse ridges upon the inner surface of the occipital bone, and there encloses the transverse sinuses; and, in front, to the superior angle of the petrous part of the temporal bone on either side, enclosing the superior petrosal sinuses. At the apex of the petrous part of the temporal bone the free and attached borders meet, and, crossing one another, are continued forward to be fixed to the anterior and posterior clinoid processes respectively. The posterior border of the falx cerebri is attached to the middle line of its upper surface. The straight sinus is placed at the junction of the falx cerebri and the tentorium cerebelli.

The falx cerebelli is a small triangular process of dura mater that separates the two cerebellar hemispheres. Its base is attached, above, to the under and back part of the tentorium; and its posterior margin is attached to the lower division of the vertical crest on the inner surface of the occipital bone. As it descends, it sometimes divides into two smaller folds, which are lost on the sides of the foramen magnum.

The diaphragma sellae is a small circular horizontal fold, which roofs in the sella turcica (a saddlelike prominence on the upper surface of the sphenoid bone of the skull, situated in the middle cranial fossa and dividing it into two halves) and almost completely covers the pituitary gland (hypophysis); a central opening of variable size transmits the infundibulum (a funnel-shaped extension of the hypothalamus connecting the pituitary gland to the base of the brain).

The arteries of the dura mater are numerous. The meningeal branches of the anterior and posterior ethmoidal arteries and of the internal carotid artery, and a branch from the middle meningeal artery supply the dura of the anterior cranial fossa. The middle and accessory meningeal arteries of the internal maxillary artery; a branch from the ascending pharyngeal artery, which enters the skull through the foramen lacerum; branches from the internal carotid artery, and a recurrent branch from the lacrimal artery supply the dura of the middle cranial fossa. Meningeal branches from the occipital artery, one entering the skull through the jugular foramen, and another through the mastoid foramen; the posterior meningeal artery from the vertebral artery; occasional meningeal branches from the ascending pharyngeal artery, entering the skull through the jugular foramen and hypoglossal canal; and a branch from the middle meningeal artery supply the dura of the posterior cranial fossa.

The veins returning the blood from the cranial dura mater anastomose with the diploic veins or end in the various sinuses. Many of the meningeal veins do not open directly into the sinuses, but open indirectly through a series of ampullae, termed venous lacunae. These are found on either side of the superior sagittal sinus, especially near its middle portion, and are often invaginated by arachnoid granulations; they also exist near the transverse and straight sinuses. They communicate with the underlying cerebral veins, and also with the diploic and emissary veins.

The nerves of the cranial dura mater are filaments derived from the trigeminal, glossopharyngeal, vagal, second and third spinal, sphenopalatine, otic, and superior cervical ganglia and supply unmyelinated and myelinated sensory and autonomic fibers.

1.2. Arachnoid

The middle meningeal layer, the arachnoid, is a delicate avascular membrane lying between the pia mater and the dura mater. It is separated from the overlying dura mater by the subdural space and from the underlying pia mater by the subarachnoid space, which contains cerebrospinal fluid.

The arachnoid consists of an outer cell layer of low cuboidal mesothelium. There is a space of variable thickness filled with cerebrospinal fluid and traversed by trabeculae and membranes consisting of collagen fibrils and cells resembling fibroblasts. The inner layer and the trabeculae are covered by a somewhat low type of cuboidal mesothelium, which in places are flattened to a pavement type and blends on the inner deep layer with the cells of the pia mater. The arachnoid further contains a plexus of nerves derived from the motor root of the trigeminal, the facial, and the accessory cranial nerves.

The cranial part (arachnoidea encephali) of the arachnoid invests the brain loosely, and does not dip into the sulci (depressions or fissures in the surface of the brain) between the gyri (upraised folds or elevations in the surface of the brain), nor into the fissures, with the exception of the longitudinal fissure and several other larger sulci and fissures. On the upper surface of the brain, the arachnoid is thin and transparent; at the base it is thicker. It is slightly opaque toward the central part of the brain, where it extends across between the two temporal lobes in front of the pons so as to leave a considerable space between the pons and the brain.

The arachnoid surrounds the cranial and spinal nerves, and encloses them in loose sheaths as far as their points of exit from the skull.

Subarachnoid Cavity

The subarachnoid cavity or subarachnoid space, which is the space between the outer cellular layer of the arachnoid and the pia mater, is occupied by tissue consisting of trabeculae of delicate connective tissue and intercommunicating channels in which the cerebrospinal fluid is contained. This cavity is small on the surface of the hemispheres of the brain; on the summit of each gyrus, the pia mater and the arachnoid are in close contact, but triangular spaces are left in the sulci between the gyri, in which the subarachnoid trabecular tissue is found, because the pia mater dips into the sulci, whereas the arachnoid bridges across them from gyrus to gyrus. At certain parts of the base of the brain, the arachnoid is separated from the pia mater by wide intervals, which communicate freely with each other and are named subarachnoid cisternae; the subarachnoid tissue in these cisternae is less abundant.

Subarachnoid Cisternae (Cisternae Subarachnoidales)

The cisterna cerebellomedullaris (cisterna magna) is triangular on sagittal section, and results from the arachnoid bridging over the space between the medulla oblongata and the under surfaces of the hemispheres of the cerebellum; it is continuous with the subarachnoid cavity of the spinal cord at the level of the foramen magnum.

The cisterna pontis is a considerable space on the ventral aspect of the pons. It contains the basilar artery, and is continuous behind the ponswith the subarachnoid cavity of the spinal cord, and with the cisterna cerebellomedullaris; in front of the pons, it is continuous with the cisterna interpeduncularis.

The cisterna interpeduncularis (cisterna basalis) is a wide cavity where the arachnoid extends across between the two temporal lobes. It encloses the cerebral peduncles and the structures contained in the interpeduncular fossa, and contains the arterial circle of Willis. In front, the cisterna interpeduncularis extends forward across the optic chiasma, forming the cisterna chiasmatis, and on to the upper surface of the corpus callosum. The arachnoid stretches across from one cerebral hemisphere to the other immediately beneath the free border of the falx cerebri, and thus leaves a space in which the anterior cerebral arteries are contained. The cisterna fossae cerebri lateralis is formed in front of either temporal lobe by the arachnoid bridging across the lateral fissure. This cavity contains the middle cerebral artery. The cisterna venae magnae cerebri occupies the interval between the splenium of the corpus callosum and the superior surface of the cerebellum; it extends between the layers of the tela chorioidea of the third ventricle and contains the great cerebral vein.

The subarachnoid cavity communicates with the general ventricular cavity of the brain by three openings; one, the foramen of Majendie, is in the middle line at the inferior part of the roof of the fourth ventricle; the other two (the foramina of Luschka) are at the extremities of the lateral recesses of that ventricle, behind the upper roots of the glossopharyngeal nerves.

The arachnoid villi are tufted prolongations of pia-arachnoid that protrude through the meningeal layer of the dura mater and have a thin limiting membrane. Tufted prolongations of pia-arachnoid composed of numerous arachnoid villi that penetrate dural venous sinuses and effect transfer of cerebrospinal fluid to the venous system are called arachnoid granulations.

An arachnoidal villus represents an invasion of the dura by the arachnoid membrane, whereby arachnoid mesothelial cells come to lie directly beneath the vascular endothelium of the great dural sinuses. Each villus consists of the following parts: (1) in the interior is a core of subarachnoid tissue, continuous with the meshwork of the general subarachnoid tissue through a narrow pedicle, by which the villus is attached to the arachnoid; (2) around this tissue is a layer of arachnoid membrane, limiting and enclosing the subarachnoid tissue; (3) outside this is the thinned wall of the lacuna, which is separated from the arachnoid by a potential space, which corresponds to and is continuous with the potential subdural space; and (4) if the villus projects into the sagittal sinus, it will be covered by the greatly thinned wall of the sinus, which may consist merely of endothelium. Fluid injected into the subarachnoid cavity will find its way into these villi. Such fluid passes from the villi into the venous sinuses into which they project.

1.3. Pia Mater

The pia mater is a thin connective tissue membrane that is applied to the surface of the brain and spinal cord. Blood vessels supplying the brain travel through the pia into the brain. The pia mater is absent at the foramen of Majendie and the two foramina of Luschka and is perforated by all the blood vessels as they enter or leave the nervous system, and therefore is considered to be an incomplete membrane. In perivascular spaces, the pia apparently enters as a mesothelial lining of the outer surface of the space; a variable distance from the exterior, these cells become unrecognizable and are apparently lacking, replaced by neuroglia elements. The inner walls of the perivascular spaces likewise seem to be covered for a certain distance by the mesothelial cells, reflected with the vessels from the arachnoid covering of these vascular channels as they traverse the subarachnoid spaces.

The cranial pia mater (pia mater encephali; pia of the brain) invests the entire surface of the brain, dips between the cerebral gyri and cerebellar laminae, and is invaginated to form the tela chorioidea of the third ventricle, and the choroid plexuses of the lateral and third ventricles. As it passes over the roof of the fourth ventricle, it forms the tela chorioidea and the choroid plexuses of the fourth ventricle. On the cerebellum the membrane is more delicate; the vessels from its deep surface are shorter, and its relations to the cortex are not so intimate.

The pia mater forms sheaths for the cranial nerves

2. Circulation of the Brain

The circle of Willis at the base of the brain is the principal arterial anastomotic trunk of the brain. Blood reaches it mainly via the vertebral and internal carotid arteries (See FIG. 4); anastomoses occur between arterial branches of the circle of Willis over the cerebral hemispheres and via extracranial arteries that penetrate the skull through various foramina.

The circle of Willis is formed by anastamoses between the internal carotid, basilar, anterior cerebral, anterior communicating, posterior cerebral, and posterior communicating arteries. The internal carotid artery terminates in the anterior cerebral and middle cerebral arteries. Near its termination, the internal carotid artery gives rise to the posterior communicating artery, which joins caudally with the posterior cerebral artery. The anterior cerebral arteries connect via the anterior communicating artery.

The blood supply to the cerebral cortex mainly is via cortical branches of the anterior cerebral, middle cerebral, and posterior cerebral arteries, which reach the cortex in the pia mater. FIG. 5 shows an illustrative view of the arterial supply of the cerebral cortex where 1 is the orbitofrontal artery; 2 is the prerolandic artery; 3 is the rolandic artery; 4 is the anterior parietal artery; 5 is the posterior parietal artery; 6 is the angular artery; 7 is the posterior temporal artery; 8 is the anterior temporal artery; 9 is the orbital artery; 10 is the frontopolar artery; 11 is the callosomarginal artery; 12 is the posterior internal frontal artery; and 13 is the pericallosal artery (Correlative Neuroanatomy & Functional Neurology, $18^{th}$ Ed., p. 50, 1982).

The lateral surface of each cerebral hemisphere is supplied mainly by the middle cerebral artery. The medial and inferior surfaces of the cerebral hemispheres are supplied by the anterior cerebral and posterior cerebral arteries.

The middle cerebral artery, a terminal branch of the internal carotid artery, enters the lateral cerebral fissure and divides into cortical branches that supply the adjacent frontal, temporal, parietal and occipital lobes. Small penetrating arteries, the lenticulostriate arteries, arise from the basal portion of the middle cerebral artery to supply the internal capsule and adjacent structures.

The anterior cerebral artery extends medially from its origin from the internal carotid artery into the longitudinal cerebral fissure to the genu of the corupus callosum, where it turns posteriorly close to the corpus callosum. It gives branches to the medial frontal and parietal lobes and to the adjacent cortex along the medial surface of these lobes.

The posterior cerebral artery arises from the basilar artery at its rostral end usually at the level of the midbrain, curves dorsally around the cerebral peduncle, and sends branches to the medial and inferior surfaces of the temporal lobe and to the medial occipital lobe. Branches include the calcarine artery and perforating branches to the posterior thalamus and subthalamus.

The basilar artery is formed by the junction of the vertebral arteries. It supplies the upper brain stem via short paramedian, short cicumferential, and long circumferential branches.

The midbrain is supplied by the basilar, posterior cerebral, and superior cerebellar arteries. The pons is supplied by the basilar, anterior cerebellar, inferior cerebellar, and superior cerebellar arteries. The medulla oblongata is supplied by the vertebral, anterior spinal, posterior spinal, posterior inferior cerebellar, and basilar arteries. The cerebellum is supplied by the cerebellar arteries (superior cerebellar, anterior inferior cerebellar, and posterior inferior cerebellar arteries).

The choroid plexuses of the third and lateral ventricles are supplied by brances of the internal carotid and posterior cerebral arteries. The choroid plexus of the fourth ventricle is supplied by the posterior inferior cerebellar arteries.

Venous drainage from the brain chiefly is into the dural sinuses, vascular channels lying within the tough structure of the dura. The dural sinuses contain no valves and, for the most part, are triangular in shape. The superior longitudinal sinus is in the falx cerebri.

3. Hemorrhagic Conditions of the Brain

Each year, more than 2,000,000 people worldwide suffer spontaneous or traumatic intracerebral hemorrhage ("ICH"), both of which have poor outcomes, are difficult to treat, and have a high mortality and morbidity rate. Spontaneous ICH has the highest morbidity and mortality rate of all strokes. Chronic subdural hematoma ("SDH") also is a common neurosurgical problem. Little epidemiologic data exists on its incidence, but neurosurgical practice suggests the incidence is more than 30 cases per 100,000 population per year.

Treatment for hemorrhagic brain conditions includes surgical evacuation through craniotomy, or less invasively, through a burr hole, all of which are of variable effectiveness. An important complication of these forms of bleeding is post-operative rebleeding, which occurs in 10-30% of cases and increases morbidity and mortality. Post-operative bleeding also can occur after intracranial operations for other conditions such as brain tumors, epilepsy, infections and vascular malformations of the brain.

3.1. Intracerebral Hemorrhage (ICH)

The term "nontraumatic ICH" as used herein refers to bleeding into the parenchyma of the brain that may extend into the ventricles, and, in some cases, the subarachnoid space, that is not caused or associated with trauma and especially traumatic injury. The term "traumatic ICH" as used herein refers to such bleeding that is caused by, or associated with trauma, and especially traumatic injury.

Spontaneous and traumatic ICHs are important causes of morbidity and mortality throughout the world. The estimated annual incidence of spontaneous ICH ranges from 15-30/100,000 population. Treatment consists of intensive care support, management of increased intracranial pressure and surgical evacuation of the hematoma in selected cases. These treatments are not very effective; mortality exceeds 50% and survivors often have severe morbidity. One cause of poor outcome is rebleeding before or after surgical evacuation of a hematoma or following surgical resection of a tumor, infection or vascular malformation. Hematoma growth occurs in up to 70% of patients imaged within 3 hours of an ICH. Furthermore, hemorrhage expansion is an independent determinant of death and disability. In addition to ICH growth, other predictors of poor outcome include age, baseline volume of the hemorrhage. Glasgow coma scale score, intraventricular hemorrhage, and infratentorial location. Postoperative rebleeding also occurs in up to 6% of patients, but is more common with early surgery (40% within 4 hours of ictus). However, patients operated on early may benefit most from surgery, so decreasing the risk of early rebleeding may be critical. There are reports in the medical literature of administering drugs that prevent bleeding to patients who have undergone surgery to remove ICH. Systemic (intravenous or meaning into the body in general) administration of anti fibrinolytic drugs or activated factor VIIa to reduce rebleeding did not improve outcome, due, in part, to systemic side effects of the drugs. For example, patients with ICH who are treated with recombinant Factor VII are at increased risk for arterial thromboembolic complications, most commonly cerebral infarction and myocardial ischemia, as indicated by elevated troponin I concentrations (Diringer, M N, et al., Stroke 13: 850-56, 2008).

Traumatic ICH caused by traumatic brain injury (TBI) is even more common than spontaneous ICH. Approximately 10% of TBIs (1,400,000 annual U.S. cases) are complicated by ICH requiring surgery. How commonly recurrent bleeding occurs into contused brain after trauma is not well-documented. According to some estimates, recurrent bleeding after trauma occurs in up to 10% of patients, therefore is a serious concern for neurosurgeons.

3.2. Pathogenesis of ICH

ICH commonly occurs in the basal ganglia, thalamus, brain stem (predominantly the pons), cerebral hemispheres, and the cerebellum. Extension into the ventricles occurs in association with deep, large hematomas. Edematous parenchyma, often discolored by degradation products of hemoglobin, is visible adjacent to the clot. Histologic sections are characterized by the presence of edema, neuronal damage, macrophages, and neutrophils in the region surrounding the hematoma. The hemorrhage spreads between planes of white-matter cleavage, causing some destruction of the brain structure, and leaving nests of intact neural tissue within and surrounding the hematoma. This pattern of spread accounts for the presence of viable and salvageable neural tissue in the immediate vicinity of the hematoma.

Intraparenchymal bleeding commonly results from the rupture of the small penetrating arterioles that originate from basilar arteries or from the anterior, middle, or posterior cerebral arteries. Degenerative changes in the arteriolar walls by chronic hypertension reduce compliance, weaken the wall, and increase the likelihood of spontaneous rupture. Studies suggest that most bleeding occurs at or near the bifurcation of affected arteries, where prominent degeneration of the tunica media and smooth muscles can be seen.

An ICH expands over time. Studies using computed tomographic (CT) scans have shown that the hematoma expanded in 26% of patients within 1 hour after the initial CT scan and in another 12% within 20 hours. Others studies have shown that the hematoma expanded in 20% of patients with ICH, occurring in 36% of patients who presented within 3 hours after the onset of the hemorrhage and in 11% of those who presented more than 3 hours after the onset. This expansion has been attributed to continued bleeding from the primary source and to mechanical disruption of surrounding vessels. Acute hypertension, a local coagulation deficit, or both may be associated with expansion of the hematoma.

The presence of hematoma initiates edema and neuronal damage in surrounding parenchyma. Fluid begins to collect immediately in the region around the hematoma, edema usually increases for up to five days, and it has been observed for as long as two weeks after a stroke. Early edema around the hematoma results from the release and accumulation of osmotically active serum proteins from the clot. Vasogenic edema and cytotoxic edema subsequently follow due to the disruption of the blood-brain barrier, the failure of the sodium pump, and the death of neurons.

The delay in the breakdown of the blood-brain barrier and the development of cerebral edema after ICH suggest that there may be secondary mediators of both neural injury and edema. It generally is believed that blood and plasma products mediate most secondary processes that are initiated after an ICH. It is uncertain whether cerebral ischemia occurs as a result of mechanical compression or some chemical effect of the hemorrhage in the region surrounding the hematoma. Neuronal death in the region around the hematoma predominantly is necrotic (some studies suggest the presence of programmed cell death (apoptosis) as well).

3.3. Classification of ICH

Depending on the underlying cause of bleeding, ICH is classified as either primary or secondary. Primary ICH, accounting for 78-88% of cases, originates from the spontaneous rupture of small vessels damaged by chronic hypertension, amyloid angiopathy, or some other cause. Secondary ICH in a minority of patients occurs in association with vascular abnormalities (such as arteriovenous malformations and aneurysms), tumors, or impaired coagulation.

3.4. Biomarkers of ICH

The surfaces of all cells in the body are coated with specialized protein receptors that have the capability to selectively bind or adhere to other signaling molecules (Weiss and Littman, Cell, 76:263-74, 1994). These receptors and the molecules that bind to them are used for communicating with other cells and for carrying out proper cell functions in the body. Each cell type has a certain combination of receptors, or markers, on their surface that makes them distinguishable from other kinds of cells.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints can be biomarkers that are intended to substitute for a clinical endpoint; these biomarkers are demonstrated to predict a clinical endpoint with a confidence level acceptable to regulators and the clinical community.

Studies have indicated that ICH affects coordinated networks of gene expression in inflammatory, anti-inflammatory, and neuronal signaling systems in human perihematomal tissue within the first day of hemorrhage. Perihematomal tissue includes gray and white matter structures. Perihematomal edema with mass effect is an almost universal complication of ICH. A molecular network of proinflammatory signaling starts with the cytokines/chemokines interleukin 1β (IL-1β), IL-8, IL-6 receptor, CCR1, CXCL2/MIP2, and CXCL3. These molecules signal IL and Toll-like receptors to activate a signaling cascade that involves the Pas ligand, nuclear factor-κB (NF-κB), and the MEKK/JNK pathway. Anti-inflammatory signaling is activated in ICH in a cascade that progresses from annexins A1 and A2, IL-10 and transforming growth factor-β (TGF-β), through downstream calcium-binding, cytoskeletal and ribosomal proteins, and c-Myc. ICH downregulates parallel neuronal signaling systems in perihematomal tissue. These downregulated neuronal genes include molecules that function in glutamate signaling, presynaptic structure, postsynaptic structure, and a number of ion channels and calcium signaling proteins. At the cellular level, specific cell types respond to ICH with altered expression of these genes. Astrocytes in the perihematomal rim express aquaporin 9 and tissue inhibitor of metalloproteinase-1 (TIMP-1). Annexin A2 is induced in inflammatory cells in the hemorrhage and in neurons that border the hemorrhage site. Oligodendrocytes in injured white matter express the inflammatory chemokine CCR1. Inflammatory and endothelial cells in the immediate perihematomal rim and hemorrhage site express the IL receptor IL1R1. At the protein level, select members of the molecular cascades induced in perihematomal tissue after ICH localize with different glial and neuronal cell types in these two tissue compartments.

Accordingly, ICH induces several biomarkers that may be used to study ICH: (i) inflammatory cytokine signaling centered around tumor necrosis factor-α (TNF-α), IL-1β, and IL-6; (ii) glial edema-associated genes including aquaporin 4 and vascular endothelial growth factor (VEGF); and (iii) the expression of matrix metalloproteinase 9 (MMP9) and serum proteases (plasminogen) as mediators of secondary extracellular matrix damage.

Tumor necrosis factor-α (TNF-α, TNF, cachexin, cachectin) is a cytokine involved in systemic inflammation, the regulation of immune cells, apoptotic death, and tumorigenesis inhibition. Two receptors (TNF-R1 and TNF-R2) bind to TNF-α. TNF-R1 is expressed in most tissues, whereas TNF-R2 is found in cells of the immune system. Binding of TNF-α to the TNF receptors causes a conformational change in the receptor, which allows for the initiation of several cascades including (i) the activation of NE-κB (which mediates the transcription of a vast array of proteins involved in cell survival and proliferation, inflammatory response, and anti-apoptotic factors); (ii) the activation of MAPK pathways, including the JNK pathway, which is involved in cell differentiation, proliferation, and generally is pro-apoptotic; and (iii) the induction of death signaling.

Interleukin-6 (IL-6), a cytokine with both proinflammatory and anti inflammatory properties, is secreted by among others, T cells and macrophages, to stimulate an immune response to trauma, and smooth muscle cells in the tunica media of many blood vessels. IL-6 is an important mediator of fever and the acute phase response. IL-6 signals through a cell-surface Type 1 cytokine receptor (consisting of IL-6Rα (ligand-biding chain) and gp130 (signal-transducing component). As IL-6 interacts with its receptor, it triggers the gp130 and IL-6R proteins to form a complex, thus activating the receptor. These complexes bring together the intracellular regions of gp130 to initiate a signal transduction cascade through certain transcription factors, Janus kinases (JAKs), and signal transducers and activators of transcription (STATs).

Interleukin 1β (IL-1β) is a cytokine that is produced by activated macrophages as a proprotein, which is processed proteolytically to its active form by caspase 1 (CASP/ICE). IL-1β is an important mediator of the inflammatory response, and is involved in several cellular activities, including, but not limited to, cell proliferation, differentiation and apoptosis.

Aquaporin 4 is an integral membrane protein that conducts water through the cell membrane. It is expressed constitutively in the basolateral cell membrane of principal collecting duct cells in the kidney. Aquaporin 4 also is expressed in astrocytes and is unregulated by direct insult to the central nervous system.

Vascular endothelial growth factor (VEGF) stimulates the growth of new blood vessels. All members of the VEGF family stimulate cellular responses by binding to tyrosine kinase receptors (VEGFRs) on the cell surface, causing them to dimerize and to become activated through transphosphorylation (although to different sites, times and extents).

Matrix metalloproteinases (MMP) are zinc-dependent endopeptidases capable of degrading various extracellular matrix proteins. The MMPs share a common domain structure including the pro-peptide, the catalytic domain, and the haemopexin-like C-terminal domain, which is linked to the catalytic domain by a flexible hinge region. MMPs are known to be involved in the cleavage of cell surface receptors, the release of apoptotic ligands (such as FAS ligand), and chemokine/cytokine in/activation. It generally is believed that MMPs have a role in cell proliferation, migration (adhesion/dispersion), differentiation, angiogenesis, apoptosis and host defense.

3.5. Need for ICH Treatments and Model Systems

Spontaneous ICH is more than twice as common as subarachnoid hemorrhage (SAH) and is more likely to result in death or major disability than cerebral infarction or SAH. The benefit of surgical or medical treatment for patients with spontaneous ICH remains inconclusive.

Advancing age and hypertension are significant risk factors for spontaneous ICH. The most important cause of ICH generally is regarded as pathophysiological changes in small arteries and arterioles due to sustained hypertension. Additionally, cerebral amyloid angiopathy increasingly is recognized as a cause of lobar ICH in the elderly. Other causes of ICH include vascular malformations, ruptured aneurysms, coagulation disorders, use of anticoagulants and thrombolytic agents, hemorrhage into a cerebral infarct, bleeding into brain tumors, and drug abuse.

Although guidelines for medical treatment and surgical removal of ICH are available, management of ICH by neurologists and neurosurgeons varies greatly throughout the world. Despite a lack of proven benefit for surgery to remove an ICH, it is estimated that over 7,000 such operations are performed annually in the United States. A major complication is rebleeding. Rebleeding after surgery occurs in up to 30% of cases and increases morbidity and mortality.

A significant need remains for new therapeutics and therapeutic methods for preventing the recurrence of bleeding in an ICH. Further, the lack of an accurate and reproducible model system for ICH has impaired research and development of potential new therapeutics and therapeutic methods for preventing rebleeding.

4.1. Subdural Hematoma (SDH)

A subdural hematoma (SDH) is a form of traumatic brain injury in which blood gathers between the dura mater and the arachnoid. The subdural space is a potential space that develops by separation of the cells in the dural border cell layer. The outer wall is the dura mater, a dense fibrous membrane with poor vascularization, and the inner wall is the vascularized arachnoid with no capillary bed. The inner layer of the dura mater and the remaining dural border cells have a high reaction potential for cellular organization and contains a very fine network of interconnected capillaries. Unlike epidural hematomas, which usually are caused by tears in arteries resulting in a buildup of blood between the dura and the skull, subdural bleeding usually results from tears in veins that cross the subdural space thereby allowing blood to gather within the inner meningeal or dural border cell layer of the dura mater. This bleeding then often separates the dura and the arachnoid layers.

Subdural hematomas are divided into acute, subacute, and chronic, depending on their speed of onset.

Acute SDHs usually are due to trauma and are among the most lethal of all head injuries. ASDHs have a high mortality rate if they are not treated rapidly with surgical decompression. When an acute hematoma is limited to subdural space without arachnoid tear, the hematoma splits within the layer of dural border cells.

Subacute SDH generally are described as those hematomas that develop within 2 weeks to 6 weeks of head trauma.

Chronic SDH arises from bleeding that occurs in the "potential" space between the dura and the arachnoid, and usually is said to require about 6 weeks to develop. This "potential" space is described as such since, in normal circumstances, the brain and its covering of arachnoid and pia abut directly against the dura: However, with advancing age, atrophy of the cerebral cortex occurs and a true "subdural" space may develop by separation of cells in the dural border cell layer. Subsequently, the small veins that drain the cortex may be adherent to the dura, and these "bridging" veins traverse this now enlarged subdural space. Accordingly, these "bridging" veins are prone to tear and bleed with any trauma that would apply inertial force on the brain. This may occur after a quite minor incident, such as a slip or fall in an elderly person, the banging of the head against a doorway, or some other relatively minor incident. Acute bleeding usually ceases when the torn vein clots or when the pressure developed by the enlarging clot exceeds the pressure of the bleeding vein. Bleeding may recur with further trauma, or, for reasons that are not clearly understood, the clot itself may enlarge in size over the ensuing several weeks following the initial incident.

4.2. Pathogenesis of Chronic SDH

The pathogenesis of chronic SDH has been controversial for more than a century, and still remains a matter of conjecture. The most prominent theory involves recurrent hemorrhage from a hematoma capsule and associated hyperfibrinolysis. It generally is believed that chronic SDHs form in the dural border cell layer of the hematoma cavity that then go on to form the characteristic outer and inner membranes. While there are few blood vessels in the inner membrane, which is derived mainly from the arachnoid, the outer membrane contains many fragile macrocapillaries (also called "sinusoidal vessels") that often are the source of repeated multifocal bleeding. This repeated hemorrhaging from the outer membrane thus is considered to be a causative factor for progressive enlargement of the hematoma.

Chronic SDH frequently is associated with increased fibrinolytic activity which destabilizes hemostatic clotting, resulting in a recurring hemorrhage and a hematoma capsule.

Normally, surfaces of serous cavities in the body absorb any foreign material when contact is made. Although the subdural space is not exactly like serous cavities elsewhere in the body, it generally is believed to behave similarly and thus, accumulation of blood, fibrin, and fibrin degradation products (FDP) within the subdural space may lead to either cellular organization with resorption of the subdural collection or to the development of a gradually enlarging SDH. Low cerebral counterpressure, a subdural collection that is too large, or physiological brain atrophy may be causative factors for slow, progressive enlargement of a chronic SDH. The dura border cells usually organize the hematoma during the second week or later, proliferate, and produce a neomembrane (outer and inner membranes), and eventually the hematoma is transfixed by collagen and elastic fibers and sprouting capillaries (sinusoidal vessels). These Vessels are fragile and are known to bleed easily. The inner surface of the hematoma develops its own pseudomembrane, separating the clot from the arachnoid. As a result, the neomembrane remains exceptionally vulnerable to traction as long as proliferative changes continue. Although an increase in collagen would reinforce the neomembrane and culminate in fibrotic healing of the lesion, a vicious cycle may develop in which minor trauma as well as fibrinolytic activity in the hematoma fluid triggers further proliferation of the dural border cells and bleeding from the fragile sinusoidal new blood vessels in the outer membrane, resulting in the formation of more neomembrane, bleeding into the SDH and expansion of the SDH.

Histological investigations of the outer hematoma membrane have demonstrated the considerable proliferation potential and fragility of the numerous macrocapillaries. The most characteristic clinicopathological aspect of the outer membrane of a chronic SDH seems to be its tendency to undergo repetitive, multi focal bleeding from the macrocapillaries. The general characteristics of the endothelial cells of the macrocapillaries are a large lumen, attenuated or flattened endothelial cells, scarce cytoplasmic interdigitations, less intimate cellular junctions, gap junctions, and thinness or absence of the basement membrane. These traits suggest that macrocapillaries are very fragile, susceptible to bleeding, and lead to an abnormally high vascular permeability. The number and extent of gaps between endothelial cells, ranging in size from 0.6 μm to 8 μm, suggest that they could account for most of the leakage, not only into the tissue of the outer membrane, but also into the hematoma cavity. Some studies have suggested that adjacent endothelial cells temporarily may become separated, allowing erythrocytes, as well as plasma, to escape from the lumen of the macrocapillaries. The mechanism by which endothelial gaps form is not completely understood; elevated intraluminal hydrostatic pressure or endothelial contractions could induce separation of adjacent endothelial cells, and/or perivascular leakage of blood substances from macrocapillaries with such endothelial gaps and an incomplete basement membrane could contribute to enlargement of a chronic SDH.

Additionally, some studies have suggested that the growth content of experimentally induced chronic SDH was proportional to the thickness of the layer of macrocapillaries and to the degree of leakage. Some studies have indicated that the pathogenesis of chronic SDH enlargement resulted from direct hemorrhaging of the macrocapillaries, exudation of persinusoidal edematous fluid into the hematoma cavity, and/or ruptures of small hemorrhagic cavities formed in the outer membranes.

4.3. Classification of the Chronic SDHs

Several classification schemes of chronic SDHs have been proposed. Nomura (Nomura, S., et al. J. Neurosurg, 81: 910-13, 1994) suggested a classification scheme based on CT scanning (high density, isodensity, low density, mixed density, and layering type of hematoma). Nakaguchi (Nakaguchi, H., et al. J. Neurosurg. 95: 256-62, 2001) defined four neuroimaging groups of hematomas based on CT scanning: 1) homogenous density type; 2) laminar type, defined as a subtype of homogenous density, with a high density layer along the inner membrane; 3) layering or separated type, containing two components of different densities with a boundary lying between them; and 4) trabecular density type, in which a high-density septum between the inner and the outer membranes appeared against a low-density to isodense background. Frati (J. Neurosurg. 100: 24-32, 2004) proposed a combination of Nomura's and Nakaguchi's classification schemes that classified the hematomas into four different groups: Group 1, the separated or layering type; Group 2, the laminar or mixed-density type; Group 3, the trabecular type (classified by Nomura within the group of mixed-density hematomas); and Group 4, a high-density, low-density, or isodense type described by Nomura, which also is defined as the homogeneous-density type by Nakaguchi.

4.4. Biomarkers for Chronic SDH

Some studies have suggested that the pathophysiology of chronic SDH is similar to that of an inflammatory response. According to one theory, after trauma, and once the subdural space has been created, CSF or blood collects within the dural border cell layer. Blood collection may be caused by the tearing of bridging veins subsequent to trauma. In elderly patients, as a result of brain atrophy, both the dural border cell layer and the bridging veins are stretched and can be damaged very easily by a traumatic event. Once this intradural space has been created, cells in the dural border begin to proliferate, representing the first step in the pathogenesis of chronic SDH. Mesenchymal cells proliferate, differentiate, and form an external or outer membrane (a sort of inflammatory capsule or membrane) around the blood clots or CSF. The outer membrane of the chronic SDH is composed of a sort of granulation tissue in which several types of inflammatory cells (mast cells, eosinophils, neutrophils, monocytes, macrophages, endothelial cells, and fibroblasts) are activated and recruited continuously. This membrane also contains immature vessels and connective tissue fibers and, on the whole, constitutes a source of inflammatory, angiogenic, fibrinolytic, and coagulation factors.

Immunohistochemical analysis has demonstrated expression of the cytokine VEGF in inflammatory cells infiltrating the neomembranes of chronic SDH, mainly in plasma cells and tissue macrophages. Some studies, which have examined VEGF's role in neovascularization and vascular hyperpermeability, suggest that inflammation is responsible for angiogenesis (meaning the physiological process involving the growth of new blood vessels from pre-existing vessels) of the outer membrane. Thus, after trauma, the sequence of events in the natural course of chronic SDH comprises local inflammation, angiogenesis, vascular leakage or permeability (due to immature neovessels), bleeding, hypercoagulative activity, hyperfibrinolytic activity, and ongoing vascular permeability (due to bradykinin, which is activated by plasmin from high-molecular-weight kininogen). This leads to further inflammation caused by the release of proinflammatory factors such as cytokines and bradykinin, creating a self-enhancing vicious circle that is responsible for frequent rebleeding and enlargement of the chronic SDH. Accordingly, some suggest that the biomarkers IL-6 and IL-8 may be appropriate for study of chronic SDH.

Generally, IL-6 and IL-8 are markers of the inflammation process. IL-6 and IL-8 are produced by many different cell types, including stimulated monocytes, macrophages, fibroblasts, endothelial cells, T cells, B-lymphocytes, granulocytes, smooth muscle cells, eosinophils, chondrocytes, osteoblasts, mast cells, and glial cells.

Briefly, IL-6 influences immune and inflammatory responses and is one of the major physiological mediators of the acute phase reaction. During inflammation in the nervous system, very high levels of IL-6 frequently can be observed in the CSF of patients with bacterial or viral meningitis, as well as in those harboring gliomas. The role of IL-8 in the inflammatory process is well established. IL-8 differs from all other cytokines in its specific ability to enhance adhesion molecule affinity on neutrophil granulocytes, activate them, and mediate their chemotaxis. Further, IL-8 supports angiogenesis and may play a role in angiogenesis-dependent processes such as granulation tissue, wound healing and tumor growth.

Chronic SDH generally presents some of the features of chronic inflammatory processes. In the hematoma, IL-6 and IL-8 are secreted by fibroblasts and by endothelial and inflammatory cells that infiltrate the outer membrane. Production of IL-6 and IL-8 is increased by proinflammatory factors that are released after bleeding, such as platelet-activating factor, bradykinin, and thrombin.

4.5. Need for Chronic SDH Treatments and Model Systems

Putative risk factors for chronic SDH'include age; alcoholism; medical diseases such as liver dysfunction, kidney diseases, diabetes, dementia, or coagulopathy; hemodialysis; usage of anticoagulant agents, antiplatelet agents, or chemotherapeutic agents; the presence of a cerebrospinal fluid shunt or of otherwise treated hydrocephalus; postoperative drainage of cerebrospinal fluid; and/or other causes for a decrease in size of the brain in relation to the fixed size of the cranium. The appearance of a chronic SDH on CT or magnetic resonance images (MRI) (layering hematoma compared to other types) and the method of treatment of a chronic SDH (burr hole, craniotomy, and twist drill trephination with or without irrigation) may influence the development of chronic SDH. Chronic SDH is a common disease in elderly persons and its incidence is highest (58 per 100,000 individuals) in persons older than 65 years of age. In approximately 60% to 80% of cases, a mild traumatic event is reported to have preceded the hemorrhage; however, a mild traumatic episode may sometimes go unrecognized. These putative risk factors for recurrence have been discussed in several reports in which controversial findings are not uncommon.

Surgery is the treatment of choice for chronic SDH. Several different modalities of surgery have been suggested: craniotomy, burr hole with or without irrigation and/or closed drainage system, and twist drill trephination directly into the hematoma at the site of its maximum thickness. However, concomitant diseases associated with chronic SDH can impair both its prognosis and surgical outcome. Further, the rate of recurrence of chronic SDH after surgery is between 3.7% and 30%. Recurrence increases the chance of death and morbidity from a chronic SDH.

The lack of an accurate and reproducible model system SDH chronic SDH has impaired efforts to research and develop new therapeutics and therapeutic methods for preventing the recurrence of chronic SDH. Prior attempts to develop animal models for chronic SDH have presented significant limitations, including, but not limited to, a lack of reproducibility.

5. Coagulation

Hemostasis is the cessation of blood loss from a damaged vessel. Platelets first adhere to macromolecules in the subendothelial regions of the injured blood vessel; they then aggregate to form the primary hemostatic plug. Platelets stimulate local activation of plasma coagulation factors, leading to generation of a fibrin clot that reinforces the platelet aggregate. Later, as wound healing occurs, the platelet aggregate and fibrin clot are degraded (Goodman & Gilman's The Pharmacological Basis of Therapeutics, Joel G. Hardman and Lee E. Limbird, Eds, McGraw-Hill, 2001, p. 1519-20).

Coagulation involves a series of zymogen activation reactions. At each stage, a precursor protein, or zymogen, is converted to an active protease by cleavage of one or more peptide bonds in the precursor molecule. The components that can be involved at each stage include a protease from the preceding stage, a zymogen, a nonenzymatic protein cofactor, calcium ions, and an organizing surface that is provided by the damaged blood vessel and platelets in vivo. The final protease to be generated is thrombin (factor IIa).

Fibrinogen is a 330,000 dalton protein that consists of three pairs of polypeptide chains (designated $\alpha$, $\beta$ and $\gamma$) covalently linked by disulfide bonds. Thrombin converts fibrinogen to fibrin monomers (Factor IA) by cleaving fibrinopeptides A (16 amino acid residues) and B (14 amino acid residues) from the amino-terminal ends of the $\alpha$ and $\beta$ chains respectively. Removal of the fibrinopeptides allows the fibrin monomers to form a gel. Initially, the fibrin monomers are bound to each other noncovalently. Subsequently, factor XIIIa catalyzes an interchain transglutamination reaction that cross-links adjacent fibrin monomers to enhance the strength of the clot.

Fibrin participates in the both the activation of Factor XIII by thrombin and activation of plasminogen activator (t-PA). Fibrin specifically binds the activated coagulation factors factor Xa and thrombin and entraps them in the network of fibers, thus functioning as a temporary inhibitor of these enzymes which stay active and can be released during fibrinolysis. Recent research has shown that fibrin plays a key role in the inflammatory response.

The protease zymogens involved in coagulation include factors II (prothrombin), VII, IX, X, XI, XII, and prekallikrein. Factors V and VIII are homologous 350,000 dalton proteins. Factor VIII circulates in plasma bound to von Willebrand factor, while factor V is present both free in plasma and as a component of platelets. Thrombin cleaves V and VIII to yield activated factors (Va and VIIIa) that have at least 50 times the coagulant activity of the precursor forms. Factors Va and VIIIa have no enzymatic activity themselves, but serve as cofactors that increase the proteolytic efficiency of Xa and IXa, respectively. Tissue factor (TF) is a nonenzymatic lipoprotein cofactor that greatly increases the proteolytic efficiency of VIIa. It is present on the surface of cells that are not normally in contact with plasma (e.g. fibroblasts and smooth muscle cells) and initiates coagulation outside a broken blood vessel.

Two pathways of coagulation are recognized: the intrinsic coagulation pathway so called because all of the components are intrinsic to plasma, and an extrinsic coagulation pathway. The extrinsic and intrinsic systems converge to activate the final common pathways causing fibrin formation. FIG. 6 shows an illustrative representation of the classic coagulation cascades. It generally is recognized that these systems function together and interact in vivo.

The extrinsic system (tissue factor pathway) generates a thrombin burst and is initiated when tissue thromboplastin activates factor VII. Upon vessel injury, TF is exposed to the blood and enzyme coagulation factor VII (proconvertin) circulating in the blood. Once bound to TF, FVII is activated to FVIIa by different proteases, including thrombin (factor IIa), factor Xa, IXa, XIIa and the FVIIa-IF complex itself. The FVIIa-TF complex activates factors IX and X. The activation of FXa by FVIIa-TF almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including FV and FVIII (which activates FXI, which, in turn, activates FIX), and activates and releases FVIII from being bound to vWF (von Willebrand Factor). FVIIa and FIXa together they form the "tenase" complex, which activates FX, and so the cycle continues.

The intrinsic system (contact activation pathway) is initiated when blood contacts any surface except normal endothelial and blood cells. The intrinsic system begins with formation of the primary complex on collagen by high-molecular weight kininogen (HMWK), prekallikrein, and FXII (Hageman factor). Prekallikrein is converted to kallikrein and FXII becomes FXIIa. FXIIa converts FXI into FXIa. Factor XIa activates FIX, which, with its co-factor FVIIIa form the tenase complex, which activates FX to FXa.

As currently understood, coagulation in vivo is a 3-step process centered on cell surfaces. FIG. 7 shows an illustration of the cell-surface based model of coagulation in vivo (Monroe Arterioscler Thromb Vase Biol. 2002; 22:1381-1389). In the first step, coagulation begins primarily by initiation with tissue factor, which is present on the subendothelium, tissues not normally exposed to blood, activated monocytes and endothelium when activated by inflammation. Factors VII and VIIa bind to tissue factor and adjacent collagen. The factor VIIa-tissue factor complex activates factor X and IX. Factor Xa activates factor V, forming a prothrombinase complex (factor Xa, Va and calcium) on the tissue factor expressing cell. In the second step, coagulation is amplified as platelets adhere to the site of injury in the blood vessel. Thrombin is activated by platelet adherence and then acts to fully activate platelets, enhance their adhesion and to release factor V from the platelet a granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin. Propagation, the third step, and is a combination of activation of the prothrombinase complexes that allow large amounts of thrombin to be generated from prothrombin. More platelets can be recruited, as well as activation of fibrin polymers and factor XIII.

Natural Anticoagulant Mechanisms

Platelet activation and coagulation normally do not occur within an intact blood vessel. Thrombosis (meaning a pathological process in which a platelet aggregate and/or a fibrin clot occludes a blood vessel) is prevented by several regulatory mechanisms that require a normal vascular endothelium. Prostacyclin ($PGI_2$), a metabolite of arachidonic acid synthesized by endothelial cells, inhibits platelet aggregation and secretion. Antithrombin is a plasma protein that inhibits coagulation factors of the intrinsic and common pathways. Heparan sulfate proteoglycans synthesized by endothelial cells stimulate the activity of antithrombin. Protein C is a plasma zymogen homologous to Factors II, VII, IX, and X. Activated protein C in combination with its nonenzymatic cofactor (Protein S) degrades cofactors Va and VIIIa and thereby greatly diminishes the rate of activation of prothrombin and factor X. Protein C is activated by thrombin only in the presence of thrombomodulin, an integral membrane protein of endothelial cells. Like antithrombin, protein C appears to exert an anticoagulant effect in the vicinity of intact endothelial cells. Tissue factor pathway inhibitor (TFPI), which is found in the lipoprotein fraction of plasma, when bound to factor Xa, inhibits factor Xa and the factor VIIa-tissue factor complex.

Fibrinolysis

The degradation of fibrin is termed "fibrinolysis." The fibrinolytic system dissolves intravascular clots as a result of the action of plasmin, an enzyme that digests fibrin. Plasminogen, an inactive precursor, is converted to plasmin by cleavage of a single peptide bond. Plasminogen (EC 3.4.21.7; PLG) degrades many blood plasma proteins, including fibrin clots.

The fibrinolytic system is regulated such that unwanted fibrin thrombi are removed, while fibrin in wounds persists to maintain hemostasis. FIG. 8 is an illustrative scheme of fibrinolytic pathways (Meltzer, et al. Seminars Thrombosis Hemostasis 2009, 35: 469-77). The serine protease tissue plasminogen activator (t-PA) is released from endothelial cells in response to various signals, including stasis produced by vascular occlusion. It is cleared rapidly from blood or inhibited by circulating inhibitors (plasminogen activator inhibitor-1 and plasminogen activator inhibitor-2), and thus exerts little effect on circulating plasminogen. tPA binds to fibrin and converts plasminogen, which also binds to fibrin, to plasmin. Plasminogen and plasmin bind to fibrin at binding sites located near their N-termini that are rich in lysine (Lys, K) residues. These sites also are required for binding of plasmin to the inhibitor $\alpha_2$-antiplasmin. $\alpha_2$-antiplasmin forms a stable complex with plasmin, thereby inactivating it. Thus, fibrin-bound plasmin is protected from inhibition (Goodman & Gilman's The Pharmacological Basis of Therapeutics, Joel G. Hardman and Lee E. Limbird, Eds, McGraw-Hill, 2001, p. 1531-32].

Plasminogen contains high affinity, amino-terminal lysine-containing binding sites that mediate the binding of plasminogen (or plasmin) to fibrin; this enhances fibrinolysis. These sites are in the amino-terminal secondary structure motifs (known as "kringles") that bind specifically to lysine and arginine residues of fibrin(ogen); when converted from plasminogen to plasmin, plasmin functions as a serine protease by cutting the chain of amino acids C-terminal to these lysine and arginine residues. Thus, plasmin action on a clot initially creates nicks in the fibrin and further digestion leads to solubilization. These sites also promote formation of complexes of plasmin with α2-antiplasmin, the major physiological plasmin inhibitor.

6. Anti-Fibrinolytic Agents

"Antifibrinolytic agents" (meaning agents used to prevent dissolution of a fibrin clot) have been used in treatment of some bleeding disorders. These agents, typically lysine analogs, are effective inhibitors for enzymes involved in the fibrinolytic pathway. Aprotonin (bovine pancreatic trypsin inhibitor, or BPTI, sold commercially as Trasylol™), a bovine protein that inhibits plasmin, which has been used to reduce bleeding during surgery, has been associated with fatal anaphylaxis when administered to humans.

6.1. Aminocaproic Acid

Aminocaproic acid (AMICAR, 6-aminohexanoic acid, ε-aminocaproic acid) is a derivative and analog of the amino acid lysine (Lys, K), and an effective inhibitor for enzymes that bind lysine residues.

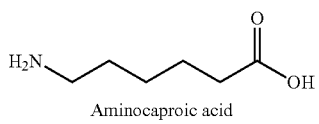
Aminocaproic acid

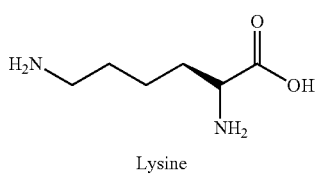
Lysine

AMICAR reversibly binds to the kringle domain (an autonomous protein domain that folds into large loops stabilized by 3 disulfide linkages) of plasminogen. By doing so, it prevents activation of plasminogen by its activators to plasmin, and prevents action of plasmin on fibrin.

AMICAR is useful in enhancing hemostasis when fibrinolysis contributes to bleeding. Fibrinolytic bleeding frequently may be associated with surgical complications following heart and other types of surgery (with or without cardiac bypass procedures) and portacaval shunt; hematological disorders such as amegakaryotic thrombocytopenia (accompanying aplastic anemia); acute and life-threatening abruptio placente; hepatic cirrhosis; ruptured intracranial aneurysms; intracerebral and SDH; and neoplastic disease, such as carcinoma of the prostate, lung, stomach and cervix. Urinary fibrinolysis, usually a normal physiological phenomenon, may contribute to excessive urinary tract fibrinolytic bleeding associated with surgical hematuria (following prostatectomy and nephrectomy) or nonsurgical hematuria (accompanying polycystic or neoplastic diseases of the genitourinary system).

AMICAR inhibits both the action of plasminogen activators and to a lesser degree, plasmin activity. Inhibition of fibrinolysis by AMICAR may theoretically result in clotting or thrombosis. Some studies have indicated an increased incidence of certain neurological deficits, such as hydrocephalus, cerebral ischemia, or cerebral vasospasm associated with the use of antifibrinolytic agents in the treatment of subarachnoid hemorrhage (SAH). Drug relatedness remains unclear but one theory is that these complications are due to promotion of thrombosis due to these drugs. Accordingly, it is advised that AMICAR should not be administered with Factor IX complex concentrates or with anti-inhibitor coagulant concentrates, as the risk of thrombosis may be increased.

6.2. Tranexamic Acid

Tranexamic acid (Cyklokapron®, Transamin®, Espercil®), a synthetic derivative of lysine, is a competitive inhibitor of plasminogen activation, and at much higher concentrations, a noncompetitive inhibitor of plasmin.

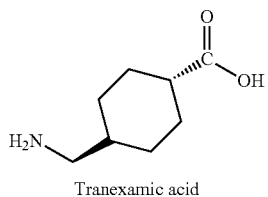
Tranexamic acid

It is about 10-fold more potent in vitro than AMICAR. Tranexamic acid binds more strongly than AMICAR to both the strong and weak receptor sites of the plasminogen molecule in a ratio corresponding to the difference in potency between the compounds.

Transexamic acid is used as a first-line nonhormonal treatment of dysfunctional uterine bleeding, heavy bleeding associated with uterine fibroids, and as a second-line treatment to factor VIII in hemophilia.

6.3. Factor VII

Recombinant activated factor VIIa is approved for use in hemophilia (with inhibitors) in North America and in Europe. Factor VII acts locally at sites of tissue injury and vascular-wall disruption by binding to tissue factor, thus generating small amounts of thrombin sufficient to activate platelets. At pharmacological doses, Factor VII directly activates factor X on the surface of activated platelets, resulting in a thrombin burst and acceleration of coagulation (Mayer, S. et al., NEJM, 2008, 358:2127-2138).

6.4. Aprotinin

Aprotinin, a bovine protein composed of 58 amino acid residues with a molecular weight of 6,512 Daltons, was isolated due to its kallikrein and trypsin inhibiting effect in the 1930s and is in clinical use since 1959. By inhibiting fibrinolysis and preserving platelet function, aprotinin was shown to reduce blood loss and transfusion requirements in cardiac surgery, lung, and liver transplantations and in surgery for hip replacement. Further disease related indications are hyperfibrinolytic hemostatic disorders and complications of thrombolytic therapies. The most common commercially available preparations are Trasylol™ (Bayer AG, Leverkusen, Germany) and Antagosan™ (Aventis Pharma, Frankfurt/M, Germany) (Beierlein, W. et al., Ann. Thorac. Surg., 2005, 79:741-748)

Due to its anti-fibrinolytic action, aprotinin is added to fibrin sealants in order to achieve hemostasis even when fibrinolytic activity is increased. Ready-to-use fibrin sealant kits have been commercially available in Europe since 1974 and in the United States since 1998. The most common kits are Beriplast™ (Centeon, Marburg, Germany), Tissucol/Tisseel™ (Baxter Hyland Immuno Division, Vienna, Austria), and Hemaseel™ (Hemacure, Montreal, Canada). TachoComb™ (Nycomed, Roskilde, Denmark), a hemostatic solid equine collagens fleece, also contains a small amount of aprotinin. (Beierlein, W. et al., Ann. Thorac. Surg., 2005, 79:741-748)

7. Drug Delivery from Bioresorbable Polymers

The combination of biodegradable polymers with a drug or pharmaceutically-active compound may allow a formulation that, when injected or inserted into body, is capable of sustained release of the drug.

Site-specific activity generally results if the location in the body into which the formulation is deposited is a fluid-filled space or some type of cavity, such as, for example, the sub-arachnoid space, the subdural cavity of a chronic SDH or the cavity left after the surgical evacuation of a hematoma, tumor or vascular malformation in the brain. This provides high concentrations of the drug at the site where activity is needed, and lower concentrations in the rest of the body, thus decreasing the risk of unwanted systemic side effects.

Site-specific delivery systems, for example, include use of microparticles (of about 1 µm to about 100 µm in diameter), thermoreversible gels (for example, PGA/PEG), and biodegradable polymers (for example, PLA, PLGA) that may be in the form of a film.

The delivery characteristics of the drug and the polymer degradation in vivo also can be modified. For example, polymer conjugation can be used to alter the circulation of the drug in the body and to achieve tissue targeting, reduce irritation and improve drug stability.

While all these possibilities exist, no one has applied such polymers to deliver therapeutic agents locally within the human brain to treat hemorrhagic brain conditions.

The described invention provides therapeutic compositions, methods for identifying therapeutic agents for treating hemorrhagic conditions of the brain, methods for treating hemorrhagic conditions of the brain, and an accurate and reproducible model system for chronic SDH and for ICH.

SUMMARY

According to one aspect, the described invention provides a method for treating hematoma expansion or recurrent bleeding resulting from a hemorrhagic condition in brain, the method comprising: (a) providing a pharmaceutical composition comprising (i) a therapeutically effective amount of an anti-fibrinolytic agent and (ii) a pharmaceutically acceptable carrier; (h) administering the pharmaceutical composition into or at a distance proximal to the hematoma in brain; and (c) improving patient outcome. According to one embodiment, the hemorrhagic condition results from traumatic brain injury (TBI). According to another embodiment, the hemorrhagic condition is rebleeding following a surgical evacuation of a hematoma. According to another embodiment, the hemorrhagic condition is a chronic subdural hematoma. According to another embodiment, the hemorrhagic condition is an intracerebral hematoma. According to another embodiment, the intracerebral hematoma is a spontaneous intracerebral hematoma. According to another embodiment, the intracerebral hematoma is a traumatic intracerebral hematoma According to another embodiment, the hemorrhagic condition is rebleeding following a craniotomy procedure. According to another embodiment, the craniotomy procedure is performed for treating a brain cancer. According to another embodiment, the craniotomy procedure is performed for treating a vascular malformation in the brain. According to another embodiment, the craniotomy procedure is performed for treating a brain aneurysm. According to another embodiment, the administration is an implantation. According to another embodiment, the anti-fibrinolytic agent is E-aminocaproic acid (AMICAR). According to another embodiment, the anti-fibrinolytic agent is Factor VII. According to another embodiment, the Factor VII is a recombinant Factor VII. According to another embodiment, the anti-fibrinolytic agent is tranexamic acid. According to another embodiment, the anti-fibrinolytic agent is aprotonin. According to another embodiment, the pharmaceutically acceptable carrier is a controlled-release carrier. According to another embodiment, the pharmaceutically acceptable carrier is a sustained-release carrier. According to another embodiment, the anti-fibrinolytic agent is embedded in the sustained-release carrier. According to another embodiment, the anti-fibrinolytic agent is coated on the sustained-release carrier. According to another embodiment, the sustained-release carrier releases the anti-fibrinolytic agent for at least 21 days post-administration. According to another embodiment, the sustained-release carrier releases the anti-fibrinolytic agent for about 3 to 5 days post-administration. According to another embodiment, the sustained-release carrier is a microparticle. According to another embodiment, the sustained-release carrier is a nanoparticle. According to another embodiment, the sustained-release carrier comprises a biodegradable polymer. According to another embodiment, the biodegradable polymer is a synthetic polymer. According to another embodiment, the biodegradable polymer is a naturally occurring polymer. According to another embodiment, the synthetic polymer is selected from the group consisting of a polyester, a polyester polyethylene glycol polymer, a polyamino-derived biopolymer, a polyanhydride, a polyorthoester, a polyphosphazene, a sucrose acetate isobutyrate (SAIB), a photopolymerizable biopolymer, and a combination thereof. According to another embodiment, the synthetic polymer is polyglyolic acid (PGA). According to another embodiment, the synthetic polymer is a copolymer of polyglycolic acid formed with trimethylene carbonate, polylactic acid (PLA), or polycaprolactonc. According to another embodiment, the sustained-release carrier is a hydrogel. According to another embodiment, the naturally occurring biopolymer is a protein polymer. According to another embodiment, the naturally occurring polymer comprises hyaluronic acid. According to another embodiment, the naturally occurring polymer comprises less than 2.3% of hyaluronic acid. According to another embodiment, the distance proximal to the hematoma is from about 0.5 mm to about 10 mm. According to another embodiment, the pharmaceutical composition exhibits a localized pharmacological effect. According to another embodiment, the pharmaceutical composition exhibits its pharmacological effect throughout the brain.

According to another aspect, the described invention provides a site-specific, sustained-release pharmaceutical composition for treating hematoma expansion or recurrent rebleeding resulting from a hemorrhagic condition in brain, the pharmaceutical composition comprising: (a) a therapeutically effective amount of an anti-fibrinolytic agent; and (b) a pharmaceutically acceptable carrier, wherein in the pharmaceutically acceptable carrier is a sustained-release carrier. According to another embodiment, the hemorrhagic condition is rebleeding following traumatic brain injury. According to another embodiment, the hemorrhagic condition is a chronic subdural hematoma. According to another embodiment, the hemorrhagic condition is an intracerebral hematoma. According to another embodiment, the intracerebral hematoma is a spontaneous intracerebral hematoma. According to another embodiment, the intracerebral hematoma is a traumatic intracerebral hematoma. According to another embodiment, the hemorrhagic condition is rebleeding following a craniotomy procedure. According to another embodiment, the craniotomy procedure is performed for treating a brain cancer. According to another embodiment, the craniotomy procedure is performed for treating a vascular malformation in brain. According to another embodiment, the craniotomy procedure is performed for treating a brain aneurysm. According to another embodiment, the anti-fibrinolytic agent is $\epsilon$-aminocaproic acid (AMICAR). According to another embodiment, the anti-fibrinolytic agent is Factor VII. According to another embodiment, the Factor VII is a recombinant Factor VII. According to another embodiment, the anti-fibrinolytic agent is tranexamic acid. According to another embodiment, the anti-fibrinolytic agent is aprotonin. According to another embodiment, the pharmaceutically acceptable carrier is a controlled-release carrier. According to another embodiment, the pharmaceutically acceptable carrier is a sustained-release carrier. According to another embodiment, the anti-fibrinolytic agent is embedded in the sustained-release carrier. According to another embodiment, the anti-fibrinolytic agent is coated on the sustained-release carrier. According to another embodiment, the sustained-release carrier releases the anti-fibrinolytic agent for at least 21 days post-administration. According to another embodiment, the sustained-release carrier releases the anti-fibrinolytic agent for about 3 to 5 days post-administration. According to another embodiment, the sustained-release carrier comprises a microparticle. According to another embodiment, the sustained-release carrier comprises a nanoparticle. According to another embodiment, the sustained-release carrier comprises a biodegradable polymer. According to another embodiment, the biodegradable polymer is a synthetic polymer. According to another embodiment, the biodegradable polymer is a naturally occurring polymer. According to another embodiment, the synthetic polymer is selected from the group consisting of a polyester, a polyester polyethylene glycol polymer, a polyamino-derived biopolymer, a polyanhydride, a polyorthoester, a polyphosphazene, a sucrose acetate isobutyrate (SAIB), a photopolymerizable biopolymer, and a combination thereof. According to another embodiment, the synthetic polymer is polyglyolic acid (PGA). According to another embodiment, the synthetic polymer is a copolymer of polyglycolic acid formed with trimethylene carbonate, polylacitic acid (PLA), or polycaprolactone. According to another embodiment, the sustained-release carrier is a hydrogel. According to another embodiment, the naturally occurring polymer is a protein polymer. According to another embodiment, the protein polymer is synthesized from self-assembling protein polymers. According to another embodiment, the naturally occurring polymer is a naturally occurring polysaccharide. According to another embodiment, the naturally occurring polymer comprises a hyaluronic acid. According to another embodiment, the naturally occurring polymer comprises less than 2.3% of hyaluronic acid.

DETAILED DESCRIPTION OF THE INVENTION

Glossary

Figure 1:
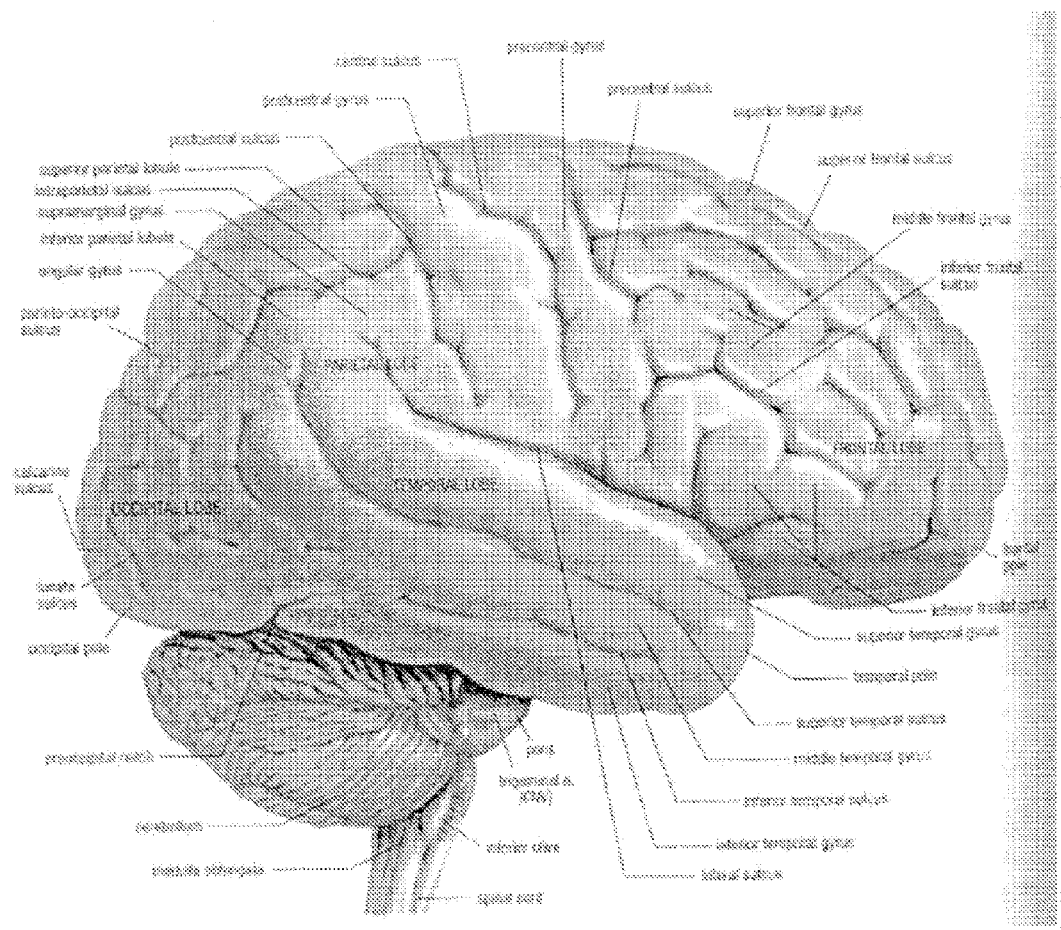
FIG. 1 shows an illustrative lateral view of the human brain (Stedman's Medical Dictionary, 27$^{th}$ Edition, plate 7 at A7 (2000)).
Figure 2:
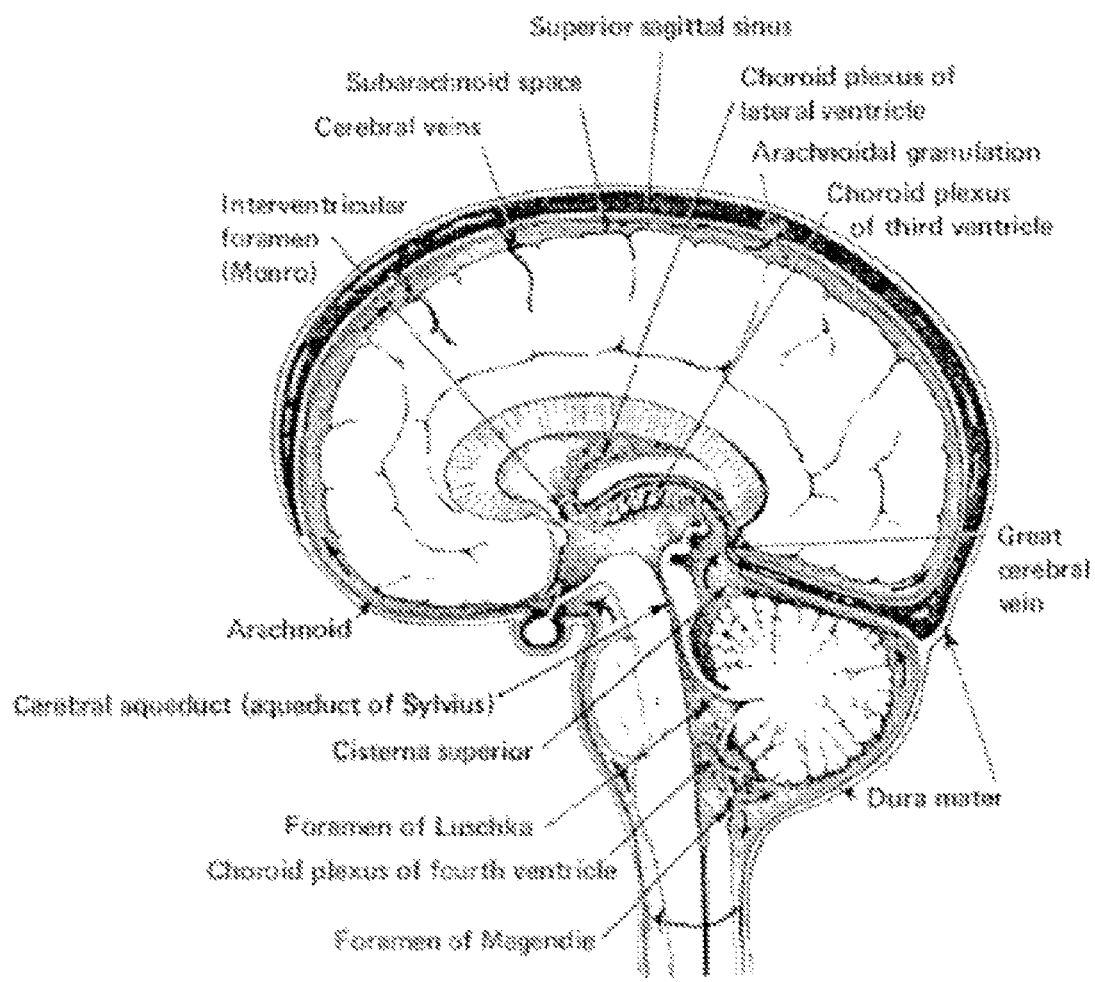
FIG. 2 shows an illustrative sagittal view of the human brain (Correlative Neuroanatomy & Functional Neurology, 18$^{th}$ Ed., p. 46 (1982)).
Figure 3:
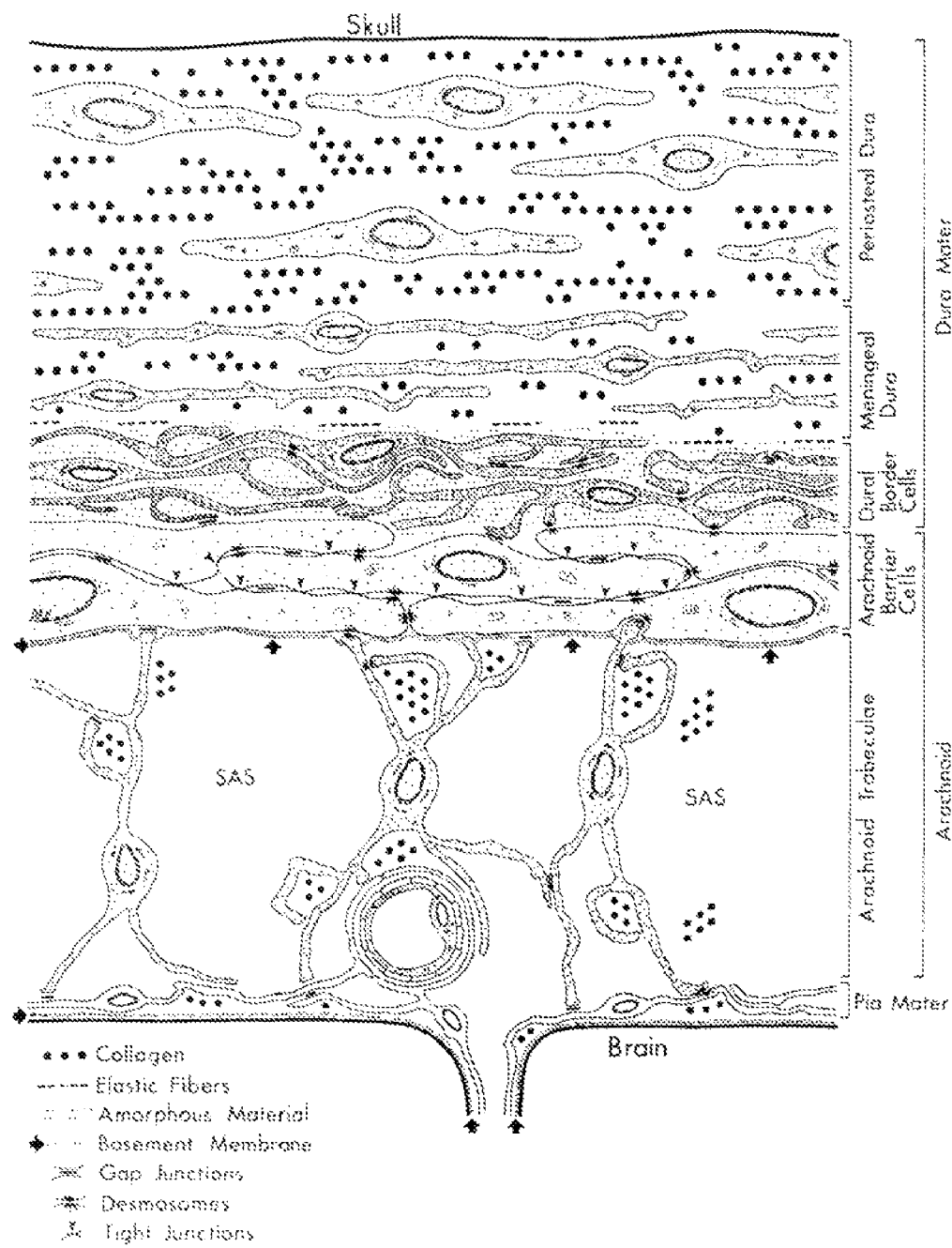
FIG. 3 shows an illustrative view of a cross section of the intact meninges from the inner surface of the skull (upper) to the external surface of the brain (lower). Collagen is present in the periosteal and meningeal dura (large dots, orientation of fibrils not indicated) and in the subarachnoid space (SAS), usually in folds of trabecular cells. The dural border cell layer has no extracellular collagen, few cell junctions, enlarged extracellular spaces (but no basement membrane), and fibroblasts that are distinct from those of the outer portions of the dura. The arachnoid harrier cell layer has essentially no extracellular space, numerous cell junctions, more plump appearing cells, and a comparatively continuous basement membrane on its surface toward the SAS. Note the continuity of cell layers from the arachnoid to the dura (no intervening space), the characteristic appearance of the arachnoid trabeculae, and the relationship of the pia (from Haines D E: On the question of subdural space. Anat Rec 230:3-21, 1991).
Figure 4:
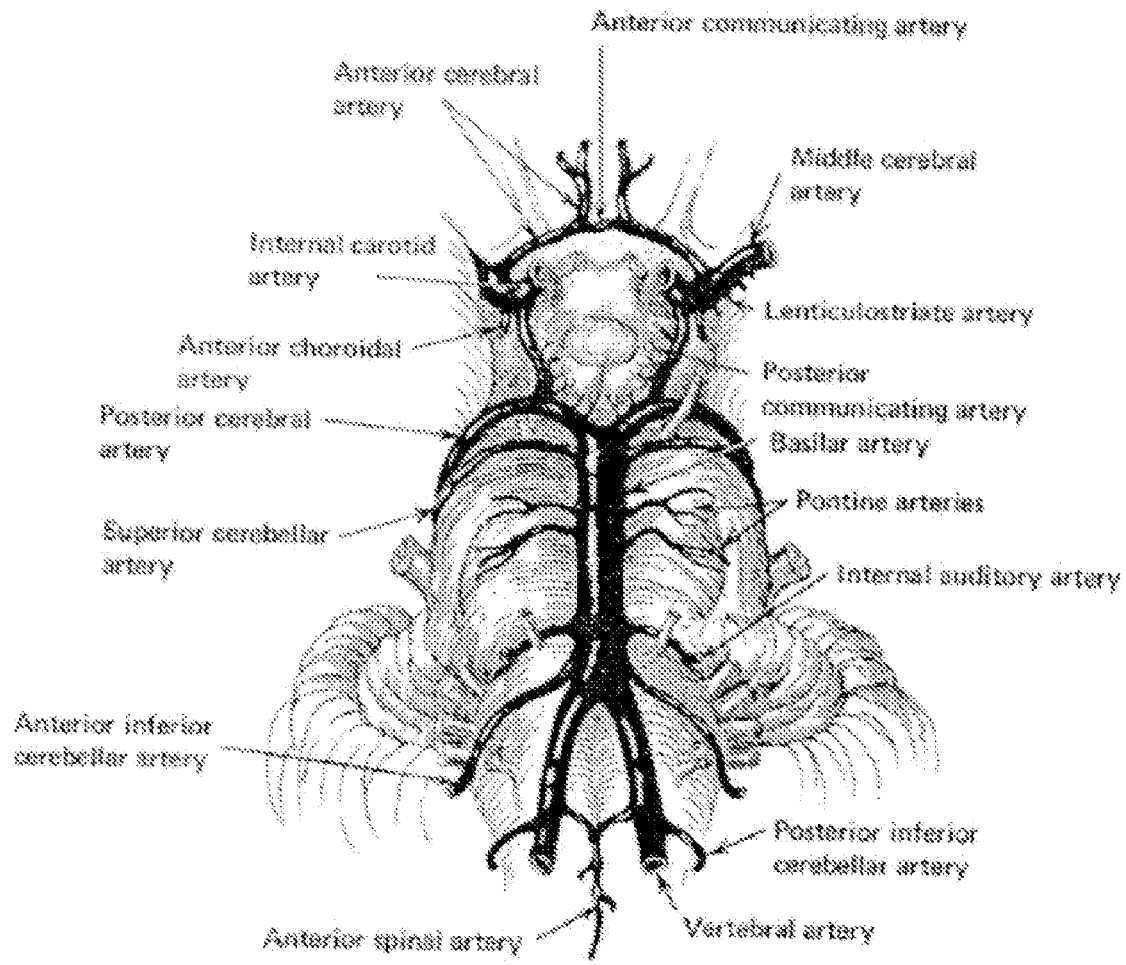
FIG. 4 shows an illustrative view of the circle of Willis and principal arteries of the brain (Correlative Neuroanatomy & Functional Neurology, 18$^{th}$ Ed., p. 48 (1982)).
Figure 5:
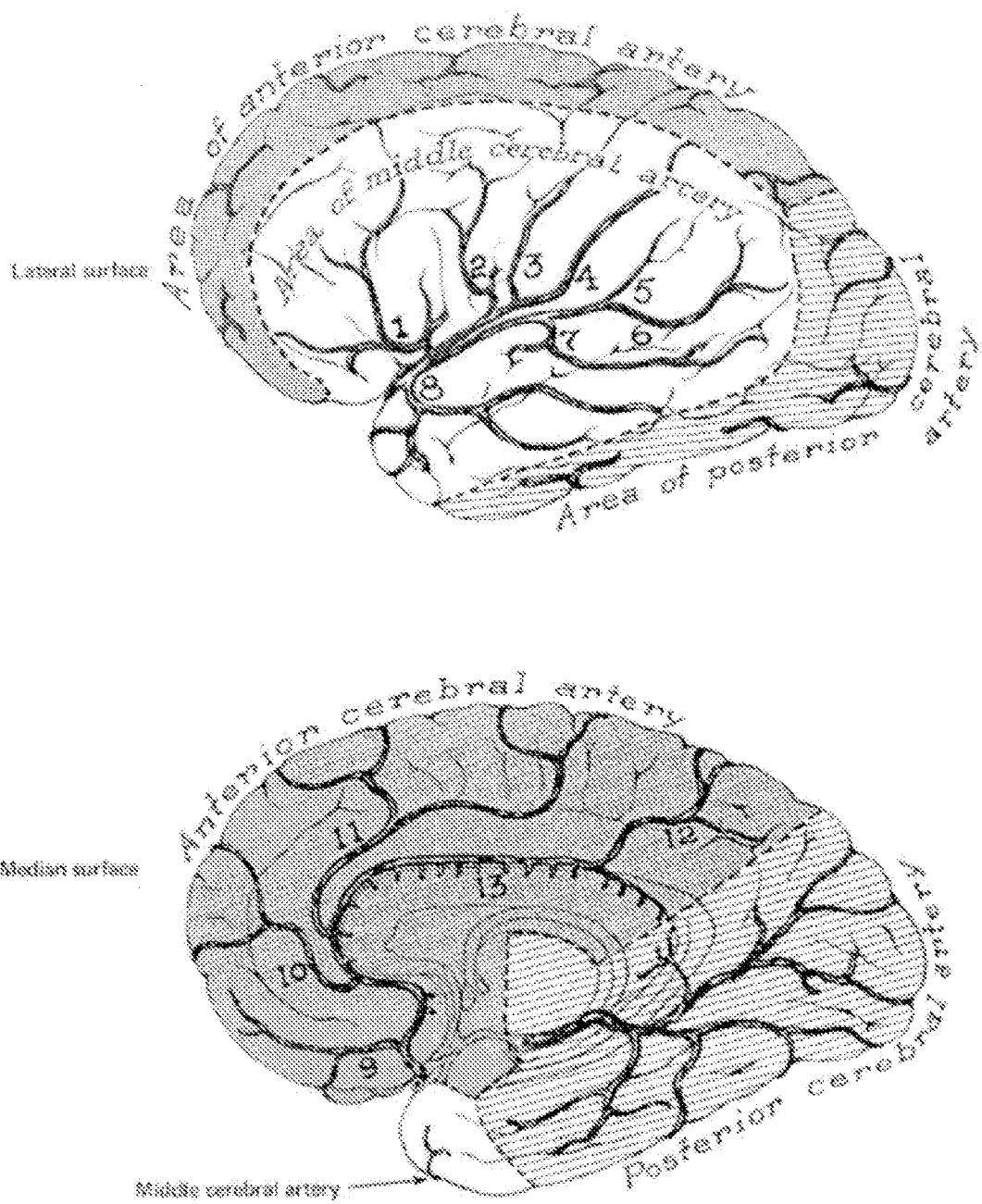
FIG. 5 shows an illustrative view of the arterial supply of the cerebral cortex. 1: orbitofrontal artery; 2: prerolandic artery; 3: rolandic artery; 4: anterior parietal artery; 5: posterior parietal artery; 6: angular artery; 7: posterior temporal artery; 8: anterior temporal artery; 9: orbital artery; 10: frontopolar artery; 11: callosomarginal artery; 12: posterior internal frontal artery; 13: pericallosal artery. (Correlative Neuroanatomy & Functional Neurology, 18$^{th}$ Ed., p. 50 (1982)).
Figure 6:
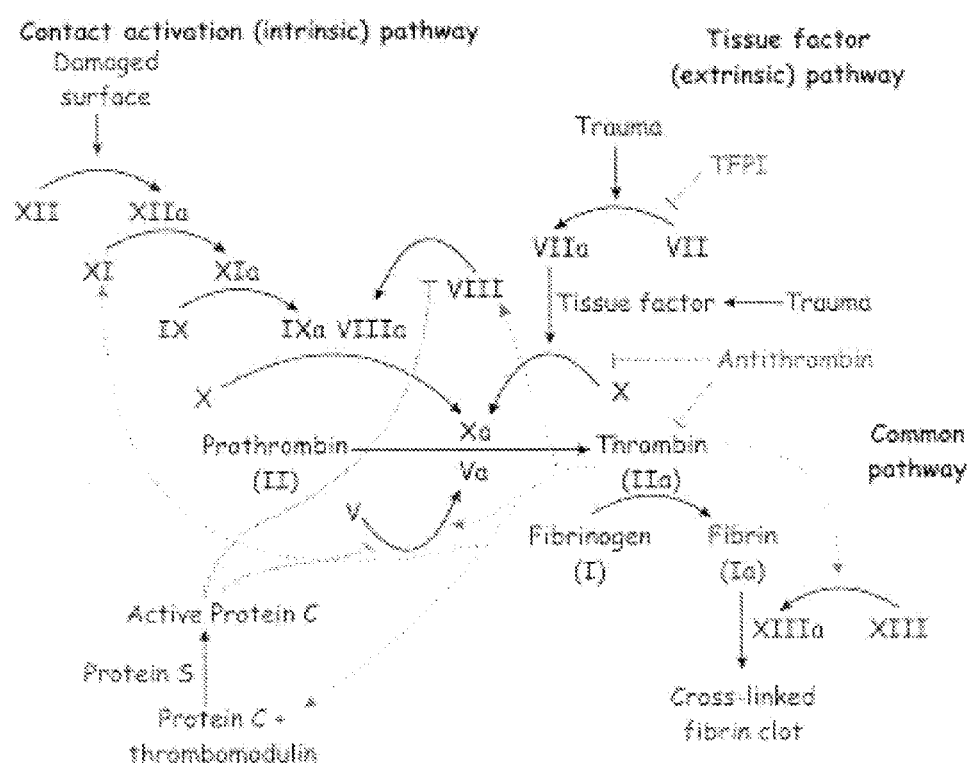
FIG. 6 is an illustrative scheme of the coagulation cascade.
Figure 7:
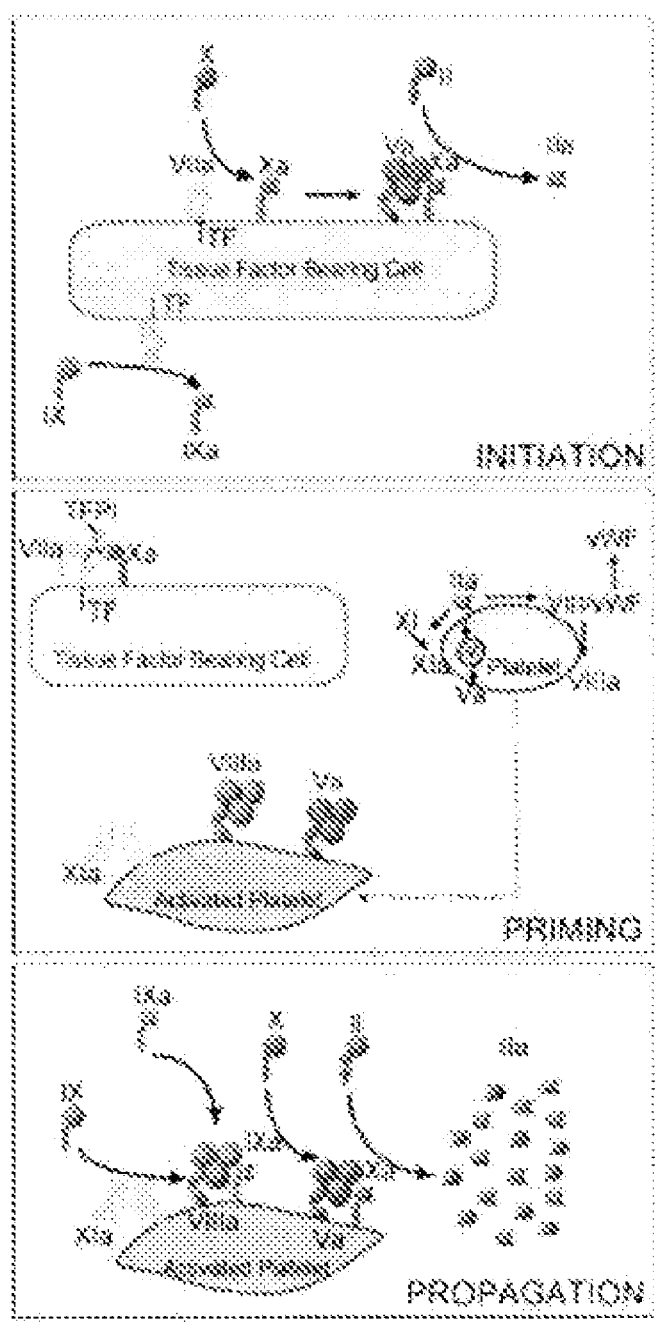
FIG. 7 is an illustration of the cell-surface based model of coagulation in vivo (Monroe Arterioscler Thromb Vase Biol. 2002; 22:1381-1389).
Figure 8:
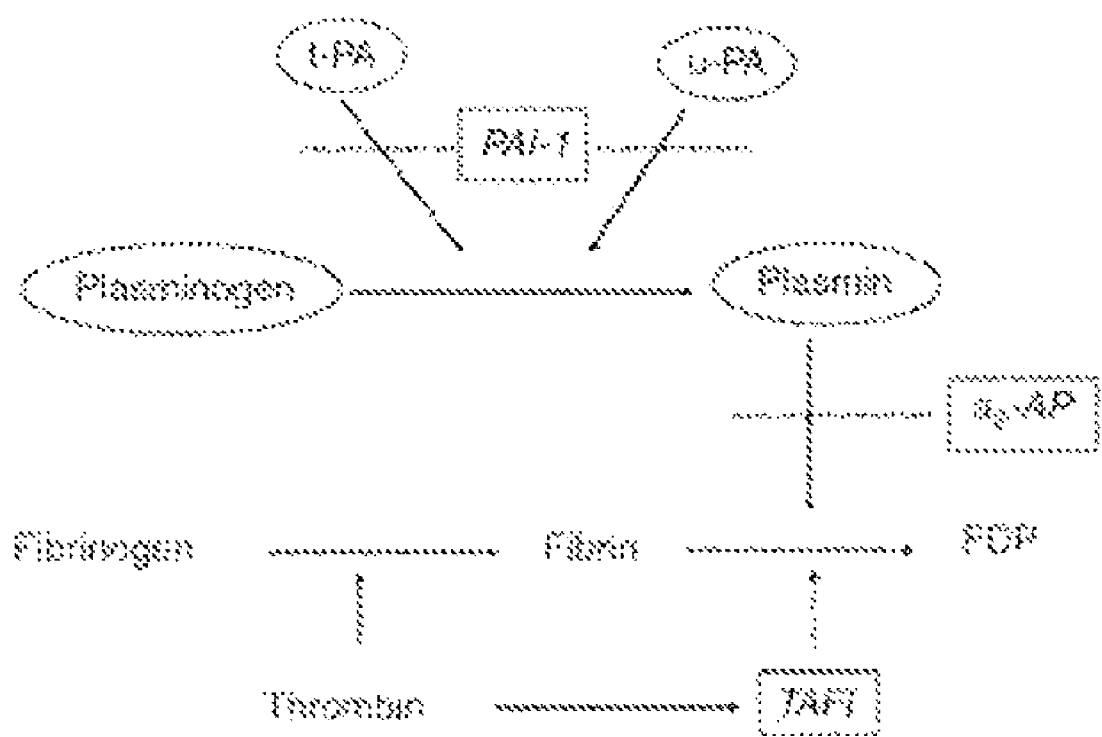
FIG. 8 is an illustrative scheme of fibrinolytic pathways (Meltzer, Seminars Thrombosis Hemostasis 2009, 35: 469-77).

Anatomical Terms:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "active" as used herein refers to having pharmacological or biological activity or affect. The term "active ingredient" ("AI", "active pharmaceutical ingredient", "API", or "bulk active") is the substance in a drug that is pharmaceutically active. As used herein, the phrase "additional active ingredient" refers to an agent, other than a compound of the described composition, that exerts a pharmacological, or any other beneficial activity.

The term "administer" as used herein means to give or to apply. The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "allogeneic" as used herein refers to being genetically different although belonging to or obtained from the same species.

The term "analog" as used herein refers to a compound having a structure similar to another, but differing from it, for example, has one or more atoms, functional groups, or substructure.

The term "antagonist" as used herein refers to a substance that counteracts the effects of another substance.

As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes chimeric antibodies and wholly synthetic antibodies, and fragments thereof.

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels.

Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy ($V_H$) and light ($V_\kappa$ and $V_\lambda$) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (WI) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

The term "antifibrinolytic agent" as used herein refers to an agent used to prevent or dissolve a fibrin clot. Antifibrinolytic agents are effective inhibitors for enzymes involved in the fibrinolytic pathway and typically include lysine analogs.

The term "antigen" and its various grammatical forms refers to any substance that can stimulate the production of antibodies and can combine specifically with them. The terms "epitope" and "antigenic determinant" are used interchangeably herein to refer to an antigenic site on a molecule that an antibody combining site (ACS) recognizes and to which that antibody binds/attaches itself. A given epitope may be primary, secondary, or tertiary-sequence related. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

An "antiplasma" is defined as a plasma which can be obtained after immunizing a mammal or human with antigens. It is obtained by separating the corpuscular components from whole blood.

An "antiserum" is the liquid phase of blood recovered after clotting has taken place obtained from an immunized mammal, including humans.

"Anesthetic agents" refers to agents that result in a reduction or loss of sensation. Non-limiting examples of anesthetic drugs that are suitable for use in the context of the present invention include pharmaceutically acceptable salts of lidocaine, bupivacaine, chiorprocaine, dibucaine, etidocaine, mepivacaine, tetracaine, dyclonine, hexylcaine, procaine, cocaine, ketamine, pramoxine and phenol.

The term "aneurysm" as used herein means an abnormal dilation of a blood vessel, either an artery or vein, in the body, which may occur at any time during the life of the organism.

The term "autologous" as used herein means derived from the same organism.

The term "biocompatible" as used herein refers to causing no clinically relevant tissue irritation, injury, toxic reaction, or immunological reaction to living tissue.

The term "biodegradable" as used herein refers to material that will break down actively or passively over time by simple chemical processes, by action of body enzymes or by other similar biological activity mechanisms.

The term "brain cancer" as used herein refers to neoplasms, which initiate in the brain or metastatic brain cancer, which starts somewhere else in the body and moves to the brain. The term "brain cancer" as used herein include both benign and malignant cancer cells.

The term "carrier" as used herein describes a material that does not cause significant irritation to an organism and does not abrogate the biological activity and properties of the compound of the composition of the described invention. Carriers must be of sufficiently high purity and of sufficiently low toxicity to render them suitable for administration to the mammal being treated. The carrier can be inert, or it can possess pharmaceutical benefits. The terms "excipient". "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "chemotherapeutic agent, in its most general sense, refers to a chemical substance or drug useful in the treatment or control of a disease. The term "cisterna" as used herein means a cavity or enclosed space serving as a reservoir.

The term "compatible" as used herein refers to the components of a composition are capable of being combined with each other in a manner such that there is no interaction that would substantially reduce the efficacy of the composition under ordinary use conditions.

The term "component" as used herein refers to a constituent part, element or ingredient.

The term "condition", as used herein, refers to a variety of health states and is meant to include disorders or diseases caused by any underlying mechanism or disorder, injury, and the promotion of healthy tissues and organs.

The term "contact" and all its grammatical forms as used herein refers to a state or condition of touching or of immediate or local proximity The term "controlled release" is intended to refer to any drug-containing formulation in which the manner and profile of drug release from the formulation are regulated. This refers to immediate as well as non-immediate release formulations, with non-immediate release formulations including, but not limited to, sustained release and delayed release formulations.

The term "craniotomy" as used herein refers to a surgical removal of a section of a bone (e.g., bone flap) from the skull for the purpose of operating on the underlying tissues.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type 1 cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "derivative" as used herein means a compound that may be produced from another compound of similar structure in one or more steps. A "derivative" or "derivatives" of a compound retains at least a degree of the desired function of the compound. Accordingly, an alternate term for "derivative" may be "functional derivative."

The term "disease" or "disorder", as used herein, refers to an impairment of health or a condition of abnormal functioning.

The term "drug" as used herein refers to a therapeutic agent or any substance, other than food, used in the prevention, diagnosis, alleviation, treatment, or cure of disease.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "fossa" as used herein means a small cavity or depression, as in a bone.

The term "hematoma" as used herein refers to a localized mass of extravasated blood that has escaped the confines of a blood vessel that is present within surrounding tissue that is relatively or completely confined within an organ, tissue, space, or potential space.

The term "hematoma expansion" as used herein refers to an increase in volume, size, quantity, or scope of a hematoma.

The term "hemorrhagic condition" as used herein refers to a disorder or disease in which there is abnormal bleeding.

The term "hydrate" as used herein refers to a compound formed by the addition of water or its elements to another molecule. The water usually can split off by heating, yielding the anhydrous compound.

The term "hydrogel" as used herein refers to a substance resulting in a solid, semisolid, pseudoplastic, or plastic structure containing a necessary aqueous component to produce a gelatinous or jelly-like mass.

The term "hydrophilic" as used herein refers to a material or substance having an affinity for polar substances, such as water.

The terms "in the body", "void volume". "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "injury," as used herein, refers to damage or harm to a structure or function of the body caused by an outside agent or force, which may be physical or chemical.

The term "interleukin" as used herein refers to a cytokine secreted by white blood cells as a means of communication with other white blood cells.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). Stereoisomers may include, but are not limited to, L/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images. The invention provides for each pure stereoisomer of any of the compounds described herein. Such stereoisomers may include enantiomers, diastereomers, or E or Z alkene, imine or oxime isomers. The invention also provides for stereoisomeric mixtures, including racemic mixtures, diastereomeric mixtures, or E/Z isomeric mixtures. Stereoisomers can be synthesized in pure form (Nógrádi, M.; Stereoselective Synthesis, (1987) VCH Editor Ebel, H. and Asymmetric Synthesis, Volumes 3-5, (1983) Academic Press, Editor Morrison, J.) or they can be resolved by a variety of methods such as crystallization and chromatographic techniques (Jaques, J.; Collet, A.; Wilen, S.; Enantiomer, Racemates, and Resolutions, 1981, John Wiley and Sons and Asymmetric Synthesis, Vol. 2, 1983, Academic Press, Editor Morrison, J). In addition the compounds of the described invention may be present as enantiomers, diasteriomers, isomers or two or more of the compounds may be present to form a racemic or diastereomeric mixture.

The term "labile" as used herein refers to subject to increased degradation.

The term "lipophilic" as used herein refers to preferring or possessing an affinity for a non-polar environment compared to a polar or aqueous environment.

The term "long-term" release, as used herein, means that the implant is constructed and arranged to deliver therapeutic levels of the active ingredient for at least 7 days, and potentially up to about 30 to about 60 days.

The term "minimizing progression" as used herein refers to reducing the amount, extent, size, or degree of development of a sequence or series of events.

The term "modulate" as used herein means to regulate, alter, adapt, or adjust to a certain measure or proportion. Such modulation may be any change, including an undetectable change.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "particles" as used herein refers to an extremely small constituent, e.g., nanoparticles or microparticles) that may contain in whole or in part at least one therapeutic agent as described herein.

The term "improving patient outcome" as used herein refers to an absence of or diminutionf at least one side effect associated with the systemic administration of an anti-fibrinolytic agent. Examples of side effects include, but are not limited to, hypotension, cardiac arrythmias, edema, rhabdomyolysis, thrombosis, cerebral infarction or stroke and myocardial infarction or heart attack.

The term "pharmaceutical composition" is used herein to refer to a composition that is employed to prevent, reduce in intensity, cure or otherwise treat a target condition or disease.

As used herein the phrase "pharmaceutically acceptable carrier" refers to any substantially non-toxic carrier useable for formulation and administration of the composition of the described invention in which the product of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The term "periosteum" as used herein refers to the normal investment of bone, consisting of a dense, fibrous outer layer, to which muscles attach, and a more delicate, inner layer capable of forming bone.

The term "prevent" as used herein refers to the keeping, hindering or averting of an event, act or action from happening, occurring, or arising.

The term "prodrug" as used herein means a peptide or derivative which is in an inactive form and which is converted to an active form by biological conversion following administration to a subject.

The term "solvate" as used herein refers to a complex formed by the attachment of solvent molecules to that of a solute. The term "solvent" refers to a substance capable of dissolving another substance (termed a "solute") to form a uniformly dispersed mixture (solution).

The term "recombinant" as used herein refers to a substance produced by genetic engineering.

The term "reduced" or "to reduce" as used herein refer to a diminution, a decrease, an attenuation or abatement of the degree, intensity, extent, size, amount, density or number.

The term "similar" is used interchangeably with the terms analogous, comparable, or resembling, meaning having traits or characteristics in common.

The term "sinus" and its various grammatical forms means an expanded area in a canal or tube.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent. A "suspension" is a dispersion (mixture) in which a finely-divided species is combined with another species, with the former being so finely divided and mixed that it doesn't rapidly settle out. In everyday life, the most common suspensions are those of solids in liquid. Among the acceptable vehicles and solvents that may be employed are water, Ringer's solution, and isotonic sodium chloride solution.

The term "susceptible" as used herein refers to a member of a population at risk.

The terms "subject" or "individual" or "patient" are used interchangeably to refer to a member of an animal species of mammalian origin, including humans.

The phrase "a subject having a subdural hematoma" refers to a subject who presents with diagnostic markers and symptoms associated with a SDH.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. Nonlimiting examples of sustained release biodegradable polymers include polyesters, polyester polyethylene glycol copolymers, polyamino-derived biopolymers, polyanhydrides, polyorthoesters, polyphosphazenes, SAIB, photopolymerizable biopolymers, protein polymers, collagen, polysaccharides, chitosans, and alginates.

The term "symptom" as used herein refers to a phenomenon that arises from and accompanies a particular disease or disorder and serves as an indication of it.

The term "syndrome," as used herein, refers to a pattern of symptoms indicative of some disease or condition.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "therapeutically effective amount" or an "amount effective" of one or more of the active agents is an amount that is sufficient to provide the intended benefit of treatment. An effective amount of the active agents that can be employed ranges from generally 0.1 mg/kg body weight and about 50 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a surgeon using standard methods.

The term "thickeners" as used herein refer to agents that make the composition of the described invention dense or viscous in consistency.

The term "transgenic" as used herein refers to an experimental strain of an animal that has been genetically engineered in the laboratory such that a specific exogenous gene is added to or deleted from the RNA of the animal. Common transgenic animal models include, but are not limited to, the mouse.

Traumatic brain injury (TBI) is caused by a head injury that can result in lasting damage to the brain and affects up to 10 million patients worldwide each year. The health effects of TBI can be debilitating, result in long term disability, and have significant financial burdens.

Traumatic brain injury is caused by an external mechanical force, such as a blow to the head, concussive forces, acceleration-deceleration forces, or a projectile. It may occur both when the skull fractures and the brain is directly penetrated (open head injury) and also when the skull remains intact but the brain still sustains damage (closed head injury).

Symptoms of a TBI range in severity, depending on the extent of damage to the brain, and may include headaches, neck pain, confusion, difficulty remembering, concentrating, or making decisions, dizziness, fatigue, mood changes, nausea, irritability, photophobia, blurred vision, ringing in the ears, loss of sense of taste or smell, seizures, sleep disturbances, hypoxemia, hypotension and brain swelling.

TBI is graded as mild (meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=1), motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TRI (GCS 9-13) the patient is lethargic or stuporous, and in severe injury (GCS 3-8) the patient is comatose, unable to open his or her eyes or follow commands.

Patients with severe TBI (comatose) have a significant risk of hypotension, hypoxaemia, and brain swelling. If these sequelae are not prevented or treated properly, they can exacerbate brain damage and increase the risk of death.

The term "traumatic intracerebral hemorrhage" (ICH) as used herein refers to such bleeding that is caused, caused by, or associated with traumatic injury.

The term "treat" or "treating" includes abrogating; substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "topical" refers to administration of a composition at, or immediately beneath, the point of application. The phrase "topically applying" describes application onto one or more surfaces(s) including epithelial surfaces. Although topical administration, in contrast to transdermal administration, generally provides a local rather than a systemic effect. The terms "topical administration" and "transdermal administration" as used herein unless otherwise stated or implied, are used interchangeably.

The term "whole blood" as used herein refers to generally unprocessed or unmodified collected blood containing all of its components, including, but are not limited to, plasma, cellular components (e.g., red blood cells, white blood cells (including lymphocytes, monocytes, eosinophils, basophils, and neutrophils), and platelets), proteins (e.g., fibrinogen, albumin, immunoglobulins), hormones, coagulation factors, and fibrinolytic factors. The term "whole blood" is inclusive of any anticoagulant that may be combined with the blood upon collection.

The term "vascular malformation" as used herein refers to an abnormality in the development of blood vessels within the brain that result in an abnormal collection or pattern of blood vessels.

The term "xenogeneic" as used herein refers to being of different species.

I. Non-Human Animal Model for a Hemorrhagic Brain Condition

According to one aspect, the described invention provides a non-human animal model system for a hemorrhagic brain condition. According to some such embodiments, the hemorrhagic brain condition is a chronic SDH. According to some such embodiments, the hemorrhagic brain condition is an ICH. According to one embodiment, the non-human animal model system provides for administration to a mammal of an initiating agent composition to induce the hemorrhagic brain condition.

According to another aspect, the described invention provides a mammal having an inducible hemorrhagic brain condition, resulting in a hematoma. According to some such embodiments, the hemorrhagic brain condition is a chronic SDH. According to some such embodiments, the hemorrhagic brain condition is an ICH. According to some embodiments, the hematoma remains stable over time. According to some embodiments, the hematoma enlarges over time. According to some embodiments, the enlargement of the hematoma is progressive.

According to some embodiments, the mammal is a mouse. According to another embodiment, the mammal is a transgenic mouse. According to another embodiment, the mammal is a rat. According to another embodiment, the mammal is a member of the order Rodentia.

According to another embodiment, the initiating agent composition is administered into the subcutaneous space of the mammal.

According to another embodiment, an initiating agent composition is administered intracranially. According to some embodiments, the initiating agent composition is administered in proximity to the dura mater of a mammal. According to some embodiments, the initiating agent composition is administered by surgical injection. According to some embodiments, the initiating agent composition is deposited on or in an implant.

According to another embodiment, the initiating agent composition comprises fluid obtained from a chronic SDH. According to another embodiment, the initiating agent composition comprises autologous blood, or a component thereof. According to another embodiment, the initiating agent composition comprises allogeneic blood, or a component thereof. According to another embodiment, the initiating agent composition comprises xenogeneic blood, or a component thereof. According to another embodiment, the initiating agent composition comprises an antibody against at least one blood coagulation factor. According to another embodiment, the initiating agent composition comprises an enzyme that catalyzes the breakdown of collagen, such as collagenase. According to another embodiment, the initiating agent composition comprises an antibody against at least one blood coagulation factor selected from the group consisting of a procoagulant, an anti-coagulant, a clot structure factor, a fibrinolysis factor and a phospholipid. According to another embodiment, the procoagulant is selected from the group consisting of blood coagulation factor II, factor V, factor VII, factor IX, factor X, factor XI, factor XII, prekallikrein, kininogen and tissue factor. According to another embodiment, the anticoagulant is selected from the group consisting of protein C, protein S, antithrombin III, and heparin cofactor II.

According to another embodiment, the clot structure factor is selected from the group consisting of fibrinogen and factor XIII. According to another embodiment, the fibrinolysis factor is selected from the group consisting of plasminogen, tissue-type plasminogen activator, plasminogen activator inhibitor and α2-plasmin inhibitor. According to another embodiment, the initiating agent composition for inducing a chronic SDH in the non-human animal model comprises whole blood. According to some embodiments, the whole blood is autologous. According to some embodiments, the whole blood is allogeneic. According to some embodiments, the whole blood is xenogeneic. According to some such embodiments, the blood is of a volume of about 1 µl to about 20 ml. According to some such embodiments, the blood is of a volume of about 100 µl to about 15 ml. According to some such embodiments, the blood is of a volume of about 500 µl to about 12.5 ml. According to some such embodiments, the blood is of a volume of about 1 ml to about 10 ml. According to some such embodiments, the volume of blood is about 2 ml. According to some such embodiments, the volume of blood is about 3 ml. According to some such embodiments, the volume of blood is about 4 nil. According to some such embodiments, the volume of blood is about 5 ml. According to some such embodiments, the volume of blood is about 6 ml. According to some such embodiments, the volume of blood is about 7 ml. According to some such embodiments, the volume of blood is about 8 ml. According to some such embodiments, the volume of blood is about 9 ml. According to some such embodiments, the initiating agent composition comprises at least one component of whole blood. Examples of components of whole blood include, but are not limited to, plasma, cellular components (e.g., red blood cells, white blood cells (including lymphocytes, monocytes, eosinophils, basophils, and neutrophils), and platelets), proteins (e.g., fibrinogen, albumin, immunoglobulins), hormones, coagulation factors, and fibrinolytic factors.

According to another embodiment, the initiating agent composition for inducing a hemorrhagic brain condition resulting in a hematoma in the non-human animal model comprises fluid obtained from a chronic SDH. According to some such embodiments, the fluid obtained from a chronic SDH is of a volume of about 1 µl to about 20 ml. According to some such embodiments, the fluid obtained from a chronic SDH is of a volume of about 100 µl to about 15 ml. According to some such embodiments, the fluid obtained from a chronic SDH is of a volume of about 500 µl to about 12.5 ml. According to some such embodiments, the fluid obtained from a chronic SDH is of a volume of about 1 ml to about 10 ml. According to some such embodiments, the volume of the fluid obtained from a chronic SDH is about 2 ml. According to some such embodiments, the volume of the fluid obtained from a chronic SDH is about 3 ml. According to some such embodiments, the volume of the fluid obtained from a chronic SDH is about 4 ml. According to some such embodiments, the volume of the fluid obtained from a chronic SDH is about 5 ml. According to some such embodiments, the volume of the fluid obtained from a chronic SDH is about 6 ml. According to some such embodiments, the volume of the fluid obtained from a chronic SDH is about 7 ml. According to some such embodiments, the volume of the fluid obtained from a chronic SDH is about 8 ml. According to some such embodiments, the volume of the fluid obtained from a chronic SDH is about 9 ml.

According to another embodiment, the initiating agent composition for inducing a hemorrhagic brain condition resulting in a hematoma in the non-human animal model comprises an antibody.

According to another embodiment, the initiating agent composition for inducing the hemorrhagic brain condition resulting in a hematoma in the non-human animal model is a monoclonal antibody. According to another embodiment, the initiating agent for inducing the hemorrhagic brain condition resulting in al hematoma in the non-human animal model is a polyclonal antibody.

According to another embodiment, the initiating agent composition for inducing the hemorrhagic brain condition resulting in the hematoma in the non-human animal model comprises a monospecific antibody directed against one blood coagulation factor, or against a specific epitope of the blood coagulation factor. According to another embodiment, the initiating agent composition for inducing the hemorrhagic brain condition resulting in the hematoma in the non-human animal model comprises an antibody that recognizes at least two blood coagulation factors. For example, an initiating agent composition may comprise antibodies against human plasmin or human plasminogen that cross-react with animal-derived plasmin or plasminogen. Alternately, an initiating agent composition may comprise antibodies against human thrombin that cross-react with animal-derived thrombin. Alternately, the initiating agent composition may comprise antibodies against vitamin K-dependent blood factors, such as, for example, factors of the prothrombin complex.

According to other embodiments, the initiating agent composition comprises antibodies against at least one procoagulant (including, but not limited to, blood coagulation factors II, V, VII, IX, X, XI, XII, prekallikrein, kininogen and tissue factor), antibodies against anti-coagulants (including, but not limited to, protein C, protein S, antithrombin III, heparin cofactor II), clot structure factors (including, but not limited to, fibrinogen and factor XIII), fibrinolysis factors (such as, but not limited to, plasminogen, t-PA, PAI-1 and α2-plasmin inhibitor) and phospholipids.

The suitability of the antibody preparation for this purpose can be judged on the basis of various tests. For example, an in vitro test may be carried out in which an antibody preparation is incubated with a cerebral spinal fluid sample of a test animal, and the inhibition or elimination, of blood factor(s) is determined.

The desired effect of a changed recurrence of chronic SDH may be shown in a test animal in vivo by measuring the hematoma, or rate of formation or dissolution thereof.

According to some embodiments, the initiating agent composition may be prepared by immunizing a mammal with plasma, a plasma fraction, or a recombinant equivalent thereof, recovering the antiplasma or antiserum and subsequently absorbing one or several antibodies of the antiplasma or antiserum so that the initiating agent composition will contain only such functional antibodies that can selectively functionally inhibit and/or eliminate at least one blood factor in a mammal.

A method for preparing such an initiating agent composition comprises the following steps: (a) immunizing a mammal with plasma, a plasma fraction, or a recombinant equivalent thereof, (b) recovering the antiplasma or antiserum from the immunized animal of (a), (c) optionally purifying an antibody fraction from the antiplasma or antiserum of (a), and (d) formulating a composition suitable for infusion into or proximal to the dura mater, brain, or subcutaneous tissue of a mammal.

According to some embodiments, the initiating agent composition may be prepared by immunizing a mammal with fluid obtained from a human chronic SDH, a fraction of the fluid obtained from a human chronic SDH, or a recombinant equivalent thereof, recovering the antiplasma or antiserum, and subsequently purifying antibodies from the antiplasma or antiserum so that the initiating agent composition will contain only those functional antibodies that selectively can inhibit and/or eliminate at least one blood factor in a mammal.

A method for preparing such an initiating agent composition comprises the following steps: (a) immunizing a mammal with human chronic SDH fluid, a human chronic SDH fluid fraction, or a recombinant equivalent thereof, (b) recovering the antiplasma or antiserum from the immunized animal of (a), (c) optionally purifying an antibody fraction of the antiplasma or antiserum of (a), and (d) formulating a composition suitable for infusion into or proximal to the dura mater of a mammal.

According to another embodiment, the chronic SDH, or similar disorder, may be more precisely induced by preparing the initiating agent composition with antibodies specific for a certain blood factor that do not cross-react with other blood factors that may be contained in the material for immunization. Mammals in which immunization may be performed include, but are not limited to, sheep, goats, cows, pigs, rabbits, guinea pigs, horses, rats and mice. Mammals in which a chronic SDH may be induced include, but are not limited to, mice, rats, and other members of the order Rodentia.

According to another embodiment, the described invention provides methods for the use of antiplasma antibodies, for example in an infusion composition, for the treatment of a mammal as a model for a deficiency of blood factors by functionally inhibiting and/or eliminating several blood factors, so that the clotting time in vitro or ex vivo or the recurrence of chronic SDH in the mammal are changed. According to some embodiments, the antibodies against certain blood factors are absorbed in vivo by administering the blood factors to the animal.

According to some embodiments, a blood factor can be resubstituted and the changed clotting time and characteristics of the chronic SDH identified as being dependent upon the resubstituted blood factor.

According to another embodiment, the described invention further provides a method for determining characteristics of a recurrent chronic SDH, the method comprising the steps: (a) inducing a chronic SDH in a mammal; (b) collecting fluid obtained from the chronic SDH; (c) determining blood factor components of the fluid of step (b); and (d) determining the rate of expansion or decrease in size of the chronic SDH over time.

According to another embodiment, the initiating agent composition further comprises a carrier. According to another embodiment, the carrier is a pharmaceutical carrier. According to some embodiments, the initiating agent is in the form of a pharmaceutical composition.

According to another embodiment, the initiating agent composition is of an amount from about 0.000001 mg/kg body weight to about 10 g/kg body weight. According to another embodiment, the initiating agent composition is of an amount from about 0.000002 mg/kg body weight to about 10 g/kg body weight. According to another embodiment, the initiating agent composition is of an amount from about 0.000003 mg/kg body weight to about 10 g/kg body weight. According to another embodiment, the initiating agent composition is of an amount from about 0.000004 mg/kg body weight to about 10 g/kg body weight. According to another embodiment, the initiating agent composition is of an amount from about 0.000005 mg/kg body weight to about 10 g/kg body weight. According to another embodiment, the initiating agent composition is of an amount from about 0.000006 mg/kg body weight to about 10 g/kg body weight. According to another embodiment, the initiating agent composition is of an amount from about 0.000007 mg/kg body weight to about 10 g/kg body weight. According to another embodiment, the initiating agent composition is of an amount from about 0.000008 mg/kg body weight to about 10 g/kg body weight. According to another embodiment, the initiating agent composition is of an amount from about 0.000009 mg/kg body weight to about 10 g/kg body weight. According to another embodiment, the initiating agent composition is of an amount from about 0.00001 mg/kg body weight to about 10 g/kg body weight. According to another embodiment, the initiating agent composition is of an amount from about 0.00002 mg/kg body weight to about 10 g/kg body weight. According to another embodiment, the initiating agent composition is of an amount from about 0.0003 mg/kg body weight to about 10 g/kg body weight. According to another embodiment, the initiating agent composition is of an amount from about 0.00004 mg/kg body weight to about 10 g/kg body weight. According to another embodiment, the initiating agent composition is of an amount from about 0.00005 mg/kg body weight to about 10 g/kg body weight. According to another embodiment, the initiating agent composition is of an amount from about 0.00006 mg/kg body weight to about 10 g/kg body weight. According to another embodiment, the initiating agent composition is of an amount from about 0.00007 mg/kg body weight to about 10 g/kg body weight. According to another embodiment, the initiating agent composition is of an amount from about 0.00008 mg/kg body weight to about 10 g/kg body weight. According to another embodiment, the initiating agent composition is of an amount from about 0.00009 mg/kg body weight to about 10 g/kg body weight. According to another embodiment, the initiating agent composition is of an amount from about 0.0001 mg/kg body weight to about 10 g/kg body weight. According to another embodiment, the initiating agent composition is of an amount of about 0.0005 mg/kg body weight. According to another embodiment, the initiating agent composition is of an amount of about 0.001 mg/kg body weight. According to another embodiment, the initiating agent composition is of an amount of about 0.005 mg/kg body weight. According to another embodiment, the initiating agent composition is of an amount of about 0.01 mg/kg body weight. According to another embodiment, the initiating agent composition is of an amount of about 0.1 mg/kg body weight. According to another embodiment, the initiating agent composition is of an amount of about 1 mg/kg body weight. According to another embodiment, the initiating agent composition is of an amount of about 10 mg/kg body weight. According to another embodiment, the initiating agent composition is of an amount of about 20 mg/kg body weight. According to another embodiment, the initiating agent composition is of an amount of about 30 mg/kg body weight. According to another embodiment, the initiating agent composition is of an amount of about 40 mg/kg body weight. According to another embodiment, the initiating agent composition is of an amount of about 50 mg/kg body weight. According to another embodiment, the initiating agent composition is of an amount of about 60 mg/kg body weight. According to another embodiment, the initiating agent composition is of an amount of about 70 mg/kg body weight. According to another embodiment, the initiating agent composition is of an amount of about 80 mg/kg body weight. According to another embodiment, the initiating agent composition is of an amount of about 90 mg/kg body weight. According to another embodiment, the initiating agent composition is of an amount of about 100 mg/kg body weight. According to another embodiment, the initiating agent composition is of an amount of about 110 mg/kg body weight. According to another embodiment, the initiating agent composition is of an amount of about 120 mg/kg body weight. According to another embodiment, the initiating agent composition is of an amount of about 130 mg/kg body weight. According to another embodiment, the initiating agent composition is of an amount of about 140 mg/kg body weight. According to another embodiment, the initiating agent composition is of an amount of about 150 mg/kg body weight. According to another embodiment, the initiating agent composition is of an amount of about 160 mg/kg body weight. According to another embodiment, the initiating agent composition is of an amount of about 170 mg/kg body weight. According to another embodiment, the initiating agent composition is of an amount of about 180 mg/kg body weight. According to another embodiment, the initiating agent composition is of an amount of about 190 mg/kg body weight. According to another embodiment, the initiating agent composition is of an amount of about 200 mg/kg body weight. According to another embodiment, the initiating agent composition is of an amount of about 250 mg/kg body weight. According to another embodiment, the initiating agent composition is of an amount of about 500 mg/kg body weight.

II. Method for Evaluating Substance for Treating Hemorrhagic Conditions of Brain According to another aspect, the described invention provides a method for evaluating a substance for its ability to treat repeated hemorrhaging from hemorrhagic conditions of the brain in a mammal, the method comprising steps: (a) administering a substance to be evaluated to the mammal; and (b) measuring at least one clotting parameter, at least one fibrinolytic parameter (meaning one of a set of measurable factors) or a change in at least one parameter characteristic of a hemorrhagic condition in the mammal by the substance to be evaluated. Clotting parameters or fibrinolytic parameters may be determined according to known methods. For example, a series of in vitro examinations for testing blood clotting factors or fibrinolysis factors and their effect in samples are known.

According to some embodiments, the mammal is a mouse. According to another embodiment, the mammal is a knockout mouse. According to another embodiment, the mammal is a rat. According to another embodiment, the mammal is a member of the Order Rodentia.

According to one embodiment, the hemorrhagic condition of the brain is a chronic SDH. According to one embodiment, the method further comprises the step of treating a mammal with an initiating agent composition for inducing a chronic SDH. According to another embodiment, the initiating agent composition for inducing a chronic SDH in the non-human animal model comprises whole blood. According to some embodiments, the whole blood is autologous. According to some embodiments, the whole blood is allogeneic. According to some embodiments, the whole blood is xenogeneic. According to some such embodiments, the blood is of a volume of about 1 µl to about 20 ml. According to some such embodiments, the blood is of a volume of about 100 µl to about 15 ml. According to some such embodiments, the blood is of a volume of about 500 µl to about 12.5 ml. According to some such embodiments, the blood is of a volume of about 1 ml to about 10 ml. According to some such embodiments, the volume of blood is about 2 ml. According to some such embodiments, the volume of blood is about 3 ml. According to some such embodiments, the volume of blood is about 4 ml. According to some such embodiments, the volume of blood is about 5 ml. According to some such embodiments, the volume of blood is about 6 ml. According to some such embodiments, the volume of blood is about 7 ml. According to some such embodiments, the volume of blood is about 8 ml. According to some such embodiments, the volume of blood is about 9 ml. According to some such embodiments, the initiating agent composition comprises at least one component of whole blood. Examples of components of whole blood include, but are not limited to, plasma, cellular components (e.g., red blood cells, white blood cells (including lymphocytes, monocytes, eosinophils, basophils, and neutrophils), and platelets), proteins (e.g., fibrinogen, albumin, immunoglobulins), hormones, coagulation factors, and fibrinolytic factors.

According to another embodiment, administering step (a) i.e., administering a substance to be evaluated to the mammal, comprises administering an initiating agent composition to a rodent. According to some such embodiments, the initiating agent composition comprises 6-aminonicatinomide. According to some such embodiments, the dose of 6-aminonicatinomide is 0-10 mg/kg body weight. According to some such embodiments, the dose of 6-aminonicatinomide is 11-20 mg/kg body weight. According to some such embodiments, the dose of 6-aminonicatinomide is 21-30 mg/kg body weight.

According to another embodiment, the initiating agent composition for inducing a chronic SDH comprises fluid obtained from a human chronic SDH. According to some such embodiments, the fluid obtained from a human chronic SDH is of a volume of about 1 µl to about 20 ml. According to some such embodiments, the fluid obtained from a human chronic SDH is of a volume of about 100 µl to about 15 ml. According to some such embodiments, the fluid obtained from a human chronic SDH is of a volume of about 500 µl to about 12.5 ml. According to some such embodiments, the fluid obtained from a human chronic SDH is of a volume of about 1 ml to about 10 ml. According to some such embodiments, the fluid obtained from a human chronic SDH is about 2 ml. According to some such embodiments, the fluid obtained from a human chronic SDH is about 3 ml. According to some such embodiments, the fluid obtained from a human chronic SDH is about 4 ml. According to some such embodiments, the fluid obtained from a human chronic SDH is about 5 ml. According to some such embodiments, the volume of cerebral spinal fluid is about 6 ml. According to some such embodiments, the volume of cerebral spinal fluid is about 7 ml. According to some such embodiments, the volume of cerebral spinal fluid is about 8 ml. According to some such embodiments, the volume of cerebral spinal fluid is about 9 ml.

According to some embodiments, the initiating agent composition is in the form of a pharmaceutical composition. According to some embodiments, the initiating agent composition further comprises a carrier. According to some embodiments, the carrier is a pharmaceutical carrier.

According to another embodiment, the initiating agent composition for inducing a chronic SDH is an antibody. According to another embodiment, the initiating agent composition for inducing a chronic SDH is a monoclonal antibody. According to another embodiment, the initiating agent composition for inducing a chronic SDH is a polyclonal antibody. According to some embodiments, the initiating agent composition is an anti-plasma antibody preparation.

According to some embodiments, the initiating agent composition comprises antibodies against at least one procoagulant (including, but not limited to, blood coagulation factors II, V, VII, IX, X, XI, XII, prekallikrein, kininogen and tissue factor), antibodies against anti-coagulants (including, but not limited to, protein C, protein S, antithrombin ill, heparin cofactor II), clot structure factors (including, but not limited to, fibrinogen and factor XIII), fibrinolysis factors (such as, but not limited to, plasminogen, tissue-type plasminogen activator (t-PA), plasminogen activator inhibitor (PAI-1) and α2-plasmin inhibitor) and phospholipids.

According to some embodiments, a measurement of at least one parameter characteristic of the chronic SDH of a mammal with an induced chronic SDH is compared to a measurement of at least one parameter characteristic of the chronic SDH of a mammal which has been administered a compound or substance to be tested in order to determine the extent to which the substance to be tested can treat the induced chronic SDH. Examples of such a parameter include, but are not limited to, a bleeding behavior, a volume of blood in the chronic SDH, a size of the hematoma area, an expansion or a contraction of the hematoma area, expansion kinetics of the chronic SDH, and contraction kinetics of the chronic SDH. According to some embodiments, the compound or substance to be tested is administered prior to induction of the chronic SDH. According to some embodiments, the compound or substance to be tested is administered simultaneously with the initiating agent composition. According to some embodiments, the compound or substance to be tested is administered after induction of the chronic SDH.

According to another embodiment, the initiating agent composition is administered into a subcutaneous space of the dorsal surface of the mammal. According to another embodiment, the initiating agent composition is administered to the brain of a mammal. According to some such embodiments, the initiating agent composition is administered to the brain following craniotomy. According to some such embodiments, the initiating agent composition is administered to the brain by a burr hole. The term "craniotomy" as used herein refers to any bony opening that is cut into the skull. A section of skull, called a bone flap, is removed to access the brain underneath. There are many types of craniotomies, which are named according to the area of skull to be removed. According to some such embodiments, the burr hole is a frontal burr hole. According to some such embodiments, the burr hole is a parietal burr hole. According to some such embodiments, the burr hole is a temporal burr hole. According to some such embodiments, the burr hole is a suboccipital burr hole. Some common craniotomies include frontotemporal craniotomy, parietal craniotomy, temporal craniotomy, and suboccipital craniotomy. Typically the bone flap is replaced. According to some embodiments, stereotactic frames, image-guided computer systems, or endoscopes are used to direct instruments precisely through the burr hole.

No food or drink will permitted 8 hours before surgery. General anesthesia will be administered. Once asleep, the animal's head will be placed in a skull fixation device to hold the head in position during the procedure.

After the hair of the intended incision area is shaved and the scalp is prepared with an antiseptic, a skin incision will be made. The skin and muscles will be lifted off the bone and folded back. Next, one or more small burr holes will be made in the skull with a surgical drill. In some embodiments, a bone flap will be created. The cut bone flap will be lifted and removed to expose the dura. The bone flap will be safely stored until it is replaced at the end of the procedure. In some cases, a drain may be placed under the skin for a couple of days to remove blood or fluid from the surgical area. The muscles and skin will be sutured back together, and a soft adhesive dressing will be placed over the incision.

According to some embodiments, the initiating agent composition is administered intracranially. According to some such embodiments, the initiating agent composition is administered by perfusion. According to some such embodiments, the initiating agent composition is administered subdurally. According to some such embodiments, the initiating agent composition is administered intracerebrally. According to some such embodiments, the initiating agent composition is administered by surgical injection. According to some such embodiments, the initiating agent composition is deposited on or in an implant.

According to another embodiment, the initiating agent composition is of an amount from about 0.000001 mg/kg body weight to about 10 g/kg body weight. According to another embodiment, the initiating agent composition is of an amount from about 0.000002 mg/kg body weight to about 10 g/kg body weight. According to another embodiment, the initiating agent composition is of an amount from about 0.000003 mg/kg body weight to about 10 g/kg body weight. According to another embodiment, the initiating agent composition is of an amount from about 0.000004 mg/kg body weight to about 10 g/kg body weight. According to another embodiment, the initiating agent composition is of an amount from about 0.000005 mg/kg body weight to about 10 g/kg body weight. According to another embodiment, the initiating agent composition is of an amount from about 0.000006 mg/kg body weight to about 10 g/kg body weight. According to another embodiment, the initiating agent composition is of an amount from about 0.000007 mg/kg body weight to about 10 g/kg body weight. According to another embodiment, the initiating agent composition is of an amount from about 0.000008 mg/kg body weight to about 10 g/kg body weight. According to another embodiment, the initiating agent composition is of an amount from about 0.000009 mg/kg body weight to about 10 g/kg body weight. According to another embodiment, the initiating agent composition is of an amount from about 0.00001 mg/kg body weight to about 10 g/kg body weight. According to another embodiment, the initiating agent composition is of an amount from about 0.00002 mg/kg body weight to about 10 g/kg body weight. According to another embodiment, the initiating agent composition is of an amount from about 0.0003 mg/kg body weight to about 10 g/kg body weight. According to another embodiment, the initiating agent composition is of an amount from about 0.00004 mg/kg body weight to about 10 g/kg body weight. According to another embodiment, the initiating agent composition is of an amount from about 0.00005 mg/kg body weight to about 10 g/kg body weight. According to another embodiment, the initiating agent composition is of an amount from about 0.00006 mg/kg body weight to about 10 g/kg body weight. According to another embodiment, the initiating agent composition is of an amount from about 0.00007 mg/kg body weight to about 10 g/kg body weight. According to another embodiment, the initiating agent composition is of an amount from about 0.00008 mg/kg body weight to about 10 g/kg body weight. According to another embodiment, the initiating agent composition is of an amount from about 0.00009 mg/kg body weight to about 10 g/kg body weight. According to another embodiment, the initiating agent composition is of an amount from about 0.0001 mg/kg body weight to about 10 g/kg body weight. According to another embodiment, the initiating agent composition is of an amount of about 0.0005 mg/kg body weight. According to another embodiment, the initiating agent composition is of an amount of about 0.001 mg/kg body Weight. According to another embodiment, the initiating agent composition is of an amount of about 0.005 mg/kg body weight. According to another embodiment, the initiating agent composition is of an amount of about 0.01 mg/kg body weight. According to another embodiment, the initiating agent composition is of an amount of about 0.1 mg/kg body weight. According to another embodiment, the initiating agent composition is of an amount of about 1 mg/kg body weight. According to another embodiment, the initiating agent composition is of an amount of about 10 mg/kg body weight. According to another embodiment, the initiating agent composition is of an amount of about 20 mg/kg body weight According to another embodiment, the initiating agent composition is of an amount of about 30 mg/kg body weight. According to another embodiment, the initiating agent composition is of an amount of about 40 mg/kg body weight. According to another embodiment, the initiating agent composition is of an amount of about 50 mg/kg body weight. According to another embodiment, the initiating agent composition is of an amount of about 60 mg/kg body weight. According to another embodiment, the initiating agent composition is of an amount of about 70 mg/kg body weight. According to another embodiment, the initiating agent composition is of an amount of about 80 mg/kg body weight. According to another embodiment, the initiating agent composition is of an amount of about 90 mg/kg body weight. According to another embodiment, the initiating agent composition is of an amount of about 100 mg/kg body weight. According to another embodiment, the initiating agent composition is of an amount of about 110 mg/kg body weight. According to another embodiment, the initiating agent composition is of an amount of about 120 mg/kg body weight. According to another embodiment, the initiating agent composition is of an amount of about 130 mg/kg body weight. According to another embodiment, the initiating agent composition is of an amount of about 140 mg/kg body weight. According to another embodiment, the initiating agent composition is of an amount of about 150 mg/kg body weight. According to another embodiment, the initiating agent composition is of an amount of about 160 mg/kg body weight. According to another embodiment, the initiating agent composition is of an amount of about 170 mg/kg body weight. According to another embodiment, the initiating agent composition is of an amount of about 180 mg/kg body weight. According to another embodiment, the initiating agent composition is of an amount of about 190 mg/kg body weight. According to another embodiment, the initiating agent composition is of an amount of about 200 mg/kg body weight. According to another embodiment, the initiating agent composition is of an amount of about 250 mg/kg body weight. According to another embodiment, the initiating agent composition is of an amount of about 500 mg/kg body weight.

According to another embodiment, the hemorrhagic condition of the brain is an intracerebral hematoma. According to one embodiment, the method further comprises the step of treating a mammal with an initiating agent composition for inducing an intracerebral hematoma. According to another embodiment, the initiating agent composition for inducing an intracerebral hematoma in the non-human animal model comprises whole blood. According to some embodiments, the whole blood is autologous. According to some embodiments, the whole blood is allogeneic. According to some embodiments, the whole blood is xenogeneic. According to some such embodiments, the blood is of a volume of about 1 µl to about 20 ml. According to some such embodiments, the blood is of a volume of about 100 µl to about 15 ml. According to some such embodiments, the blood is of a volume of about 500 µl to about 12.5 ml. According to some such embodiments, the blood is of a volume of about 1 ml to about 10 ml. According to some such embodiments, the volume of blood is about 2 ml. According to some such embodiments, the volume of blood is about 3 ml. According to some such embodiments, the volume of blood is about 4 ml. According to some such embodiments, the volume of blood is about 5 ml. According to some such embodiments, the volume of blood is about 6 ml. According to some such embodiments, the volume of blood is about 7 ml. According to some such embodiments, the volume of blood is about 8 ml. According to some such embodiments, the volume of blood is about 9 ml. According to some such embodiments, the initiating agent composition comprises at least one component of whole blood. Examples of components of whole blood include, but are not limited to, plasma, cellular components (e.g., red blood cells, white blood cells (including lymphocytes, monocytes, eosinophils, basophils, and neutrophils), and platelets), proteins (e.g., fibrinogen, albumin, immunoglobulins), hormones, coagulation factors, and fibrinolytic factors.

According to another embodiment, the initiating agent composition for inducing an intracerebral hematoma comprises a collagenase. As used herein, one unit (U) of collagenase activity solubilizes 1 mg of collagen fibrils per hour at 37° C. According to some embodiments, the initiating agent composition comprises a collagenase of an amount of about 0.001 U/mg body weight to about 100 U/mg body weight. According to some embodiments, the initiating agent composition comprises a collagenase of an amount of about 0.01 U/mg body weight to about 100 U/mg body weight. According to some embodiments, the initiating agent composition comprises a collagenase of an amount of about 0.1 U/mg body weight to about 100 U/mg body weight. According to some embodiments, the initiating agent composition comprises a collagenase of an amount of about 1 U/mg body weight to about 100 U/mg body weight. According to some embodiments, the initiating agent composition comprises a collagenase of an amount of about 25 U/mg body weight to about 100 U/mg body weight. According to some embodiments, the initiating agent composition comprises a collagenase of an amount of about 50 U/mg body weight to about 100 U/mg body weight. According to some embodiments, the initiating agent composition comprises a collagenase of an amount of about 75 μm, body weight to about 100 U/mg body weight.

According to another embodiment, the initiating agent composition for inducing an intracerebral hematoma comprises at least one antibody. According to another embodiment, the initiating agent composition for inducing an intracerebral hematoma comprises at least one monoclonal antibody. According to another embodiment, the initiating agent composition for inducing an intracerebral hematoma comprises at least one polyclonal antibody. According to some embodiments, the initiating agent composition comprises an anti-plasma antibody preparation.

According to other embodiments, the initiating agent composition comprises antibodies against at least one procoagulant (including, but not limited to, blood coagulation factors II, V, VII, IX, X, XI, XII, prekallikrein, kininogen and tissue factor), antibodies against anti-coagulants (including, but not limited to, protein C, protein S, antithrombin III, heparin cofactor II), clot structure factors (including, but not limited to, fibrinogen and factor XIII), fibrinolysis factors (such as, but not limited to, plasminogen, t-PA, PAI-1 and α2-plasmin inhibitor) and phospholipids.

According to some embodiments, at least one parameter characteristic of the intracerebral hematoma of a mammal with an induced an intracerebral hematoma is compared to at least one parameter characteristic of the intracerebral hematoma of a mammal that has been administered a compound or substance to be tested in order to determine the extent to which the substance to be tested can treat the induced intracerebral hematoma. Examples of parameters characteristic of intracerebral hematoma include, but is not limited to, a bleeding behavior, a volume of blood in the intracerebral hematoma, a size of the hematoma area, an expansion or a contraction of the hematoma area, expansion kinetics of the intracerebral hematoma, and contraction kinetics of the intracerebral hematoma. According to some embodiments, the substance is administered prior to induction of the intracerebral hematoma. According to some embodiments, the substance is administered simultaneously with the initiating agent composition. According to some embodiments, the substance is administered after induction of the intracerebral hematoma.

According to another embodiment, the initiating agent composition is administered to the brain of a mammal. According to some such embodiments, the initiating agent composition is administered to the brain following craniotomy. According to some such embodiments, the initiating agent composition is administered to the brain by a burr hole. According to some such embodiments, the burr hole is a frontal burr hole. According to some such embodiments, the burr hole is a parietal burr hole. According to some such embodiments, the burr hole is a temporal burr hole. According to some such embodiments, the burr hole is a suboccipital burr hole. According to some embodiments, stereotactic frames, image-guided computer systems, or endoscopes are used to direct instruments precisely through the burr hole.

No food or drink will be permitted 8 hours before surgery. General anesthesia will be administered. Once asleep, the animal's head will be placed in a skull fixation device to hold the head in position during the procedure.

After the hair of the intended incision area is shaved and the scalp is prepped with an antiseptic, a skin incision will be made. The skin and muscles will be lifted off the bone and folded back. Next, one or more small burr holes will be made in the skull with a surgical drill. In some embodiments, a bone flap will be created. The cut bone flap will be lifted and removed to expose the dura. The bone flap will be safely stored until it is replaced at the end of the procedure. In some cases, a drain may be placed under the skin for a couple of days to remove blood or fluid from the surgical area. The muscles and skin will be sutured back together, and a soft adhesive dressing will be placed over the incision.

According to some embodiments, the initiating agent composition is administered intracerebrally. According to some such embodiments, the initiating agent composition is administered by perfusion. According to some such embodiments, the initiating agent composition is administered subdurally. According to some such embodiments, the initiating agent composition is administered by surgical injection. According to some such embodiments, the initiating agent composition is deposited on or in an implant.

According to another embodiment, the initiating agent composition is of an amount from about 0.000001 mg/kg body weight to about 10 g/kg body weight. According to another embodiment, the initiating agent composition is of an amount from about 0.000002 mg/kg body weight to about 10 g/kg body weight. According to another embodiment, the initiating agent composition is of an amount from about 0.000003 mg/kg body weight to about 10 g/kg body weight. According to another embodiment, the initiating agent composition is of an amount from about 0.000004 mg/kg body weight to about 10 g/kg body weight. According to another embodiment, the initiating agent composition is of an amount from about 0.000005 mg/kg body weight to about 10 g/kg body weight. According to another embodiment, the initiating agent composition is of an amount from about 0.000006 mg/kg body weight to about 10 g/kg body weight. According to another embodiment, the initiating agent composition is of an amount from about 0.000007 mg/kg body weight to about 10 g/kg body weight. According to another embodiment, the initiating agent composition is of an amount from about 0.000008 mg/kg body weight to about 10 g/kg body weight. According to another embodiment, the initiating agent composition is of an amount from about 0.000009 mg/kg body weight to about 10 g/kg body weight. According to another embodiment, the initiating agent composition is of an amount from about 0.00001 mg/kg body weight to about 10 g/kg body weight. According to another embodiment, the initiating agent composition is of an amount from about 0.00002 mg/kg body weight to about 10 g/kg body weight. According to another embodiment, the initiating agent composition is of an amount from about 0.0003 mg/kg body weight to about 10 g/kg body weight. According to another embodiment, the initiating agent composition is of an amount from about 0.00004 mg/kg body weight to about 10 g/kg body weight. According to another embodiment, the initiating agent composition is of an amount from about 0.00005 mg/kg body weight to about 10 g/kg body weight. According to another embodiment, the initiating agent composition is of an amount from about 0.00006 mg/kg body weight to about 10 g/kg body weight. According to another embodiment, the initiating agent composition is of an amount from about 0.00007 mg/kg body weight to about 10 g/kg body weight. According to another embodiment, the initiating agent composition is of an amount from about 0.00008 mg/kg body weight to about 10 g/kg body weight. According to another embodiment, the initiating agent composition is of an amount from about 0.00009 mg/kg body weight to about 10 g/kg body weight. According to another embodiment, the initiating agent composition is of an amount from about 0.0001 mg/kg body weight to about 10 g/kg body weight. According to another embodiment, the initiating agent composition is of an amount of about 0.0005 mg/kg body weight. According to another embodiment, the initiating agent composition is of an amount of about 0.001 mg/kg body weight. According to another embodiment, the initiating agent composition is of an amount of about 0.005 mg/kg body weight. According to another embodiment, the initiating agent composition is of an amount of about 0.01 mg/kg body weight. According to another embodiment, the initiating agent composition is of an amount of about 0.1 mg/kg body weight. According to another embodiment, the initiating agent composition is of an amount of about 1 mg/kg body weight. According to another embodiment, the initiating agent composition is of an amount of about 10 mg/kg body weight. According to another embodiment, the initiating agent composition is of an amount of about 20 mg/kg body weight. According to another embodiment, the initiating agent composition is of an amount of about 30 mg/kg body weight. According to another embodiment, the initiating agent composition is of an amount of about 40 mg/kg body weight. According to another embodiment, the initiating agent composition is of an amount of about 50 mg/kg body weight. According to another embodiment, the initiating agent composition is of an amount of about 60 mg/kg body weight. According to another embodiment, the initiating agent composition is of an amount of about 70 mg/kg body weight. According to another embodiment, the initiating agent composition is of an amount of about 80 mg/kg body weight. According to another embodiment, the initiating agent composition is of an amount of about 90 mg/kg body weight. According to another embodiment, the initiating agent composition is of an amount of about 100 mg/kg body weight. According to another embodiment, the initiating agent composition is of an amount of about 110 mg/kg body weight. According to another embodiment, the initiating agent composition is of an amount of about 120 mg/kg body weight. According to another embodiment, the initiating agent composition is of an amount of about 130 mg/kg body weight. According to another embodiment, the initiating agent composition is of an amount of about 140 mg/kg body weight. According to another embodiment, the initiating agent composition is of an amount of about 150 mg/kg body weight. According to another embodiment, the initiating agent composition is of an amount of about 160 mg/kg body weight. According to another embodiment, the initiating agent composition is of an amount of about 170 mg/kg body weight. According to another embodiment, the initiating agent composition is of an amount of about 180 mg/kg body weight. According to another embodiment, the initiating agent composition is of an amount of about 190 mg/kg body weight. According to another embodiment, the initiating agent composition is of an amount of about 200 mg/kg body weight. According to another embodiment, the initiating agent composition is of an amount of about 250 mg/kg body weight. According to another embodiment, the initiating agent composition is of an amount of about 500 mg/kg body weight.

III. Pharmaceutical Compositions for Treating Hemorrhagic Conditions of the Brain According to another aspect, the described invention provides a pharmaceutical composition for treating a hemorrhagic condition of the brain in a mammal, the pharmaceutical composition comprising a therapeutically effective amount of a therapeutic agent and a pharmaceutical carrier. According to one embodiment, the hemorrhagic condition of the brain is a chronic SDH. According to one such embodiment, the pharmaceutical composition is a pharmaceutical composition for administration into or proximal to the dura mater. According to another embodiment, the hemorrhagic condition of the brain is an ICH. According to one such embodiment, the pharmaceutical composition is a pharmaceutical composition for administration into or proximal to a site of ICH.

According to one embodiment, the therapeutic agent comprises an antifibrinolytic agent, or an ester, salt, hydrate, solvate, functional derivative or prodrug thereof. According to another embodiment, the therapeutic agent comprises aminocaproic acid, a functional derivative of aminocaproic acid, or an ester, salt, hydrate, solvate, functional derivative or prodrug thereof. According to another embodiment, the therapeutic agent comprises Factor VII. According to another embodiment, the therapeutic agent comprises a recombinant Factor VII. According to another embodiment, the therapeutic agent comprises tranexamic acid, or an ester, salt, hydrate, solvate, functional derivative or prodrug thereof. According to another embodiment, the therapeutic agent comprises aprotinin. According to another embodiment, the therapeutic agent comprises antiplasmin, or an ester, salt, hydrate, solvate, functional derivative or prodrug thereof. According to another embodiment, the therapeutic agent comprises fibrin fragment D, or an ester, salt, hydrate, solvate, functional derivative or prodrug thereof. According to another embodiment, the therapeutic agent comprises vitamin K, or an ester, salt, hydrate, solvate, functional derivative or prodrug thereof. According to another embodiment, the therapeutic agent comprises vitamin $K_1$, or an ester, salt, hydrate, solvate, functional derivative or prodrug thereof. According to another embodiment, the therapeutic agent comprises vitamin $K_2$, or an ester, salt, hydrate, solvate, functional derivative or prodrug thereof. According to another embodiment, the therapeutic agent comprises vitamin $K_3$, or an ester, salt, hydrate, solvate, functional derivative or prodrug thereof. According to another embodiment, the therapeutic agent comprises 4-aminomethylbenzoic acid or an ester, salt, hydrate, solvate, functional derivative or prodrug thereof.

According to another embodiment, the pharmaceutically acceptable carrier is a gel compound.

According to another embodiment, the pharmaceutically acceptable carrier is a semisolid compound.

According to another embodiment, the pharmaceutically acceptable carrier is a sustained-release compound.

Compositions

According to another aspect, the described invention provides a site-specific, sustained-release pharmaceutical composition for treating hematoma expansion or recurrent rebleeding resulting from a hemorrhagic condition in brain, the pharmaceutical composition comprising: (a) a therapeutically effective amount of an anti-fibrinolytic agent; and (b) a pharmaceutically acceptable carrier, wherein the pharmaceutically acceptable carrier is a sustained-release carrier.

According to one embodiment, the hemorrhagic brain condition is rebleeding following traumatic brain injury.

According to another embodiment, the hemorrhagic brain condition is a chronic SDH.

According to another embodiment the hemorrhagic brain condition is an ICH.

According to another embodiment the intracerebral hematoma is a spontaneous ICH.

According to another embodiment, the intracerebral hematoma is a traumatic ICH.

According to another embodiment, the hemorrhagic brain condition is rebleeding following a craniotomy procedure.

According to another embodiment, the craniotomy procedure is performed for treating a brain cancer.

According to another embodiment, the craniotomy procedure is performed for treating a vascular malformation in brain.

According to another embodiment, the craniotomy procedure is performed for treating a brain aneurysm.

According to another embodiment, the anti-fibrinolytic agent is ε-aminocaproic acid (AMICAR).

According to another embodiment, the anti-fibrinolytic agent is Factor VII.

According to another embodiment the Factor VII is a recombinant Factor VII.

According to another embodiment, the anti-fibrinolytic agent is tranexamic acid.

According to another embodiment, the anti-fibrinolytic agent is aprotinin.

According to another embodiment, the pharmaceutically acceptable carrier is a controlled-release carrier.

According to another embodiment, the pharmaceutically acceptable carrier is a sustained-release carrier.

According to another embodiment, the anti-fibrinolytic agent is embedded in the sustained-release carrier.

According to another embodiment, the anti-fibrinolytic agent is coated on the sustained-release carrier.

According to another embodiment, the sustained-release carrier releases the anti-fibrinolytic agent for at least 21 days post-administration.

According to another embodiment, the sustained-release carrier releases the anti-fibrinolytic agent for about 3 to 5 days post-administration.

According to another embodiment, the sustained-release carrier comprises a microparticle.

According to another embodiment, the sustained-release carrier comprises a nanoparticle.

According to another embodiment, the sustained-release carrier comprises a biodegradable polymer.

According to another embodiment, the biodegradable polymer is a synthetic polymer.

According to another embodiment, the biodegradable polymer is a naturally occurring polymer.

According to another embodiment, the synthetic polymer is selected from the group consisting of a polyester, a polyester polyethylene glycol polymer, a polyamino-derived biopolymer, a polyanhydride, a polyorthoester, a polyphosphazene, a sucrose acetate isobutyrate (SAIB), a photopolymerizable biopolymer, and a combination thereof.

According to another embodimentm the synthetic polymer is polyglyolic acid (PGA).

According to another embodiment, the synthetic polymer is a copolymer of polyglycolic acid formed with trimethylene carbonate, polylacitic acid (PLA), or polycaprolactone.

According to another embodiment, the sustained-release carrier is a hydrogel.

According to another embodiment, the naturally occurring polymer is a protein polymer.

According to another embodiment, the protein polymer is synthesized from self-assembling protein polymers comprising silk fibroin, elastin, collangen, or a combination thereof.

According to another embodiment, the naturally occurring polymer is a naturally occurring polysaccharide.

According to another embodiment the naturally occurring polymer comprises a hyaluronic acid.

According to another embodiment, the naturally occurring polymer comprises less than 2.3% of hyaluronic acid.

The therapeutic agents in the compositions are delivered in therapeutically effective amounts. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular therapeutic agent(s) being administered, the size of the subject, or the severity of the disease or condition. One of ordinary skill in the art may determine empirically the effective amount of a particular therapeutic agent(s) without necessitating undue experimentation. It generally is preferred that a maximum dose be used, that is, the highest safe dose according to some medical judgment. The terms "dose" and "dosage" are used interchangeably herein.

For any compound described herein the therapeutically effective amount may be initially determined from preliminary in vitro studies and/or animal models. A therapeutically effective dose also may be determined from human data for therapeutic agent(s) which have been tested in humans and for compounds which are known to exhibit similar pharmacological activities, such as other related active agents. The applied dose may be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of therapeutic agent(s) may be administered in pharmaceutically acceptable solutions, which may routinely contain pharmaceutically acceptable concentrations of salt, buffering agents, preservatives, compatible carriers, adjuvants, and optionally other therapeutic ingredients.

According to some embodiments, the compositions of the described invention comprising a therapeutic agent(s) can further include one or more additional compatible active ingredients.

For use in therapy, an effective amount of the therapeutic agent(s) may be administered to a subject by any mode that delivers the therapeutic agent to the desired surface. Administering the pharmaceutical composition may be accomplished by any means known to the skilled artisan. Routes of administration include, but are not limited to, subdural, intracerebral, intrathecal, intra-arterial, parenteral (e.g. intravenous), or intramuscular. The therapeutics may be delivered to a subject during surgery to treat an underlying condition or side effect such as chronic SDH, ICH or during other procedures.

The therapeutic agent(s), when it is desirable to deliver it locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into tissue, or dried onto an object to be rubbed into tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The therapeutics may be administered in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a therapeutic agent(s), or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate, functional derivative or prodrug thereof may be mixed with other active materials that do not impair the desired action, or with materials that supplement the desired action. Solutions or suspensions used for parenteral, intradermal, subcutaneous, subdural, intracerebral, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules (or ampules), disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms may be made by forming microencapsulated matrices of the drug in biodegradable polymers such as, but not limited to, polyesters (polyglycolide, polylactic acid and combinations thereof), polyester polyethylene glycol copolymers, polyamino-derived biopolymers, polyanhydrides, polyorthoesters, polyphosphazenes, sucrose acetate isobutyrate (SAIB), photopolymerizable biopolymers, naturally-occurring biopolymers, protein polymers, collagen; and polysaccharides. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Depot injectable formulations also are prepared by entrapping the drug in liposomes or microemulsions which are compatible with body tissues.

Polyglycolide (PGA) is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

Polyester-polyethylene glycol compounds can be synthesized; these are soft and may be used for drug delivery.

Poly(amino)-derived biopolymers may include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

Photopolymerizable biopolymers include, but are not limited to, lactic acid/polyethylene glycol/acrylate copolymers.

The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

Naturally-occurring biopolymers include, but are not limited to, protein polymers, collagen, polysaccharides, and photopolymerizable compounds.

Protein polymers have been synthesized from self-assembling protein polymers such as, for example, silk fibroin, elastin, collagen, and combinations thereof.

Naturally-occurring polysaccharides include, but are not limited to, chitin and its derivatives, hyaluronic acid, dextran and cellulosics (which generally are not biodegradable without modification), and sucrose acetate isobutyrate (SAIB).

Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

Hyaluronic acid (HA), which is composed of alternating glucuronidic and glucosaminidic bonds and is found in mammalian vitreous humor, synovial fluid, unbiblical cords and rooster combs, from which it is isolated and purified, also can be produced by fermentation processes.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P., phosphate-buffered saline (PBS), and isotonic sodium chloride solution. In addition, sterile, fixed oils conventionally are employed or as a solvent or suspending medium. For this purpose any bland fixed oil may be employed including synthetic mono- or diglycerides. In addition, Tatty acids such as oleic acid are used in the preparation of injectables.

Formulations for parenteral (including but not limited to, intracerebral, subdural, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 also may be used. The polymer may be conjugated via an ester linkage to one or more hydroxyls of a therapeutic agent using a protocol as essentially described by U.S. Pat. No. 5,977,163 which is incorporated herein by reference.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions within the described invention contain a therapeutically effective amount of at least one therapeutic agent and optionally other therapeutic agents included in a pharmaceutically-acceptable carrier. The components of the pharmaceutical compositions also are capable of being comingled in a manner such that there is no interaction which would substantially impair the desired pharmaceutical efficiency.

The therapeutic agent(s) also may be provided in particles, strings, or sheets.

According to one embodiment, the therapeutic agent(s) may be provided in particles. The particles may contain the therapeutic agent(s) in a core surrounded by a coating, or the therapeutic agent(s) may be dispersed throughout the particles, or the therapeutic agent(s) may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules, nanocapsules or in some instances larger that contain the therapeutic agent(s) in a solution or in a semi-solid state. The particles may be of virtually any shape. According to some embodiments the particle that may contain, in whole or in part, at least one therapeutic agent is a microparticle. According to some embodiments, the particle that may contain, in whole or in part, at least one therapeutic agent is a nanoparticle.

According to another embodiment, the therapeutic agent(s) may be provided in strings. The strings may contain the therapeutic agent(s) in a core surrounded by a coating, or the therapeutic agent(s) may be dispersed throughout the string, or the therapeutic agent(s) may be absorbed into the string. The string may be of any order release kinetics, including zero order release, first order release, second order release, delayed release, sustained release, immediate release, etc., and any combination thereof. The string may include, in addition to the therapeutic agent(s), any of those materials routinely used in the art of pharmacy and medicine, including, but not limited to, erodible, nonerodible, biodegradable, or nonbiodegradable material or combinations thereof.

According to another embodiment, the therapeutic agent(s) may be provided in at least one sheet. The sheet may contain the therapeutic agent(s) in a core surrounded by a coating, or the therapeutic agent(s) may be dispersed throughout the sheet, or the therapeutic agent(s) may be absorbed into the sheet. The sheet may be of any order release kinetics, including zero order release, first order release, second order release, delayed release, sustained release, immediate release, etc., and any combination thereof. The sheet may include, in addition to the therapeutic agent(s), any of those materials routinely used in the art of pharmacy and medicine, including, but not limited to, erodible, nonerodible, biodegradable, or nonbiodegradable material or combinations thereof.

Both non-biodegradable, and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et at in Macromolecules (1993) 26, 581-587, the teachings of which are incorporated herein. These include polyesters (polyglycolide, polylactic acid and combinations thereof), polyester polyethylene glycol copolymers, polyamino-derived biopolymers, polyanhydrides, polyorthoesters, polyphosphazenes, sucrose acetate isobutyrate (SAIB), and photopolymerizable biopolymers, naturally-occurring biopolymers, protein polymers, collagen, polysaccharides, photopolymerizable compounds, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). In some embodiments, the bioadhesive polymers of the described invention include hyaluronic acid. According to some such embodiments, the bioadhesive polymer include less than about 2.3% of hyaluronic acid.

The therapeutic agent(s) may be contained in controlled release systems. In order to prolong the effect of a drug, it often is desirable to slow the absorption of the drug from subdural, intracerebral, subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. For example, according to some embodiments, a SABER™ Delivery System comprising a high-viscosity base component, such as sucrose acetate isobutyrate (SAIB), is used to provide controlled release of the drug. (See U.S. Pat. No. 5,747,058 and U.S. Pat. No. 5,968,542, incorporated herein by reference). When the high viscosity SAIB is formulated with drug, biocompatible excipients and other additives, the resulting formulation is liquid enough to inject easily with standard syringes and needles. After injection of a SABER™ formulation, the excipients diffuse away, leaving a viscous depot.

As used herein, the term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. Long-term sustained release implants are well-known to those of ordinary skill in the art and include some of the release systems described above.

Delivery Systems

According to another aspect, the described invention provides a semisolid delivery system for therapeutic agents and a combination semisolid, multiparticulate, therapeutic delivery system for therapeutic agents. For example, the described invention provides a delivery system that utilizes a semisolid, biodegradable, biocompatible delivery system for injection, depositon or implantation within or upon the body so as to favorable local therapeutic effects. Alternatively, the described invention provides a biodegradable, biocompatible multiparticulate dispersed and suspended in a semisolid, biodegradable, biocompatible biodegradable delivery system for injection, deposition or implantation within or upon the body so as to facilitate local therapeutic effects.

Additionally, the semisolid delivery system comprises at least in part a biocompatible, biodegradable, viscous semisolid wherein the semisolid comprises a hydrogel that hydrogel incorporates and retains significant amounts of $H_2O$, which eventually will reach an equilibrium content in the presence of an aqueous environment. According to one embodiment, glyceryl monooleate, hereinafter referred to as GMO, is the intended semisolid delivery system or hydrogel. However, many hydrogels, polymers, hydrocarbon compositions and fatty acid derivatives having similar physical/chemical properties with respect to viscosity/rigidity may function as a semisolid delivery system.

According to one embodiment, the gel system is produced by heating GMO above its melting point (40° C. to 50° C.) and by adding a warm aqueous-based buffer or electrolyte solution, such as, for example, phosphate buffer or normal saline, which thus produces a three-dimensional structure. The aqueous-based buffer may be comprised of other aqueous solutions or combinations containing semi-polar solvents.

GMO provides a predominantly lipid-based hydrogel, which has the ability to incorporate lipophilic materials. GMO further provides internal aqueous channels that incorporate and deliver hydrophilic compounds. It is recognized that at room temperature (about 25° C.), the gel system may exhibit differing phases which comprise a broad range of viscosity measures.

According to one embodiment, two gel system phases are utilized due to their properties at room temperature and physiologic temperature (about 37° C.) and pH (about 7.4). Within the two gel system phases, the first phase is a lamellar phase of approximately 5% to approximately 15% $H_2O$ content and approximately 95% to approximately 85% GMO content. The lamellar phase is a moderately viscous fluid, that may be easily manipulated, poured and injected. The second phase is a cubic phase consisting of approximately 15% to approximately 40% $H_2O$ content and approximately 85%-60% GMO content. It has an equilibrium water content at approximately 35% to approximately 40% by weight. The term "equilibrium water content" as used herein refers to maximum water content in the presence of excess water. Thus the cubic phase incorporates water at approximately 35 to approximately 40% by weight. The cubic phase is highly viscous. Viscosity may be measured, for example, via a Brookfield viscometer. The viscosity exceeds 1.2 million centipoise (cp); wherein 1.2 million cp being the maximum measure of viscosity obtainable via the cup and bob configuration of the Brookfield viscometer. According to some such embodiments, a therapeutic agent may be incorporated into the semisolid so as to provide a system for sustained, continuous delivery thereof. According to some such embodiments, the therapeutic agent comprises tranexamic acid or an ester, salt, hydrate, solvate, functional derivative or prodrug thereof. According to some such embodiments, the therapeutic agent comprises aminocaproic acid or an ester, salt, hydrate, solvate, functional derivative or prodrug thereof. According to some such embodiments, the therapeutic agent comprises factor VII. According to some such embodiments, the therapeutic agent comprises a recombinant factor VII. According to some such embodiments, the therapeutic agent comprises aprotinin. According to some such embodiments, other therapeutic agents, biologically-active agents, drugs, medicaments and inactives may be incorporated into the semisolid for providing a local biological, physiological, or therapeutic effect in the body at various release rates.

According to some embodiments, alternative semisolids, modified formulations and methods of production are utilized such that the lipophilic nature of the semisolid is altered, or in the alternative, the aqueous channels contained within the semisolid are altered. Thus, various therapeutic agents in varying concentrations may diffuse from the semisolid at differing rates, or be released therefrom over time via the aqueous channels of the semisolid. Hydrophilic substances may be utilized to alter semisolid consistency or therapeutic agent release by alteration of viscosity, fluidity, surface tension or the polarity of the aqueous component. For example, glyceryl monostearate (GMS), which is structurally identical to GMO with the exception of a double bond at Carbon 9 and Carbon 10 of the fatty acid moiety rather than a single bond, does not gel upon heating and the addition of an aqueous component, as does GMO. However, because GMS is a surfactant, GMS is miscible in $H_2O$ up to approximately 20% weight/weight. The term "surfactant" as used herein refers to a surface active agent, thus being miscible in $H_2O$ in limited concentrations as well as polar substances. Upon heating and stirring, the 80% $H_2O$/20% GMS combination produces a spreadable paste having a consistency resembling hand lotion. The paste then is combined with melted GMO so as to form the cubic phase gel possessing a high viscosity as stated heretofore. According to some such embodiments, the therapeutic agent comprises tranexamic acid or an ester, salt, hydrate, solvate, functional derivative or prodrug thereof. According to some such embodiments, the therapeutic agent comprises aminocaproic acid or an ester, salt, hydrate, solvate, functional derivative or prodrug thereof. According to some such embodiments, the therapeutic agent comprises Factor VII or recombinant Factor VII. According to some such embodiments, the therapeutic agent comprises aprotinin.

According to another embodiment, hydrolyzed gelatin, such as commercially available Gelfoam™, is utilized for altering the aqueous component. Approximately 6.25% to 12.50% concentration of Gelfoam™ by weight may be placed in approximately 93.75% to 87.50% concentration of $H_2O$ respectively by weight or other aqueous based buffer. Upon heating and stirring, the $H_2O$ (or other aqeuous buffer)/Gelfoam™ combination produces a thick gelatinous substance. The resulting substance is combined with GMO, whereby a product so formed swells and forms a highly viscous, translucent gel being less malleable in comparison to neat GMO gel alone.

According to another embodiment, polyethylene glycols (PEG's) may be utilized for altering the aqueous component to aid in drug solubilization. Approximately 0.5% to 40% concentration of PEG's (depending on PEG molecular weight) by weight placed in approximately 99.5% to 60% concentration of $H_2O$ respectively by weight or other aqueous based buffer. Upon heating and stirring, the $H_2O$ (or other aqeuous buffer)/PEG combination produces a viscous liquid to a semisolid substance. The resulting substance is combined with GMO, whereby a product so formed swells and forms a highly viscous gel.

Without being limited by theory, for example, the therapeutic agent releases from the semisolid through diffusion, conceivably in a biphasic manner. A first phase involves, for example, a lipophilic drug contained within the lipophilic membrane diffuses therefrom into the aqueous channel. The second phase involves diffusion of the drug from the aqueous channel into the external environment. Being lipophilic, the drug may orient itself inside the GMO gel within its proposed lipid bi-layer structure. Thus, incorporating greater than approximately 7.5% of the drug by weight into GMO causes a loss of the integrity of the three-dimensional structure whereby the gel system no longer maintains the semisolid cubic phase, and reverts to the viscous lamellar phase liquid. According to some such embodiments, the therapeutic agent comprises tranexamie acid or an ester, salt, hydrate, solvate, functional derivative or prodrug thereof. According to some such embodiments, the therapeutic agent comprises aminocaproic acid or an ester, salt, hydrate, solvate, functional derivative or prodrug thereof. According to some such embodiments, the therapeutic agent comprises Factor VII or a recombinant Factor VB. According to some such embodiments, the therapeutic agent comprises aprotinin. According to another embodiment, about 1 to about 45% of therapeutic agent is incorporated by weight into a GMO gel at physiologic temperature without disruption of the normal three-dimensional structure. As a result, this system allows the ability of significantly increased flexibility with drug dosages. Because the delivery system is malleable, it may be delivered and manipulated in an implant site, for example, adjacent to or in a chronic SDH, so as to adhere and conform to contours of walls, spaces, or other voids in the body as well as completely fill all voids existing. The delivery system ensures drug distribution and uniform drug delivery throughout the implant site. Ease of delivery and manipulation of the delivery system within a space, for example, but not limited to the surface of the brain, is facilitated via a semisolid delivery apparatus. A semisolid delivery apparatus facilitates targeted and controlled delivery of the delivery system.

According to one embodiment, the multiparticulate component is comprised of biocompatible, biodegradable, polymeric or non-polymeric systems utilized to produce solid structures including but not limited to nonpareils, pellets, strings, sheets, crystals, agglomerates, microparticles, or nanoparticles.

According to another embodiment, the multiparticulate component comprises of poly(lactic-co-glycolide) (PLGA's). PLGA's are biodegradable polymer materials used for controlled and extended therapeutic agent delivery within the body. Such delivery systems offer enhanced therapeutic efficacy and reduced overall toxicity as compared to frequent periodic, systemic dosing. Without being limited by theory, for example, PLGA's systems consisting of differing molar ratios of the monomeric subunits will facilitate greater flexibility in engineering precise release profiles for accommodating targeted therapeutic agent delivery through alterations in the rate of polymer degradation. According to one embodiment, the PLGA composition is sufficiently pure so as to be biocompatible and remains biocompatible upon biodegradation. According to one embodiment, the PLGA polymer is designed and configured into microparticles having a therapeutic agent or drug entrapped therein, whereby the therapeutic agent is subsequently released therefrom by a method to be described in greater detail below. According to some such embodiments, the therapeutic agent comprises aminocaproic acid or an ester, salt, hydrate, solvate, functional derivative or prodrug thereof. According to some such embodiments, the therapeutic agent comprises tranexamic acid or an ester, salt, hydrate, solvate, functional derivative or prodrug thereof. According to some such embodiments, the therapeutic agent comprises Factor VII or recombinant Factor VII. According to some such embodiments, the therapeutic agent comprises aprotinin.

According to another embodiment, the multiparticulate component is comprised of poly d,l(lactic-co-caprolactone). This provides a biodegradable polymer material used for controlled and extended therapeutic agent delivery within the body with a similar drug release mechanism to that of the PLGA polymers. According to one embodiment, the multiparticulate microparticles also are produced using biodegradable and/or biocompatible non-polymeric materials such as GMS.

According to another embodiment, the multiparticulate component is further modified by methods used to encapsulate or coat the multiparticulate components using polymers of the same composition with the same or different drug substances, different polymers with the same or different drug substances, or with multiple layering processes containing no drug, the same drug, a different drug, or multiple drug substances. This allows the production of a multi-layered (encapsulated) multiparticulate system with a wide range of drug release profiles for single or multiple drug agents simultaneously. According to another embodiment, coating materials which control the rate of physical drug diffusion from the multiparticulate may be utilized alone or in concert with the aforementioned preferred embodiments and envisioned embodiments.

According to another embodiment, the present invention provides a delivery system that utilizes PLGA. The PLGA polymer contains ester bonds, which are labile to hydrolysis. When $H_2O$ penetrates the PLGA polymer, the ester bonds thereof are hydrolyzed, and monomers, being water soluble, are removed from the ALGA polymer, thus facilitating the physical release of the entrapped drug over time. According to some such embodiments, other classes of synthetic biodegradable, biocompatible polymers may be used for controlled and extended therapeutic agent delivery within the body, including polyanhydrides, poly(phosphates), polydioxanone, cellulosics and acrylics which are extended as non-limiting examples. According to some such embodiments, nonpolymeric materials may be utilized for controlled and extended therapeutic agent delivery within the body, including but not limited to sterols, sucrose fatty acid esters, fatty acids, and cholesteryl esters, which are extended as non-limiting examples.

According to another embodiment, the described invention provides a semisolid delivery system, which acts as a vehicle for local delivery of therapeutic agents, comprising a lipophilic, hydrophilic or amphophilic, solid or semisolid substance, heated above its melting point and thereafter followed by inclusion of a warm aqueous component so as to produce a gelatinous composition of variable viscosity based on water content. The therapeutic agent(s) is incorporated and dispersed into the melted lipophilic component or the aqueous buffer component prior to mixing and formation of the semisolid system. The gelatinous composition is placed within the semisolid delivery apparatus for subsequent placement, or deposition. Being malleable, the gel system is easily delivered and manipulated via the semisolid delivery apparatus in an implant site, where it adheres and conforms to contours of the implantation site, spaces, or other voids in the body as well as completely filling all voids existing. Alternatively, a multiparticulate component, comprised of a biocompatible polymeric or non-polymeric system, is utilized for producing microparticles having a therapeutic agent entrapped therein. Following final processing methods, the microparticles are incorporated into the semisolid system and subsequently placed within the semisolid delivery apparatus so as to be easily delivered therefrom into an implant site or comparable space, whereby the therapeutic agent is subsequently released therefrom by (a) drug release mechanism(s).

According to another embodiment, a SABER™ Delivery System comprising a high-viscosity base component, such as sucrose acetate isobutyrate (SAIB), is used to provide controlled release of the drug.

IV. Method for Treating a Hemorrhagic Condition of the Brain

According to another aspect, the described invention provides a method for treating hematoma expansion or recurrent bleeding resulting from a hemorrhagic condition of brain in a mammal, the method comprising steps:

(a) providing a pharmaceutical composition comprising:
  (i) a therapeutically effective amount of an anti-fibrinolytic agent; and
  (ii) a pharmaceutically acceptable carrier;
(b) administering the pharmaceutical composition of (a) to a predetermined location into or at a distance proximal to the hematoma in the brain; and
(c) improving patient outcome.

According to one embodiment, the hemorrhagic condition results from traumatic brain injury (TBI).

According to another embodiment, the hemorrhagic condition is rebleeding following a surgical evacuation of the hematoma.

According to another embodiment, the hemorrhagic condition is a chronic subdural hematoma (SDH).

According to another embodiment, the hemorrhagic condition is an intracerebral hematoma (ICH).

According to another embodiment, the intracerebral hematoma is a spontaneous intracerebral hematoma (ICH).

According to another embodiment, the intracerebral hematoma is a traumatic intracerebral hematoma (ICH).

According to another embodiment, the hemorrhagic condition is rebleeding following a craniotomy procedure.

According to another embodiment, the craniotomy procedure is performed for treating a brain cancer.

According to another embodiment, the craniotomy procedure is performed for treating a vascular malformation in brain.

According to another embodiment, the craniotomy procedure is performed for treating a brain aneurysm.

According to another embodiment, the administration is an implantation. According to another embodiment, the anti-fibrinolytic agent is ε-aminocaproic acid (AMICAR).

According to another embodiment, the anti-fibrinolytic agent is Factor VII.

According to another embodiment, the Factor VII is a recombinant Factor VII.

According to another embodiment, the anti-fibrinolytic agent is tranexamic acid.

According to another embodiment, the anti-fibrinolytic agent is aprotinin.

According to another embodiment, the pharmaceutically acceptable carrier is a controlled-release carrier.

According to another embodiment, the pharmaceutically acceptable carrier is a sustained-release carrier.

According to another embodiment, the anti-fibrinolytic agent is embedded in the sustained-release carrier.

According to another embodiment, the anti-fibrinolytic agent is coated on the sustained-release carrier.

According to another embodiment, the sustained-release, carrier releases the anti-fibrinolytic agent for at least 21 days post-administration.

According to another embodiment, the sustained-release carrier releases the anti-fibrinolytic agent for about 3 to 5 days post-administration.

According to another embodiment, the sustained-release carrier is a microparticle.

According to another embodiment, the sustained-release carrier is a nanoparticle.

According to another embodiment, the sustained-release carrier comprises a biodegradable polymer.

According to another embodiment, the biodegradable polymer is a synthetic polymer.

According to another embodiment, the biodegradable polymer is a naturally occurring polymer.

According to another embodiment, the synthetic polymer is selected from the group consisting of a polyester, a polyester polyethylene glycol polymer, a polyamino-derived biopolymer, a polyanhydride, a polyorthoester, a polyphosphazene, a sucrose acetate isobutyrate (SAIB), a photopolymerizable biopolymer, and a combination thereof.

According to another embodiment, the synthetic polymer is polyglyolic acid (PGA).

According to another embodiment, the synthetic polymer is a copolymer of polyglycolic acid formed with trimethylene carbonate, polylacitic acid (PLA), or polycaprolactone.

According to another embodiment, the sustained-release carrier is a hydrogel.

According to another embodiment, the naturally occurring biopolymer is a protein polymer.

According to another embodiment, the naturally occurring polymer comprises hyaluronic acid.

According to another embodiment, the naturally occurring polymer comprises less than 2.3% of hyaluronic acid.

According to another embodiment, the distance proximal to the hematoma is from about 0.5 mm to about 10 mm. According to another embodiment, the distance proximal to the hematoma is from about 0.5 mm to about 10 mm. According to another embodiment, the distance proximal to the hematoma is from about 0.5 mm to about 9 mm. According to another embodiment, the distance proximal to the hematoma is from about 0.5 mm to about 8 mm. According to another embodiment, the distance proximal to the hematoma is from about 0.5 mm to about 7 mm. According to another embodiment, the distance proximal to the hematoma is from about 0.5 mm to about 6 mm. According to another embodiment, the distance proximal to the hematomais from about 0.5 mm to about 5 mm from the at least one edge of the hematoma. According to another embodiment, the distance proximal to the hematoma is from about 0.5 mm to about 4 mm. According to another embodiment, the distance proximal to the hematomais from about 0.5 mm to about 3 mm. According to another embodiment, the distance proximal to the hematoma is from about 0.5 mm to about 2 mm. According to another embodiment, the distance proximal to the hematomas from about 0.5 mm to about 1 mm.

According to another embodiment, the distance proximal to the hematoma is from about 0.6 mm to about 10 mm. According to another embodiment, the distance proximal to the hematoma is from about 0.6 mm to about 9 mm. According to another embodiment, the distance proximal to the hematoma is from about 0.6 mm to about 8 mm. According to another embodiment, the distance proximal to the hematomais from about 0.6 mm to about 7 mm. According to another embodiment, the distance proximal to the hematoma is from about 0.6 mm to about 6 mm. According to another embodiment, the distance proximal to the hematomais from about 0.6 mm to about 5 mm. According to another embodiment, the distance proximal to the hematoma is from about 0.6 mm to about 4 mm. According to another embodiment, the distance proximal to the hematomais from about 0.6 mm to about 3 mm. According to another embodiment, the distance proximal to the hematoma is from about 0.6 mm to about 2 mm. According to another embodiment, the distance proximal to the hematomais from about 0.6 mm to about 1 mm.

According to another embodiment, the distance proximal to the hematoma is from about 0.7 mm to about 10 mm. According to another embodiment, the distance proximal to the hematoma is from about 0.7 mm to about 9 mm. According to another embodiment, the distance proximal to the hematoma is from about 0.7 mm to about 8 mm. According to another embodiment, the distance proximal to the hematomais from about 0.7 mm to about 7 mm. According to another embodiment, the distance proximal to the hematoma is from about 0.7 mm to about 67 mm. According to another embodiment, the distance proximal to the hematomais from about 0.7 mm to about 5 mm. According to another embodiment, the distance proximal to the hematoma is from about 0.7 mm to about 4 mm. According to another embodiment, the distance proximal to the hematomais from about 0.7 mm to about 3 mm. According to another embodiment, the distance proximal to the hematoma is from about 0.7 mm to about 2 mm. According to another embodiment, the distance proximal to the hematomais from about 0.7 mm to about 1 mm.

According to another embodiment, the distance proximal to the hematoma is from about 0.8 mm to about 10 mm. According to another embodiment, the distance proximal to the hematoma is from about 0.8 mm to about 9 mm. According to another embodiment, the distance proximal to the hematoma is from about 0.8 mm to about 8. According to another embodiment, the distance proximal to the hematomais from about 0.8 mm to about 7 mm. According to another embodiment, the distance proximal to the hematoma is from about 0.8 mm to about 6 mm. According to another embodiment, the distance proximal to the hematomais from about 0.8 mm to about 5 mm. According to another embodiment, the distance proximal to the hematoma is from about 0.8 mm to about 4 mm. According to another embodiment, the distance proximal to the hematomais from about 0.8 mm to about 3 mm. According to another embodiment, the distance proximal to the hematoma is from about 0.8 mm to about 2 mm. According to another embodiment, the distance proximal to the hematomais from about 0.8 mm to about 1 mm.

According to another embodiment, the distance proximal to the hematoma is from about 0.9 mm to about 10 mm. According to another embodiment, the distance proximal to the hematoma is from about 0.9 mm to about 9 mm. According to another embodiment, the distance proximal to the hematoma is from about 0.9 mm to about 8 mm. According to another embodiment, the distance proximal to the hematomais from about 0.9 mm to about 7 mm. According to another embodiment, the distance proximal to the hematomais from about 0.9 mm to about 6 mm. According to another embodiment, the distance proximal to the hematomais from about 0.9 mm to about 5 mm. According to another embodiment, the distance proximal to the hematoma is from about 0.9 mm to about 4 mm. According to another embodiment, the distance proximal to the hematomais from about 0.9 mm to about 3 mm. According to another embodiment, the distance proximal to the hematoma is from about 0.9 mm to about 2 mm. According to another embodiment, the distance proximal to the hematomais from about 0.9 mm to about 1 mm.

According to another embodiment, the distance proximal to the hematoma is from about 1 mm to about 10 mm. According to another embodiment, the distance proximal to the hematoma is from about 2 mm to about 10 mm. According to another embodiment, the distance proximal to the hematoma is from about 3 mm to about 10 mm. According to another embodiment, the distance proximal to the hematoma is from about 4 mm to about 10 mm. According to another embodiment, the distance proximal to the hematoma is from about 5 mm to about 10 mm. According to another embodiment, the distance proximal to the hematoma is from about 5 mm to about 10 mm. According to another embodiment, the distance proximal to the hematoma is from about 6 mm to about 10 mm. According to another embodiment, the distance proximal to the hematoma is from about 7 mm to about 10 mm. According to another embodiment, the distance proximal to the hematoma is from about 8 mm to about 10 mm. According to another embodiment, the distance proximal to the hematoma is from about 9 mm to about 10 mm. According to another embodiment, the distance proximal to the hematoma is from about 9.5 mm to about 10 mm. According to another embodiment, the distance proximal to the hematoma is from about 9.6 mm to about 10 mm. According to another embodiment, the distance proximal to the hematoma is from about 9.7 mm to about 10 mm. According to another embodiment, the distance proximal to the hematoma is from about 9.8 mm to about 10 mm. According to another embodiment, the distance proximal to the hematoma is from about 9.9 mm to about 10 mm.

According to another embodiment, the pharmaceutical composition exhibits a localized pharmacological effect.

According to another embodiment, the pharmaceutical composition exhibits its pharmacological effect throughout the brain.

According to another embodiment, the therapeutically effective amount is from about 0.000001 mg/kg body weight to about 10 g/kg body weight. According to another embodiment, the therapeutically effective amount is from about 0.000002 mg/kg body weight to about 10 g/kg body weight. According to another embodiment, the therapeutically effective amount is from about 0.000003 mg/kg body weight to about 10 g/kg body weight. According to another embodiment, the therapeutically effective amount is from about 0.000004 mg/kg body weight to about 10 g/kg body weight. According to another embodiment, the therapeutically effective amount is from about 0.000005 mg/kg body weight to about 10 g/kg body weight. According to another embodiment, the therapeutically effective amount is from about 0.000006 mg/kg body weight to about 10 g/kg body weight. According to another embodiment, the therapeutically effective amount is from about 0.000007 mg/kg body weight to about 10 g/kg body weight. According to another embodiment, the therapeutically effective amount is from about 0.000008 mg/kg body weight to about 10 g/kg body weight. According to another embodiment, the therapeutically effective amount is from about 0.000009 mg/kg body weight to about 10 g/kg body weight. According to another embodiment, the therapeutically effective amount is from about 0.00001 mg/kg body weight to about 10 g/kg body weight. According to another embodiment, the therapeutically effective amount is from about 0.00002 mg/kg body weight to about 10 g/kg body weight. According to another embodiment, the therapeutically effective amount is from about 0.0003 mg/kg body weight to about 10 g/kg body weight. According to another embodiment, the therapeutically effective amount is from about 0.00004 mg/kg body weight to about 10 g/kg body weight. According to another embodiment, the therapeutically effective amount is from about 0.00005 mg/kg body weight to about 10 g/kg body weight. According to another embodiment, the therapeutically effective amount is from about 0.00006 mg/kg body weight to about 10 g/kg body weight. According to another embodiment, the therapeutically effective amount is from about 0.00007 mg/kg body weight to about 10 g/kg body weight. According to another embodiment, the therapeutically effective amount is from about 0.00008 mg/kg body weight to about 10 g/kg body weight. According to another embodiment, the therapeutically effective amount is from about 0.00009 mg/kg body weight to about 10 g/kg body weight. According to another embodiment, the therapeutically effective amount is from about 0.0001 mg/kg body weight to about 10 g/kg body weight. According to some such embodiments, the therapeutically effective amount is about 0.0005 mg/kg body weight. According to some such embodiments, the therapeutically effective amount is about 0.001 mg/kg body weight. According to some such embodiments, the therapeutically effective amount is about 0.005 mg/kg body weight. According to some such embodiments, the therapeutically effective amount is about 0.01 mg/kg body weight. According to some such embodiment, the therapeutically effective amount is about 0.1 mg/kg body weight. According to some such embodiments, the therapeutically effective amount is about 1 mg/kg body weight. According to some such embodiments, the therapeutically effective amount is about 10 mg/kg body weight. According to some such embodiments, the therapeutically effective amount is about 20 mg/kg body weight. According to some such embodiments, the therapeutically effective amount is about 30 mg/kg body weight. According to some such embodiments, the therapeutically effective amount is about 40 mg/kg body weight. According to some such embodiments, the therapeutically effective amount is about 50 mg/kg body weight. According to some such embodiments, the therapeutically effective amount is about 60 mg/kg body weight. According to some such embodiments, the therapeutically effective amount is about 70 mg/kg body weight. According to some such embodiments, the therapeutically effective amount about 80 mg/kg body weight. According to some such embodiments, the therapeutically effective amount is about 90 mg/kg body weight. According to some such embodiments, the therapeutically effective amount is about 100 mg/kg body weight. According to some such embodiments, the therapeutically effective amount is about 110 mg/kg body weight. According to some such embodiments, the therapeutically effective amount is about 120 mg/kg body weight. According to some such embodiments, the therapeutically effective amount is about 130 mg/kg body weight. According to some such embodiments, the therapeutically effective amount is about 140 mg/kg body weight. According to some such embodiments, the therapeutically effective amount is about 150 mg/kg body weight. According to some such embodiments, the therapeutically effective amount is about 160 mg/kg body weight. According to some such embodiments, the therapeutically effective amount is about 170 mg/kg body weight. According to some such embodiments, the therapeutically effective amount is about 180 mg/kg body weight. According to some such embodiments, the therapeutically effective is about 190 mg/kg body weight. According to some such embodiments, the therapeutically effective amount is about 200 mg/kg body weight. According to some such embodiments, the therapeutically effective amount is about 250 mg/kg body weight. According to some such embodiments, the therapeutically effective amount is about 500 mg/kg body weight.

V. Method for Treating the Severity of Rebleeding after Surgical Evacuation of a Hematoma Resulting from a Hemorrhagic Brain Condition Additionally, the described invention provides a method of preventing or reducing the severity of rebleeding after surgical evacuation of a hematoma resulting from a hemorrhagic brain condition, the method comprising the step (a) implanting, at a distance in proximity to at least one edge of the hematoma, a pharmaceutical composition comprising (i) a therapeutically effective amount of an active agent and (ii) a coating, wherein the active agent produces a localized pharmocologic effect. According to one embodiment, the hemorrhagic brain condition is a chronic SDH. According to another embodiment, the hemorrhagic brain condition is an intracerebral hematoma.

According to one embodiment, the hemorrhagic condition of the brain is a chronic SDH.

According to another embodiment, the hemorrhagic condition of the brain is an intracranial hemorrhage.

According to another embodiment, the condition of the brain is a cavity. According to some such embodiments, the cavity is a cavity created after removal of a tumor. According to some such embodiments, the cavity is a cavity created after removal of an infection. According to some such embodiments, the cavity is a cavity created after removal of a portion of brain. According to some such embodiments, the cavity is a cavity created after removal of a vascular malformation of the brain.

According to another embodiment, the active agent comprises aminocaproic acid. According to another embodiment, the active agent comprises tranexamic acid. According to another embodiment, the active agent comprises Factor VII. According to another embodiment, the active agent comprises recombinant Factor VII. According to another embodiment, the active agent comprises aprotinin. According to another embodiment, the active agent comprises antiplasmin. According to another embodiment, the active agent comprises fibrin fragment D. According to another embodiment, the active agent comprises vitamin K. According to another embodiment, the active agent comprises vitamin K1. According to another embodiment, the active agent comprises vitamin K2. According to another embodiment, the active agent comprises vitamin K3. According to another embodiment, the active agent comprises 4-aminomethylbenzoic acid or an ester, salt, hydrate, solvate, prodrug or functional derivative thereof.

According to one embodiment, the pharmaceutical composition comprises a gel. According to another embodiment, the pharmaceutical composition comprises a slow-release solid. According to another embodiment, the pharmaceutical composition comprises a semisolid compound.

According to another embodiment, the pharmaceutical composition is a controlled release pharmaceutical composition. According to another embodiment, the pharmaceutical composition is a slow-release pharmaceutical composition. According to another embodiment, the pharmaceutical composition is a sustained-release pharmaceutical composition.

According to another embodiment, the coating comprises at least one pharmaceutically acceptable polymer. According to some embodiments, the coating forms a matrix with the active agent, wherein the active agent is of a desired release pattern. According to some embodiments, the coating is admixed with the active agent during the granulation stage of formulation.

According to another embodiment, the distance in proximity to at least one edge of the hematoma is from about 0.5 mm to about 10 mm from the at least one edge of the hematoma. According to another embodiment, the distance in proximity to at least one edge of the hematoma is from about 0.5 mm to about 9 mm from the at last one edge of the hematoma. According to another embodiment, the distance in proximity to at least one edge of the hematoma is from about 0.5 mm to about 8 mm from the at least one edge of the hematoma. According to another embodiment, the distance in proximity to at least one edge of the hematoma is from about 0.5 mm to about 7 mm from the at least one edge of the hematoma. According to another embodiment, the distance in proximity to at least one edge of the hematoma is from about 0.5 mm to about 6 mm from the at least one edge of the hematoma. According to another embodiment, the distance in proximity to at least one edge of the hematoma is from about 0.5 mm to about 5 mm from the at least one edge of the hematoma. According to another embodiment, the distance in proximity to at least one edge of the hematoma is from about 0.5 mm to about 4 mm from the at least one edge of the hematoma. According to another embodiment, the distance in proximity to at least one edge of the hematoma is from about 0.5 mm to about 3 mm from the at least one edge of the hematoma. According to another embodiment, the distance in proximity to at least one edge of the hematoma is from about 0.5 mm to about 2 mm from the at least one edge of the hematoma. According to another embodiment, the distance in proximity to at least one edge of the hematoma is from about 0.5 mm to about 1 mm from the at least one edge of the hematoma.

According to another embodiment, the distance in proximity to at least one edge of the hematoma is from about 0.6 mm to about 10 mm from the at least one edge of the hematoma. According to another embodiment, the distance in proximity to at least one edge of the hematoma is from about 0.6 mm to about 9 mm from the at last one edge of the hematoma. According to another embodiment, the distance in proximity to at least one edge of the hematoma is from about 0.6 mm to about 8 mm from the at least one edge of the hematoma. According to another embodiment, the distance in proximity to at least one edge of the hematoma is from about 0.6 mm to about 7 mm from the at least one edge of the hematoma. According to another embodiment, the distance in proximity to at least one edge of the hematoma is from about 0.6 mm to about 6 mm from the at least one edge of the hematoma. According to another embodiment, the distance in proximity to at least one edge of the hematoma is from about 0.6 mm to about 5 mm from the at least one edge of the hematoma. According to another embodiment, the distance in proximity to at least one edge of the hematoma is from about 0.6 mm to about 4 mm from the at least one edge of the hematoma. According to another embodiment, the distance in proximity to at least one edge of the hematoma is from about 0.6 mm to about 3 mm from the at least one edge of the hematoma. According to another embodiment, the distance in proximity to at least one edge of the hematoma is from about 0.6 mm to about 2 mm from the at least one edge of the hematoma. According to another embodiment, the distance in proximity to at least one edge of the hematoma is from about 0.6 mm to about 1 mm from the at least one edge of the hematoma.

According to another embodiment, the distance in proximity to at least one edge of the hematoma is from about 0.7 mm to about 10 mm from the at least one edge of the hematoma. According to another embodiment, the distance in proximity to at least one edge of the hematoma is from about 0.7 mm to about 9 mm from the at last one edge of the hematoma. According to another embodiment, the distance in proximity to at least one edge of the hematoma is from about 0.7 mm to about 8 mm from the at least one edge of the hematoma. According to another embodiment, the distance in proximity to at least one edge of the hematoma is from about 0.7 mm to about 7 mm from the at least one edge of the hematoma. According to another embodiment, the distance in proximity to at least one edge of the hematoma is from about 0.7 mm to about 6 mm from the at least one edge of the hematoma. According to another embodiment, the distance in proximity to at least one edge of the hematoma is from about 0.7 mm to about 5 mm from the at least one edge of the hematoma. According to another embodiment, the distance in proximity to at least one edge of the hematoma is from about 0.7 mm to about 4 mm from the at least one edge of the hematoma. According to another embodiment, the distance in proximity to at least one edge of the hematoma is from about 0.7 mm to about 3 mm from the at least one edge of the hematoma. According to another embodiment, the distance in proximity to at least one edge of the hematoma is from about 0.7 mm to about 2 mm from the at least one edge of the hematoma. According to another embodiment, the distance in proximity to at least one edge of the hematoma is from about 0.7 mm to about 1 mm from the at least one edge of the hematoma.

According to another embodiment, the distance in proximity to at least one edge of the hematoma is from about 0.8 mm to about 10 mm from the at least one edge of the hematoma. According to another embodiment, the distance in proximity to at least one edge of the hematoma is from about 0.8 mm to about 9 mm from the at last one edge of the hematoma. According to another embodiment, the distance in proximity to at least one edge of the hematoma is from about 0.8 mm to about 8 mm from the at least one edge of the hematoma. According to another embodiment, the distance in proximity to at least one edge of the hematoma is from about 0.8 mm to about 7 mm from the at least one edge of the hematoma. According to another embodiment, the distance in proximity to at least one edge of the hematoma is from about 0.8 mm to about 6 mm from the at least one edge of the hematoma. According to another embodiment, the distance in proximity to at least one edge of the hematoma is from about 0.8 mm to about 5 mm from the at least one edge of the hematoma. According to another embodiment, the distance in proximity to at least one edge of the hematoma is from about 0.8 mm to about 4 mm from the at least one edge of the hematoma. According to another embodiment, the distance in proximity to at least one edge of the hematoma is from about 0.8 mm to about 3 mm from the at least one edge of the hematoma. According to another embodiment, the distance in proximity to at least one edge of the hematoma is from about 0.8 mm to about 2 min from the at least one edge of the hematoma. According to another embodiment, the distance in proximity to at least one edge of the hematoma is from about 0.8 mm to about 1 mm from the at least one edge of the hematoma.

According to another embodiment, the distance in proximity to at least one edge of the hematoma is from about 0.9 mm to about 10 mm from the at least one edge of the hematoma. According to another embodiment, the distance in proximity to at least one edge of the hematoma is from about 0.9 mm to about 9 mm from the at last one edge of the hematoma. According to another embodiment, the distance in proximity to at least one edge of the hematoma is from about 0.9 mm to about 8 mm from the at least one edge of the hematoma. According to another embodiment, the distance in proximity to at least one edge of the hematoma is from about 0.9 nun to about 7 mm from the at least one edge of the hematoma. According to another embodiment, the distance in proximity to at least one edge of the hematoma is from about 0.9 mm to about 6 mm from the at least one edge of the hematoma. According to another embodiment, the distance in proximity to at least one edge of the hematoma is from about 0.9 mm to about 5 mm from the at least one edge of the hematoma. According to another embodiment, the distance in proximity to at least one edge of the hematoma is from about 0.9 mm to about 4 mm from the at least one edge of the hematoma. According to another embodiment, the distance in proximity to at least one edge of the hematoma is from about 0.9 mm to about 3 mm from the at least one edge of the hematoma. According to another embodiment, the distance in proximity to at least one edge of the hematoma is from about 0.9 mm to about 2 mm from the at least one edge of the hematoma. According to another embodiment, the distance in proximity to at least one edge of the hematoma is from about 0.9 mm to about 1 mm from the at least one edge of the hematoma.

According to another embodiment, the distance in proximity to at least one edge of the hematoma is from about 1 mm to about 10 mm from the at least one edge of the hematoma. According to another embodiment, the distance in proximity to at least one edge of the hematoma is from about 2 mm to about 10 mm from the at least one edge of the hematoma. According to another embodiment, the distance in proximity to at least one edge of the hematoma is from about 3 mm to about 10 mm from the at least one edge of the hematoma. According to another embodiment, the distance in proximity to at least one edge of the hematoma is from about 4 mm to about 10 mm from the at least one edge of the hematoma. According to another embodiment, the distance in proximity to at least one edge of the hematoma is from about 5 mm to about 10 mm from the at least one edge of the hematoma. According to another embodiment, the distance in proximity to at least one edge of the hematoma is from about 6 min to about 10 mm from the at least one edge of the hematoma. According to another embodiment, the distance in proximity to at least one edge of the hematoma is from about 7 mm to about 10 mm from the at least one edge of the hematoma. According to another embodiment, the distance in proximity to at least one edge of the hematoma is from about 8 mm to about 10 mm from the at least one edge of the hematoma. According to another embodiment, the distance in proximity to at least one edge of the hematoma is from about 9 mm to about 10 mm from the at least one edge of the hematoma. According to another embodiment, the distance in proximity to at least one edge of the hematoma is from about 9.5 mm to about 10 mm from the at least one edge of the hematoma. According to another embodiment, the distance in proximity to at least one edge of the hematoma is from about 9.6 mm to about 10 mm from the at least one edge of the hematoma. According to another embodiment, the distance in proximity to at least one edge of the hematoma is from about 9.7 mm to about 10 mm from the at least one edge of the hematoma. According to another embodiment, the distance in proximity to at least one edge of the hematoma is from about 9.8 mm to about 10 mm from the at least one edge of the hematoma. According to another embodiment, the distance in proximity to at least one edge of the hematoma is from about 9.9 mm to about 10 mm from the at least one edge of the hematoma.

According to another embodiment, the pharmaceutical composition is implanted by surgical injection.

According to another embodiment, the therapeutically effective amount of the composition is from about 0.000001 mg/kg body weight to about 10 g/kg body weight. According to another embodiment, the therapeutically effective amount is from about 0.000002 mg/kg body weight to about 10 g/kg body weight. According to another embodiment, the therapeutically effective amount is from about 0.000003 mg/kg body weight to about 10 g/kg body weight. According to another embodiment, the therapeutically effective amount is from about 0.000004 mg/kg body weight to about 10 g/kg body weight. According to another embodiment, the therapeutically effective amount is from about 0.000005 mg/kg body weight to about 10 g/kg body weight. According to another embodiment, the therapeutically effective amount is from about 0.000006 mg/kg body weight to about 10 g/kg body weight. According to another embodiment, the therapeutically effective amount is from about 0.000007 mg/kg body weight to about 10 g/kg body weight. According to another embodiment, the therapeutically effective amount is from about 0.000008 mg/kg body weight to about 10 g/kg body weight. According to another embodiment, the therapeutically effective amount is from about 0.000009 mg/kg body weight to about 10 g/kg body weight. According to another embodiment, the therapeutically effective amount is from about 0.00001 mg/kg body weight to about 10 g/kg body weight. According to another embodiment, the therapeutically effective amount is from about 0.00002 mg/kg body weight to about 10 g/kg body weight. According to another embodiment, the therapeutically effective amount is from about 0.0003 mg/kg body weight to about 10 g/kg body weight. According to another embodiment, the therapeutically effective amount is from about 0.00004 mg/kg body weight to about 10 g/kg body weight. According to another embodiment, the therapeutically effective amount is from about 0.00005 mg/kg body weight to about 10 g/kg body weight. According to another embodiment, the therapeutically effective amount is from about 0.00006 mg/kg body weight to about 10 g/kg body weight. According to another embodiment, the therapeutically effective amount is from about 0.00007 mg/kg body weight to about 10 g/kg body weight. According to another embodiment, the therapeutically effective amount is from about 0.00008 mg/kg body weight to about 10 g/kg body weight. According to another embodiment, the therapeutically effective amount is from about 0.00009 mg/kg body weight to about 10 g/kg body weight. According to another embodiment, the therapeutically effective amount is from about 0.0001 mg/kg body weight to about 10 g/kg body weight. According to some such embodiments, the therapeutically effective amount is about 0.0005 mg/kg body weight. According to some such embodiments, the therapeutically effective amount is about 0.001 mg/kg body weight. According to some such embodiments, the therapeutically effective amount is about 0.005 mg/kg body weight. According to some such embodiments, the therapeutically effective amount is about 0.01 mg/kg body weight. According to some such embodiment, the therapeutically effective amount is about 0.1 mg/kg body weight. According to some such embodiments, the therapeutically effective amount is about 1 mg/kg body weight. According to some such embodiments, the therapeutically effective amount is about 10 mg/kg body weight. According to some such embodiments, the therapeutically effective amount is about 20 mg/kg body weight. According to some such embodiments, the therapeutically effective amount is about 30 mg/kg body weight. According to some such embodiments, the therapeutically effective amount is about 40 mg/kg body weight. According to some such embodiments, the therapeutically effective amount is about 50 mg/kg body weight. According to some such embodiments, the therapeutically effective amount is about 60 mg/kg body weight. According to some such embodiments, the therapeutically effective amount is about 70 mg/kg body weight. According to some such embodiments, the therapeutically effective amount about 80 mg/kg body weight. According to some such embodiments, the therapeutically effective amount is about 90 mg/kg body weight. According to some such embodiments, the therapeutically effective amount is about 100 mg/kg body weight. According to some such embodiments, the therapeutically effective amount is about 110 mg/kg body weight. According to some such embodiments, the therapeutically effective amount is about 120 mg/kg body weight. According to some such embodiments, the therapeutically effective amount is about 130 mg/kg body weight. According to some such embodiments, the therapeutically effective amount is about 140 mg/kg body weight. According to some such embodiments, the therapeutically effective amount is about 150 mg/kg body weight. According to some such embodiments, the therapeutically effective amount is about 160 mg/kg body weight. According to some such embodiments, the therapeutically effective amount is about 170 mg/kg body weight. According to some such embodiments, the therapeutically effective amount is about 180 mg/kg body weight. According to some such embodiments, the therapeutically effective is about 190 mg/kg body weight. According to some such embodiments, the therapeutically effective amount is about 200 mg/kg body weight. According to some such embodiments, the therapeutically effective amount is about 250 mg/kg body weight. According to some such embodiments, the therapeutically effective amount is about 500 mg/kg body weight.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

The described invention may be embodied in other specific forms without departing from the spirit or essential attributes thereof and, accordingly, reference should be made to the appended claims, rather than to the foregoing specification, as indicating the scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Non-Human Animal Model of Chronic Subdural Hematoma (SDH)

1.1. Formation of Chronic Subdural Hematoma in a Mouse Model

Meninges of the Spinal Cord

The spinal dura mater (dura mater spinalis; spinal dura), which forms a loose sheath around the medulla spinalis (spinal cord), represents only the inner or meningeal layer of the cranial dura mater; the outer or endosteal layer ceases at the foramen magnum, its place being taken by the periosteum lining the vertebral canal. The spinal dura mater is separated from the arachnoid by a potential cavity (the "subdural cavity"); the two membranes are, in fact, in contact with each other, except where they are separated by a minute quantity of fluid, which serves to moisten the apposed surfaces. The spinal dura mater is separated from the wall of the vertebral canal by a space (the "epidural space"), which contains a quantity of loose areolar tissue and a plexus of veins; the situation of these veins between the dura mater and the periosteum of the vertebrae corresponds therefore to that of the cranial sinuses between the meningeal and endosteal layers of the cranial dura mater. The spinal dura mater is attached to the circumference of the foramen magnum, to the second and third cervical vertebrae, and to the posterior longitudinal ligament, especially near the lower end of the vertebral canal, by fibrous slips. The subdural cavity ends at the lower border of the second sacral vertebra; below this level, the dura mater closely invests the filum terminale (the slender thread-like prolongation of the spinal cord below the origin of the lumbar nerves (the last portion of the pia mater)) and descends to the back of the coccyx, where it blends with the periosteum. The sheath of dura mater is much larger than is necessary for the accommodation of its contents, and its size is greater in the cervical and lumbar regions than in the thoracic. On each side may be seen the double openings that transmit the two roots of the corresponding spinal nerve are on each side, with the dura mater being continued in the form of tubular prolongations on the nerves as they pass through the intervertebral foramina. These prolongations are short in the upper part of the vertebral column, but gradually become longer below, forming a number of tubes of fibrous membrane, which enclose the lower spinal nerves and are contained in the vertebral canal.

The spinal dura mater resembles the meningeal or supporting layer of the cranial dura mater in structure. It consists of white fibrous and elastic tissue arranged in bands or lamallac which, for the most part, are parallel with one another and have a longitudinal arrangement. Its internal surface is smooth and covered by a layer of mesothelium. It is sparingly supplied with blood vessels, and a few nerves have been traced into it.

The spinal part (arachnoidea spinalis) of the arachnoid is a thin, delicate, tubular membrane loosely investing the spinal cord. Above, it is continuous with the cranial arachnoid; below, it widens out and invests the cauda equina (the bundle of spinal nerve roots from lombar and sacral spinal nerves running through the lower part of the subarachnoid space within the vertebral canal below the first lumbar vertebra) and the nerves proceeding from it. It is separated from the dura mater by the subdural space, but intermittently this space is traversed by isolated connective-tissue trabeculae, which are most numerous on the posterior surface of the spinal cord.

The spinal part of the subarachnoid cavity is a very wide space, and is the largest at the lower part of the vertebral canal, where the arachnoid encloses the nerves which form the cauda equina. Above, it is continuous with the cranial subarachnoid cavity; below, it ends at the level of the lower border of the second sacral vertebra. It is partially divided by a longitudinal septum (the subarachnoid septum), which connects the arachnoid with the pia mater opposite the posterior median sulcus of the spinal cord, and forms a partition, incomplete and perforated above, but more perfect in the thoracic region. The spinal subarachnoid cavity is further subdivided by the ligamentum denticulatum (a serrated, shelf-like extension of the spinal pia mater projecting in a frontal plane from either side of the cervical and thoracic spinal cord).

The spinal pia mater (pia mater spinalis; pia of the cord), which is thicker, firmer, and less vascular than the cranial pia mater, consists of two layers. The outer or additional pia mater layer is composed of bundles of connective-tissue fibers, arranged for the most part longitudinally. Cleft-like spaces, which communicate with the subarachnoid cavity, and a number of blood vessels, which are enclosed in perivascular lymphatic sheaths, are between the layers. The spinal pia mater covers the entire surface of the spinal cord, and is very intimately adherent to it; in front it sends a process backward into the anterior fissure. A longitudinal fibrous band (the linea splendens) extends along the middle line of the anterior surface; and the ligamentum denticulatum is situated on either side. Below the conus medullaris (the terminal end of the spinal cord), the pia mater is continued as a long, slender filament (filum terminale), which descends through the center of the mass of nerves forming the cauda equina. It blends with the dura mater at the level of the lower border of the second sacral vertebra, and extends downward as far as the base of the coccyx, where it fuses with the periosteum. The pia mater assists in maintaining the spinal cord in its position during the movements of the trunk, and is, from this circumstance, called the central ligament of the spinal cord.

Experimental Protocol

Chronic SDH will be formed in a mouse model. Adult C57BL6, CD1, or other appropriate strain of mice weighing 25-35 grams will be sedated with ketamine (100 mg/kg) and xylazine (10 mg/kg) intraperitoneally. Body temperature will be maintained at 37° C. with a rectal temperature probe and homeothermic pad. Donor mice (or rats) will be anesthesized (ketamine (100 mg/kg) and xylazine (10 mg/kg) intraperitoneally) and blood collected from the external jugular vein using a 21-gauge catheter. The collected allogeneic (or xenogeneic) blood immediately will be injected (in a volume of either 2 ml, 5 ml or 10 ml) into the subcutaneous space of the thoracic spine of recipient mice. The initial hematoma will be measured immediately using digital calipers. Hematoma measurement will be in duplicate, each measurement performed independently by a different trained technician, and subsequent measurements will be performed thrice daily every second day after injection. Animals will be placed under general anesthesia, then perfused through the left ventricle with NaCl (0.9%, 50 ml) and paraformaldehyde (4%, 120 ml in phosphate buffered saline (PBS)) for 20 minutes, when either (i) the hematoma begins to decrease in size, or (ii) the hematoma sequentially expands in size for about 6 days.

The hematoma will be widely dissected from the thoracic spine so that the hematoma remains intact, and then sectioned coronally across the middle. For histology studies, a block will be embedded with paraffin, sectioned (10 µm), stained with hematoxylin and eosin, and examined (i) quantitatively for granulation and tissue thickness, and (ii) qualitatively for inflammatory cells, neovascularity, macrophages, eosinophils and other histological features.

Immunohistochemistry will be performed on a portion of the coronal section. The tissue will be fixed (4% paraformaldehyde) overnight, embedded in suitable medium, such as, for example, optimal cutting temperature (OCT) medium (Biogenex, Markham, Ontario), and frozen on dry ice. Subsequent sectioning (10 µm) will be performed with a cryostat, and the sections blocked (phosphate-buffered saline (PBS) containing 10% normal goat serum, 1% bovine serum albumin, and 0.1% sodium azide), and permeabilized (0.3% Triton X-100) for 1 hour with gentle rocking. Primary antibodies for immunofluorescence (commercially available from vendors such as Abeam, Cambridge, Mass.) will be antibodies to macrophages (CD68), tissue-type and urokinase-type plasminogen activators, TNFα, IL-6 and IL-8. Sections will be incubated with primary antibody in PBS with 1% BSA followed by washing and application of secondary antibodies (for example, Alexa Fluor 568 (Invitrogen, Carlsbad, Calif.) goat antibodies to the appropriate species and isotype). After final washing, sections will be protected with cover slips with anti-fading mounting medium sealed with nail polish and stored at 4° C.

Sections will be viewed on a confocal microscope with a charge-coupled device (CCD) camera. Consistent acquisition parameters (exposure time, laser power strength and pin hole size) will be utilized. Cell numbers will be quantified from randomly selected images (n=10) of the hematoma wall using unbiased counting rules and 2 viewers (blinded to the experimental group) who will count the stained cells.

Hematoma volumes will be calculated as if each hematoma were an ellipsoid (Volume=$4/3\pi ABC$ where A, B and C are the 3 orthogonal radii). Comparisons between groups will be performed by analysis of variance (ANOVA) or ANOVA for repeated measurements, as appropriate, followed by Turkey's multiple comparison tests. Comparisons between two measurements will be by paired t-tests within groups and unpaired t-tests between different groups. Linear regression will be used utilizing the least-squares method and fits to curves will be performed using the Levenburg-Marquardt algorithm in SigmaPlot (Statistical Package for the Social Sciences [SPSS}, Chicago, Ill.) or Stata (Stata Corp., College Station, Tex.). Nonparametric measurements will be compared by $x^2$, or Fisher's exact test.

Example 3

Another Model of Chronic Subdural Hematoma in Mice

Figure 9:
FIG. 9 shows histology of a subdural hematoma in a mouse model of chronic subdural hematoma, which is developed by a single injection of 6-aminonicotinamide (25 mg/kg body weight).

In another model, a chronic SDH can be created by a single intraperitoneal injection of 6-aminonicotinamide (25 mg/kg body weight) on the 5th postnatal day in neonatal mice. A certain number of these mice can spontaneously develop spontaneous SDH 20 or more days after the injection. Controls can be injected with same volume of physiological saline. The hematomas are assessed after perfusing anesthetized mice through the left cardiac ventricle with NaCl, 0.9%, 50 ml, followed by 4% paraformaldehyde in phosphate-buffered saline (PBS), 120 ml, over 20 minutes (FIG. 9).

Example 4

Time Course and Fluid Analysis of Chronic Subdural Hematoma in Mice

The time course for the formation of a chronic SDH and a fluid analysis of the chronic SDH will be performed. A volume of allogenic blood (2 ml, 5 ml or 10 ml) will be injected into the subcutaneous space of the thoracic spine of recipient mice and the time of hematoma formation will be monitored. Hematoma fluid will be aspirated into siliconized tubes containing prolamine sulfate and ethylene diamine tetraacetic acid (EDTA) immediately prior to sacrifice of the animal. Control venous blood will be obtained from the femoral vein. All samples will be centrifuged (3000 rpm for 10 minutes), then the supernatant removed and stored (−80° C.). Samples will be analyzed for $\alpha_2$-antiplasmin, plasmin-$\alpha_2$-antiplasmin complex, IL-6, IL-8 and TNFα using commercially available ELISA kits (from, for example, R and D Systems, Minneapolis, Minn. or American Diagnostica, Stamford, Conn.).

Example 5

Knockout Mice to Manipulate of Fibrinolysis

Wild-type mice and mice with knockout of t-PA and α2-antiplasmin will undergo injection of allogenic blood into the subcutaneous space over the throracic spine. Hematoma volume will be measured by digital calipers. At euthanasia, hematomas will be assessed histologically and immunochemically and the hematoma fluid analyzed for fibrinolytic markers such as plasminogen activators, $\alpha_2$-antiplasmin, plasmin-α2-antiplasmin complex.

Example 6

Pharmacological Manipulation of Fibrinolysis

A pharmaceutical composition comprising PLGA or a similar biodegradable polymer with tranexamic acid will be synthesized. Briefly, six formulations of tranexamic acid and PLGA will be synthesized with varying release kinetics. Release kinetics will be varied by altering the components of the PLGA. The different formulations will be tested for their in vitro release kinetics in the mouse model. Release of tranexamic acid will be measured by thromboelastography.

Example 7

Rat Model of ICH

Formulations will be tested in a rat collagenase model of ICH, which is more likely to be associated with continuous hemorrhage than other models in which single blood injections are administered. (Eiger, B. et al., J. Stroke Cerebrovasc. Dis. 7: 10, 1998).

Groups of 10 rats will undergo injection of collagenase into the caudate nucleus along with a formulation of the described invention. Rats will undergo surgery under general anesthesia induced with intraperitoneal injection of ketamine (90 mg/kg) and xylazine 10 mg/kg). The scalp will be prepared sterilely with povidone iodine and a midline incision will be made from anterior to the bregma [the craniometric point at the junction of the sagittal and coronal sutures at the top of the cranium] to the occipital bone. The skull will be exposed and a hole will be drilled with a 1 mm drill over the caudate nucleus. The tail artery will be catheterized with PE10 tubing sutured in place and connected to a pressure transducer with rigid tubing filled with 0.9% NaCl. Body temperature will be maintained and monitored with a heating pad, and rectal temperature probe. Baseline blood pressure and body temperature will be recorded for 15 minutes, after which collagenase (Type IV, 0.15 units, for example from Worthington Biochemicals, Lakewood, N.J.) with our without control or formulation will be injected.

Animals will be euthanized from 1 to 10 days after ICH and the brains removed and examined grossly and histologically. The brains will be fixed in formalin and then sections of the hemispheres cut, embedded in paraffin, sectioned and stained with hematoxylin and eosin. The size of the hematomas will be measured by planimetry using standard morphometric methods. Samples will be examined and the degree of brain parencyhmal inflammation will be assessed by overall appearance, number of infiltrating polynuclear neutrophils in the connective tissue around the injection site, number of monocytes, presence of any necrosis, capillary proliferation and fibrosis. Changes will be scored on a three-point scale, where 1=neutrophil infiltration with little or no inflammatory components; 2=non-suppurative inflammation; and 3=cell necrosis with acute suppurative inflammation.

Serum effects of the compositions of the invention will be determined by thromboclastography on days 2 and 5.

Example 8

Synthesis of Sustained-Release Anti-fibrinolytic Agent Composition

A pharmaceutical composition comprising a sustained-release carrier, such as, PLGA or a similar biodegradable polymer, can be co-synthesized with an antifibrinolytic agent, (e.g., E-aminocaproic acid (AMICAR), factor VII (wild type or recombinant), aprotinin, tranexamic acid). For example, the sustained-release anti-fibrinolytic agent can be either embedded into or coated on microparticles (50 microns) made of poly(D,L-lactide-co-glycolide).

In order to determine pharmacokinetics of the sustained-release anti-fibrinolytic agent composition, six formulations of a fibrinolytic agent and PLGA can be synthesized with varying release kinetics. Release kinetics can be varied by altering the components of the PLGA. The different formulations are then tested for their ability, when administered with collagenase in vivo, to decrease the volume of ICH in a rat model of ICH. Release of fibrinolytic agent can be measured by thromboelastography.

Example 9

Treatment of Hematoma Expansion or Recurrent Bleeding by Site-Specific Administration of Sustained-Release Anti-Fibrinolytic Agent Compositions A patient diagnosed with intracerebral hemorrhage by CT scan can be treated by implanting a plurality of sustained-release microparticles including an anti-fibrinolytic agent ∈-aminocaproic acid, Factor VII, tranexamic acid, or aprotinin). For example, a plurality of sustained-release microparticles (50 microns) made of poly(D,L,-lactide-co-glycolide) containing ∈-aminocaproic acid can be implanted into or near the hematoma in the patient's brain within 72 hours after the baseline CT scan or no later than 96 hours after the onset of symptoms. Dosing for each anti-fibrinolytic agent can be based on estimated body weight. Once implanted, the sustained-released microparticle can release the anti-fibrinolytic agent for a specific time window (e.g., 3-5 days), when most rebleeding occurs.

Follow-up CT scans are performed at target intervals of 24 hours (range 21 to 27) and 72 hours (range 66 to 78) after implantation. Digital CT data can be analyzed with the use of Analyze software (Mayo Clinic) by neuroradiologists. The volumes of intracerebral hemorrhage, intraventricular hemorrhage, and edema can be calculated with the use of computerized planimetric techniques.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for treating hematoma expansion or recurrent bleeding resulting from a hemorrhagic condition in brain, the method comprising:
  (a) providing a flowable pharmaceutical composition for sustained release comprising
    (i) a therapeutic amount of at least one anti-fibrinolytic agent; and
    (ii) a pharmaceutically acceptable carrier, wherein the carrier comprises a plurality of microparticles, wherein the therapeutic agent is dispersed throughout each microparticle; and
  (b) administering the pharmaceutical composition locally in a cavity or space occupied by a hematoma or in a subdural space on the surface of the brain without entering systemic circulation in an amount to cause unwanted side effects;
  wherein the therapeutic amount is effective to reduce hematoma expansion or recurrent bleeding, when compared to a nontreated control.

2. The method according to claim 1, wherein the hemorrhagic condition, results from traumatic brain injury (TBI).

3. The method according to claim 1, wherein the hemorrhagic condition is rebleeding following a surgical evacuation of the hematoma.

4. The method according to claim 1, wherein the hemorrhagic condition is a chronic subdural hematoma (SDH).

5. The method according to claim 1, wherein the hemorrhagic condition is an intracerebral hematoma (ICH).

6. The method according to claim 5, wherein the intracerebral hematoma is a spontaneous intracerebral hematoma (ICH).

7. The method according to claim 5, wherein the intracerebral hematoma is a traumatic intracerebral hematoma (ICH).

8. The method according to claim 1, wherein the hemorrhagic condition is rebleeding following a craniotomy procedure.

9. The method according to claim 8, wherein the craniotomy procedure is performed for treating a brain cancer.

10. The method according to claim 8, wherein the craniotomy procedure is performed for treating a vascular malformation in brain.

11. The method according to claim 8, wherein the craniotomy procedure is performed for treating a brain aneurysm.

12. The method according to claim 1, wherein the at least one anti-fibrinolytic agent is ∈-aminocaproic acid (AMICAR).

13. The method according to, claim 1, wherein the at least one anti-fibrinolytic agent is tranexamioacid.

14. The method according to claim 1, wherein the at least one anti-fibrinolytic agent is aprotinin.

15. The method according to claim 1, wherein the pharmaceutically acceptable carrier is a controlled-release carrier.

16. The method according to claim 1, wherein the pharmaceutically acceptable carrier is a sustained-release carrier.

17. The method according to claim 16, wherein the at least one anti-fibrinolytic agent is embedded in the sustained-release carrier.

18. The method according to claim 16, wherein the at least one anti-fibrinolytic agent is coated on the sustained-release carrier.

19. The method according to claim 16, wherein the sustained-release carrier releases the at least one anti-fibrinolytic agent for at least 21 days post-administration.

20. The method according to claim 16, wherein the sustained-release carrier releases the at least one anti-fibrinolytic agent for about 3 to 5 days post-administration.

21. The method according to claim 16, wherein the sustained-release carrier is a nanoparticle.

22. The method according to claim 16, wherein the sustained-release carrier comprises a biodegradable polymer.

23. The method according to claim 22, wherein the biodegradable polymer is a synthetic polymer.

24. The method according to claim 22, wherein the biodegradable polymer is a naturally occurring polymer.

25. The method according to claim 23, wherein the synthetic polymer is selected from the group consisting of a polyester, a polyester polyethylene, glycol polymer, a polyamino-derived biopolymer; a polyanhydride, a polyorthoester, polyphosphazene, a sucrose acetate isobutyrate (SAIB), a photopolymerizable biopolymer, and a combination thereof.

26. The method according to claim 23, wherein the synthetic polymer is polyglyolic acid (PGA).

27. The method according to claim 23, wherein the synthetic polymer is a copolymer of polyglycolic acid formed with trimethylene carbonate, polylactic acid (PLA), or polycaprolactone.

28. The method according to claim 16, wherein the sustained-release carrier is a hydrogel.

29. The method according to claim 24, wherein the naturally occurring biopolymer is a protein polymer.

30. The method according to claim 24, wherein the naturally occurring polymer comprises hyaluronic acid.

31. The method according to claim 30, wherein the naturally occurring polymer comprises less than 2.3% of hyaluronic acid.

32. The method according to claim 1, wherein the distance proximal to the hematoma is from about 0.5 mm to about 10 mm.

33. The method according to claim 1, wherein the pharmaceutical composition exhibits a localized pharmacological effect in close proximity to the hematoma cavity.

34. The method according to claim 1, wherein the pharmaceutical composition exhibits a diffuse pharmacological effect throughout the hematoma-cavity.

* * * * *